(12) United States Patent
Galy

(10) Patent No.: US 11,993,781 B2
(45) Date of Patent: May 28, 2024

(54) STABLE PSEUDOTYPED LENTIVIRAL PARTICLES AND USES THEREOF

(71) Applicants: GENETHON, Evry (FR); INSERM (INSTITUT NATIONAL DE LA SANTÉ ET DE LA RECHERCHE MÉDICALE), Paris (FR); UNIVERSITE D'EVRY VAL D'ESSONNE, Evry (FR)

(72) Inventor: Anne Galy, Fontainebleau (FR)

(73) Assignees: Institut National de la Santé et de la Recherche Médicale, Paris (FR); Université d'Évry Val d'Éssonne

( * ) Notice: Subject to any disclaimer, the term of this patent is extended or adjusted under 35 U.S.C. 154(b) by 445 days.

(21) Appl. No.: 16/095,098

(22) PCT Filed: Apr. 21, 2017

(86) PCT No.: PCT/EP2017/059465
§ 371 (c)(1),
(2) Date: Oct. 19, 2018

(87) PCT Pub. No.: WO2017/182607
PCT Pub. Date: Oct. 26, 2017

(65) Prior Publication Data
US 2019/0300902 A1    Oct. 3, 2019

(30) Foreign Application Priority Data

Apr. 21, 2016 (EP) .................................. 16305466

(51) Int. Cl.
| | | |
|---|---|---|
| *C12N 15/63* | (2006.01) | |
| *A61K 35/17* | (2015.01) | |
| *A61K 35/76* | (2015.01) | |
| *C07H 21/04* | (2006.01) | |
| *C07K 14/005* | (2006.01) | |
| *C12N 5/0781* | (2010.01) | |
| *C12N 15/85* | (2006.01) | |
| *C12N 15/86* | (2006.01) | |
| *A61K 48/00* | (2006.01) | |

(52) U.S. Cl.
CPC .............. *C12N 15/86* (2013.01); *A61K 35/17* (2013.01); *A61K 35/76* (2013.01); *C07K 14/005* (2013.01); *C12N 5/0635* (2013.01); *A61K 48/00* (2013.01); *C12N 2740/10022* (2013.01); *C12N 2740/16022* (2013.01); *C12N 2740/16043* (2013.01); *C12N 2740/16052* (2013.01)

(58) Field of Classification Search
CPC ........ C12N 15/63; C12N 15/85; C12N 15/86; C12N 15/79; C12N 2740/16022; C12N 2740/16052; C12N 2740/16043; C12N 2510/00; C07H 21/04
See application file for complete search history.

(56) References Cited

FOREIGN PATENT DOCUMENTS

| | | | | |
|---|---|---|---|---|
| CN | 104080799 A | 10/2014 | | |
| JP | 2004508808 A | 3/2004 | | |
| JP | 2007510412 A | 4/2007 | | |
| JP | 2008507272 A | 3/2008 | | |
| JP | 2010535495 A | 11/2010 | | |
| WO | 97/44064 A2 | 11/1997 | | |
| WO | 2004/087748 A1 | 10/2004 | | |
| WO | WO-2004087748 A1 * | 10/2004 | ........... | C07K 14/005 |
| WO | WO 2011/011584 A1 * | 1/2011 | | |
| WO | 2013/001041 A1 | 1/2013 | | |

OTHER PUBLICATIONS

Lower (Journal of Virology, 69(1): 141-149, 1995). (Year: 1995).*
Mi (Nature 403:785-789, 2000 (Year: 2000).*
Kutner (Nature Protocols, 4(4): 495-505, 2009) (Year: 2009).*
Reiser (Gene Therapy, 7: 910-913, 2000). (Year: 2000).*
J. M. Antony et al: "The Human Endogenous Retrovirus Envelope Glycoprotein, Syncytin-1, Regulates Neuroinflammation and Its Receptor Expression in Multiple Sclerosis: A Role for Endoplasmic Reticulum Chaperones in Astrocytes", The Journal of Immunology, vol. 179, No. 2, pp. 1210-1224, Jul. 15, 2007.
Blaise, Journal of Virology., 2004, 78, 1050-1054, American Society for Microbiology.
Tory Weston, Viral Vector Patents by Others,Jan. 3, 2021,https://www.scienceforums.com/topic/37609-viral-vector-patents-status-by-others/.†

* cited by examiner
† cited by third party

*Primary Examiner* — Shin Lin Chen
(74) *Attorney, Agent, or Firm* — WCF IP

(57) ABSTRACT

The present invention relates to a method for obtaining stable pseudotyped lentiviral particles including a heterologous gene of interest, comprising the following steps: a) transfecting at least one plasmid in appropriate cell lines, wherein said at least one plasmid comprises the gene of interest, the rev. gag and pol genes, and a sequence coding for an ERV syncytin, wherein the rev, gag and pol genes are retroviral genes; b) incubating the transfected cells obtained in a), so that they produce the stable pseudotyped lentiviral particles in the supernatant; and c) harvesting and concentrating the stable lentiviral particles obtained in b). The present invention also relates to a method to transduce immune cells using lentiviral vectors pseudotyped with an ERV syncytin glycoprotein. The method can be performed on non-stimulated blood cells or on cells stimulated briefly with IL7, and the cells can be expanded. The stable pseudotyped lentiviral particles obtained are particularly useful in gene therapy.

5 Claims, 20 Drawing Sheets

Figure 1:
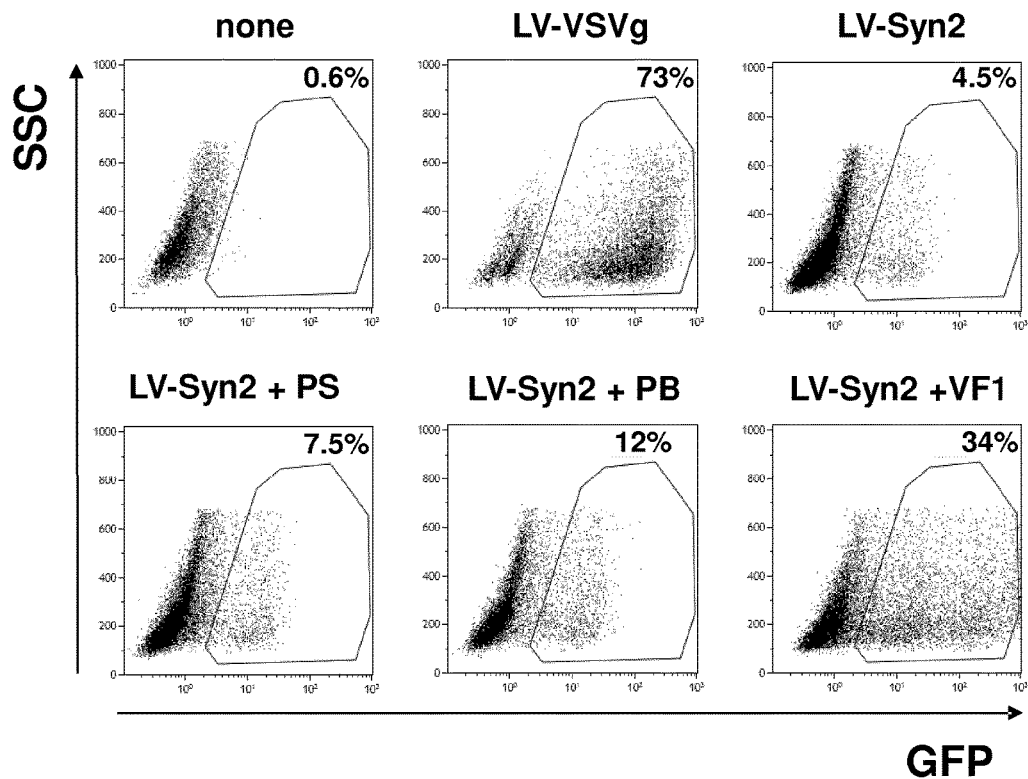

Specification includes a Sequence Listing.

B

C

A

Healthy PBMC

B

SCID-X1 PBMC

*(a)*

*(b)* B Lymphocytes

*(c)* T Lymphocytes

STABLE PSEUDOTYPED LENTIVIRAL PARTICLES AND USES THEREOF

FIELD OF THE INVENTION

The present invention relates to stable pseudotyped lentiviral particles and uses thereof, particularly in therapy. The invention also refers to a method for preparing such stable pseudotyped lentiviral particles. The invention also relates to an in vitro method to transduce human peripheral blood naive B cells and monocytic cells, preferably with minimal or no pre-activation, using such pseudotyped lentiviral particles, in the presence of vectofusin.

BACKGROUND OF THE INVENTION

Gene therapy approaches are often hampered by low transduction efficiencies of target cells by recombinant viral vectors. Retroviral vectors, and in particular human immunodeficiency virus 1 (HIV-1)-based lentiviral vectors (LVs) are promising vehicles for gene therapy. These vectors are used currently in clinical applications to treat various diseases such as immune deficiencies, neurodegenerative or neurological diseases, anemias or HIV infection.

Some of the applications of retroviral vectors rely on the transduction of specific target cells ex vivo such as lymphocytes or hematopoietic stem/progenitor cells expressing the CD34 marker. LVs are used to transduce T lymphocytes to generate long-lived CAR-T cells for the treatment of cancers such as refractory chronic lymphocytic leukemia (CLL) (Porter et al, Science Transl. Med. 7: 303ra139 2015). LV are used to transduce CD34+ cells for autologous gene therapy of a variery of immune, blood, metabolic or neurodegenerative disorders of genetic origin (Wagemaker G. Hum Gene Ther. 2014 October; 25(10):862-5. doi: 10.1089/hum.2014). Lentiviral vectors are versatile tools that can be pseudotyped with various viral envelope glycoproteins, thereby conferring specific cellular tropism characteristics to the particles (Buchholz et al. Trends Biotechnol. 2015 December; 33(12):777-90. doi: 10.101 6/j.tibtech.2015.09.008.).

A limiting factor with the use of recombinant lentiviral particles is the capacity to obtain highly infectious titers during production of recombinant lentiviral particles. One way to circumvent this limitation is to concentrate the viral supernatant during the purification steps. However, purification protocols are difficult to establish for some LVs, depending on the envelope glycoproteins used to pseudotype viral particles. Therefore, many lentiviral vector preparations have low titer and transduction efficacy is limited.

Another limiting factor is that it is difficult to transduce primary cells, thus they must often be activated to be transduced, thereby losing their naive status.

Finally, another limiting factor is the ability of the lentiviral vector itself to infect target cells. Several envelope glycoproteins such as VSV-G or RDI114TR can be used to pseudotype lentiviral vectors and have variable infectivity on target cells such as CD34+ cells and primary blood cells.

Syncytins are endogenous retroviral virus (ERV syncytins) envelope glycoproteins which have fusogenic properties (Dupressoir et al., 2005; Lavialle et al., 2013).

Human endogenous retroviral envelope glycoprotein encoded by the ERVW-1 gene (ENSG00000242950; also known as syncytin-1 or HERV-W) has been described for its fusogenic properties in patent application EP2385058. Said application describes its use in cancer treatment, by the formation of syncytia.

Some studies have shown the possibility of pseudotyping HIV-1 virions, but not MLV-particles, with the HERV-W envelope to obtain an infectious virus capable of transducing 293T cells. However, such HERV-W particles were not stable as concentration, freezing and thawing considerably reduced titers (An et al, Journal of Virology, April 2001, p. 3488-3489). A deletion of the R intracytoplasmic region was used to increase the fusion and the pseudotype titer of HIV-1-derived gene transfer vectors (Lavillette et al 2002). The glycoprotein encoded by the ERVFRD-1 gene (ENSG00000244476; also known as syncytin-2, or HERV-FRD) was used to pseudotype SIV vectors and reportedly works as HIV or MLV pseudotype but at very low titers precluding functional studies and little information is available on the HERV-FRD HIV pseudotype (Blaise et al, Journal of Virology, January 2004, p. 1050-1054).

There is thus a need for means for improving the transduction efficiency of a virus or viral vector, particularly a stable virus or viral vector, for example for improving delivery of a gene into specific target cells. Specifically, there is a need for a virus or viral vector, which would be stable, and could thus be obtained at an industrial scale. There is also a need for a stable vector which could be used in vitro, or in vivo, as a tool presenting new biological properties. There is also a need for a process for selectively transducing cells with a virus or viral vector, so as to target in vitro, or in vivo, specific cells only. Such a virus or viral vector would have to be fully-tolerized, specific for targeted cells, and adequate for multiple administrations.

Surprisingly, the inventors have elaborated a process for obtaining lentiviral particles pseudotyped with a specific envelope glycoprotein, which are stable and which may be frozen. Said lentiviral pseudotyped particles also improve the transduction of selected target cells, in particular immune cells; this broadens the therapeutic scope of said particles. Said pseudotyped lentiviral particles are indeed efficient for transducing immune cells, and particularly B cells, T cells and dendritic cells and allow functional correction of cell deficiency. Moreover, these lentiviral pseudotyped vectors can be administered in vivo where they lead to detectable, stable and well-tolerated gene transfer in spleen and bone marrow with evidence of CD19+ spleen B cell transduction.

Thus, the use of said pseudotyped lentiviral particles is a promising strategy for patients suffering from placental dysfunction, cancers, infectious diseases, immune deficiencies, auto-immunity or for gene therapy or as vaccines or as biotechnology engineering tool.

SUMMARY OF THE INVENTION

The invention relates to a method for obtaining stable pseudotyped lentiviral particles including a heterologous gene of interest, comprising the following steps:
 a) transfecting at least one plasmid in appropriate cell lines, wherein said at least one plasmid comprises the heterologous gene of interest, the retroviral rev, gag and pol genes, and a nucleic acid coding for an ERV syncytin;
 b) incubating the transfected cells obtained in a), so that they produce the stable lentiviral particles pseudotyped with an ERV syncytin, respectively, and packaging the heterologous gene of interest; and
 c) harvesting and concentrating the stable lentiviral particles obtained in b).

The method according to the invention allows obtaining high physical titers, as well as high infectious titers, of stable pseudotyped lentiviral particles including a heterologous gene of interest.

Also provided are stable lentiviral particles pseudotyped with an ERV syncytin and packaging a heterologous gene of interest. They may be obtainable or obtained by the method described in the above paragraph. Said stable pseudotyped lentiviral particles may be useful as a medicament. Particularly, said stable pseudotyped lentiviral particles may be useful in gene therapy or in immunotherapy, particularly as a vaccine or in immunoprophylaxis.

The present invention also relates to lentiviral particles pseudotyped with an ERV syncytin including a heterologous gene of interest, preferably stable lentiviral particles pseudotyped with an ERV syncytin including a heterologous gene of interest, for use for therapy by transducing cells which express the cognate receptors such as for example ASCT2, ASCT1 or MFSD2a respectively for syncytin-1 (HERV-W) and syncytin-2 (HERV-FRD), such as human choriocarcinoma cells, human epithelial cells, or human immune cells such as B cells, T cells, or CD11c+ cells such as myeloid cells (e.g.: granulocytes, monocytes and their progenitor cells). The invention also relates to the ability to use the lentiviral particles pseudotyped with an ERV syncytin to efficiently transduce murine B cells and T cells.

The present invention also relates to lentiviral particles pseudotyped with an ERV syncytin including a gene of interest, preferably stable lentiviral particles pseudotyped with an ERV syncytin including a heterologous gene of interest, for use for treating immune deficiencies, auto-immunities, infectious diseases, placental dysfunction (such as pre-eclampsia), diseases involving the blood-brain barrier, or cancers including B cell-related cancers, or to make models of these diseases in mice.

The stable lentiviral particles pseudotyped with an ERV syncytin including a heterologous gene of interest may also be useful for the in vitro transduction of immune cells, preferably B cells or CD11c+ cells such as myeloid cells (e.g.: granulocytes, monocytes and their progenitor cells). The transduction of immune cells, preferably B cells, may find applications in biotechnology engineering, for example in the production of immunoglobulins, or in immune cell, preferably B cell engineering.

The present invention also relates to an ex vivo process for obtaining immune cells modified to express a heterologous gene of interest, comprising a step of infecting immune cells with lentiviral particles pseudotyped with an ERV syncytin including a heterologous gene of interest, preferably stable lentiviral particles pseudotyped with an ERV syncytin including a heterologous gene of interest, preferably in the presence of a LAH4 peptide or a functional derivative thereof.

The present invention also relates to the use of the stable lentiviral particles pseudotyped with an ERV syncytin including a heterologous gene of interest, preferably stable lentiviral particles pseudotyped with an ERV syncytin including a heterologous gene of interest, for biotechnology engineering. Particularly, they may be used for generating cell lines, preferably B cell lines, in order to produce a specific product, such as immunoglobulins. The stable particles of the present invention may also be used to generate models of study, particularly in mice (so as to obtain murine models). This may be useful for exploring disease mechanisms, particularly B cell diseases or B cell-mediated diseases, generating dendritic cells and/or myeloid cells expressing a product for the purpose of vaccination, or producing products with specific therapeutic effects.

According to the invention, the ERV syncytin is selected from the group consisting of HERV-W, HERV-FRD, murine syncytin-A, murine syncytin-B, syncytin-Ory1, syncytin-Car1 and syncytin-Rum1 and their functional orthologs, preferably the ERV syncytin is selected from the group consisting of HERV-W, HERV-FRD and murine syncytin-A and even more preferably the ERV syncytin is HERV-W or HERV-FRD.

DETAILED DESCRIPTION OF THE INVENTION

The inventors have surprisingly discovered that ERV syncytins which have high fusogenic properties, such as the human syncytin-1 (HERV-W), the human syncytin-2 (HERV-FRD) and the murine syncytin A, may be used for obtaining pseudotypes for recombinant HIV-1 derived lentivirus. As clearly demonstrated in the examples, the results show that it is possible to produce stable and infectious lentiviral particles comprising a gene of interest, which have selective tropism on cell lines. Surprisingly syncytin-pseudotyped lentiviral particles are able to efficiently transduce human primary B lymphocytes and CD11c+ myeloid and/or dendritic cells notably in the presence of Vectofusin-1, a cationic transduction additive.

Thus, the inventors have elaborated a method for obtaining lentiviral particles pseudotyped with an ERV syncytin, which are stable, infectious and which may be frozen. The lentiviral pseudotyped particles improve the transduction of selected target cells, in particular immune cells, and particularly B cells, T cells and dendritic cells.

The detailed embodiments of the invention are described below.

The present invention relates to a method for obtaining stable pseudotyped lentiviral particles including a heterologous gene of interest, comprising the following steps:

a) transfecting at least one plasmid in appropriate cell lines, wherein said at least one plasmid comprises the heterologous gene of interest, the retroviral rev, gag and pol genes, and a nucleic acid coding for an ERV syncytin;

b) incubating the transfected cells obtained in a), so that they produce the lentiviral particles pseudotyped with an ERV syncytin, respectively, and packaging the heterologous gene of interest; and c) harvesting and concentrating the stable lentiviral particles obtained in b).

Preferably, step c) of the method according to the invention comprises harvesting, concentrating and/or purifying the stable lentiviral particles produced in step b), from the supernatant. Thus, preferably, the concentration of step c) comprises centrifugating and/or purifying the harvested stable lentiviral particles obtained in b). Said harvest may be performed according to well-known methods in the art. Preferably, the lentiviral vectors are harvested before fusion of the transfected cells, more preferably between 20 hours and 72 hours post-transfection, preferably after 24 hours. Preferably, the harvesting step consists of a single lentivirus harvest, preferably implemented between 20 and 72 hours post-transfection, preferably between 20 and 30 hours post-transfection, more preferably after 24 hours.

ERV syncytins according to the invention refer to highly fusogenic envelope glycoproteins from eutherian mammals, which belong to the family of Endogenous Retroviruses (ERVs). These proteins are encoded by genes, which display a preferential expression in placenta and induce syncytium formation when introduced into cultured cells (Lavialle et al., 2013).

ERVs syncytins according to the invention can be selected from human syncytins (e.g.: HERV-W and HERV-FRD), murine syncytins (e.g.: syncytin-A and syncytin-B), syncytin-Ory1, syncytin-Car1, syncytin-Rum1 or their functional orthologs (Dupressoir et al., 2005; Lavialle et al., 2013).

By functional orthologs it is intended orthologs proteins encoded by orthologs genes and that exhibit fusogenic properties. Fusogenic properties may be assessed in fusion assays as described in Dupressoir et al. (PNAS 2005). Briefly, cells are transfected for example by using Lipofectamine (Invitrogen) and about 1-2 µg of DNA for $5 \times 10^5$ cells or calcium phosphate precipitation (Invitrogen, 5-20 µg of DNA for $5 \times 10^5$ cells). Plates are generally inspected for cell fusion 24-48 h after transfection. Syncytia can be visualized by using May-Grünwald and Giemsa staining (Sigma) and the fusion index calculated as $[(N-S)/T] \times 100$, where N is the number of nuclei in the syncytia, S is the number of syncytia, and T is the total number of nuclei counted.

Human syncytins encompasses HERV-W and HERV-FRD. Functional orthologs of these proteins can be found in Hominidae. HERV-W refers to a highly fusogenic membrane glycoprotein belonging to the family of Human Endogenous Retroviruses (HERVs). HERV-W is an envelope glycoprotein; it is also called Syncytin-1. It has the sequence indicated in Ensembl database, corresponding to Transcript ERVW-1-001, ENST00000493463. The corresponding cDNA has the sequence listed in SEQ ID NO:1. HERV-FRD also refers to a highly fusogenic membrane glycoprotein belonging to the family of Human Endogenous Retroviruses (HERVs). HERV-FRD is an envelope glycoprotein, also called Syncytin-2. It has the sequence indicated in Ensembl database, corresponding to Transcript ERVFRD-1, ENSG00000244476. The corresponding cDNA has the sequence listed in SEQ ID NO:2.

Murine syncytins encompasses murine syncytin-A (i.e.: *Mus musculus* syncytin-A, synA) and murine syncytin-B (i.e.: *Mus musculus* syncytin-B, synB). Functional orthologs of these proteins can be found in the Muridae family. Murine syncytin-A is encoded by the syncytin-A gene. Syncytin-A has the sequence indicated in Ensembl database Syna ENSMUSG00000085957. The corresponding cDNA has the sequence listed in SEQ ID NO:40. Murine syncytin-B is encoded by the syncytin-B gene. Syncytin-B has the sequence indicated in Ensembl databaseSynb ENSMUSG00000047977. The corresponding cDNA has the sequence listed in SEQ ID NO:41.

The syncytin-Ory1 is encoded by the syncytin-Ory1 gene. Functional orthologs of syncytin-Ory1 can be found in the Leporidae family (typically rabbit and hare).

The syncytin-Car1 is encoded by the syncytin-Car1 gene. Functional orthologs of syncytin-Car1 can be found in carnivores mammals from the Laurasiatheria superorder (Cornelis et al., 2012; Lavialle et al., 2013).

The syncytin-Rum1 is encoded by the syncytin-Rum1 gene. Functional orthologs of syncytin Rum-1 can be found in ruminant mammals.

In the various embodiments of the present invention, the ERV syncytin according to the invention can be typically selected from the group consisting of HERV-W, HERV-FRD, syncytin-A, syncytin-B, syncytin-Ory1, syncytin-Car1 and syncytin-Rum1 and their functional orthologs; preferably the ERV syncytin is selected from the group consisting of HERV-W, HERV-FRD, murine syncytin-A and their functional orthologs, more preferably the ERV syncytin is selected from the group consisting of HERV-W, HERV-FRD and murine syncytin-A and even more preferably the ERV syncytin is HERV-W or HERV-FRD.

The method according to the invention allows obtaining high physical titers, as well as high infectious titers, of stable pseudotyped lentiviral particles including a heterologous gene of interest. Indeed, the stable pseudotyped lentiviral particles including a heterologous gene of interest are obtained at a high physical titer thanks to the method of the invention, and are infectious, thus efficient, particularly for transducing B cells, or myeloid cells.

By "physical titer", it is meant the number of lentiviral particles which are produced. The physical titer may be measured according to classical methods known in the art, and which are commonly used to quantify lentiviral particles, for example by p24 ELISA, which is illustrated in the examples, by direct particle counting with an automated counter such as the Nanosight NS300 instrument from Malvern using the manufacturer's instructions, by RT (reverse transcriptase) ELISA (as described in Circ et al, Plosone, July 2014, Vol. 9, Issue 7, Immunization of mice with lentiviral vectors targeted to MHC class II+ cells is due to preferential transduction of dendritic cells in vivo) or by viral RNA RT-qPCR.

By "high physical titer", it is meant a titer of particles produced at the end of step b) higher than 200 ng p24/mL, preferably higher than 210 ng p24/mL, even more preferably higher than 300 ng p24/mL. More preferably, the physical titer of particles pseudotyped with an ERV syncytin such as HERV-W, produced at the end of step b) is higher than 300 ng p24/mL, preferably higher than 400 ng p24/mL. More preferably, the physical titer of particles pseudotyped with an ERV syncytin such as HERV-FRD, produced at the end of step b) is higher than 210 ng p24/mL, preferably higher than 300 ng p24/mL.

By "high physical titer", it is also meant a titer of particles produced at the end of step c) (i.e. concentrated) higher than $1 \times 10^5$ ng p24/mL, preferably higher than $1.1 \times 10^5$ ng p24/mL, more preferably higher than $1.5 \times 10^5$ ng p24/mL More preferably, the physical titer of particles pseudotyped with an ERV syncytin such as HERV-W produced at the end of step c) is higher than $2.2 \times 10^5$ ng p24/mL, preferably higher than $3.0 \times 10^5$ ng p24/mL, even preferably higher than $4.0 \times 10^5$ ng p24/mL. More preferably, the physical titer of particles pseudotyped with an ERV syncytin such as HERV-FRD produced at the end of step c) is higher than $1.1 \times 10^5$ ng p24/mL, preferably higher than $1.5 \times 10'$ ng p24/mL.

According to Farson el al., (Hum. Gene Ther. 2001) one can assume that 1 femtogram (fg) of p24 corresponds to 12 physical particles (pp) of lentivirus. Without wishing to be bound by theory, the inventors believe that this calculated number of physical particles obtained based on p24 is slightly overestimated as compared to a value obtained by direct particle counting with an automated counter (such as the Nanosight NS300 instrument), because p24 alone is also taken into account. Generally it can be estimated that there is on average about 4 times more particles calculated with p24 ELISA than particles measured with the automated counter (see Supplementary Table S6 in Example 3 below). Thus a physical titer higher than $1 \times 10^5$ ng p24/mL corresponds to a physical titer higher than $1.2 \times 10^{12}$ calculated physical particles (pp)/mL or higher than about $3 \times 10^{11}$ pp/mL, as measured by Nanosight counting.

By "infectious titer", it is meant the number of functional lentiviral particles. The infectious titer may be measured according to classical methods known in the art, for example by flow cytometry to calculate a transducing units titer (TU/mL) or by qPCR to measure infectious genomes (ig/mL), which are illustrated in the examples. A publication describing such a method is Kutner R H, Zhang X Y, Reiser J (2009). Production, concentration and titration of pseudotyped HIV-1-based lentiviral vectors. *Nature protocols* 4: 495-505. The infectious titer of the lentiviral particles of the invention is measured upon infection of a permissive cell line, preferably 293T cells, or another permissive cell such as A20 cells, more preferably using the titration method described herein into the experimental example section of the application.

By "high infectious titer", it is meant a titer of infectious particles produced at the end of step c), higher than 2 E+04 TU/ml, preferably higher than 1 E+05 TU/ml, more preferably higher than 1 E+06 TU/ml, even more preferably higher than 2 E+06 TU/ml. More preferably, the infectious titer of particles pseudotyped with HERV-W produced at the end of step c), is higher than 1,2 E+05 TU/ml, preferably higher than 2 E+05 TU/ml, more preferably higher than 1 E+06 TU/ml, even more preferably higher than 1.5 E+06 TU/ml. More preferably, the infectious titer of particles pseudotyped with HERV-FRD produced at the end of step c), is higher than 2 E+04 TU/ml, preferably higher than 2 E+05 TU/ml, more preferably higher than 1 E+06 TU/ml, even more preferably higher than 2.5 E+06 TU/ml. Preferably such high infectious titers are measured using 293T cell infection and the titration method described in the example herein.

The present invention also relates to stable lentiviral particles pseudotyped with HERV-W or HERV-FRD and packaging a heterologous gene of interest. That may be obtainable, or obtained, by the above method.

By "stable", it is meant that the infectious titer of the stable lentiviral particles pseudotyped with an ERV syncytin, such as an ERV syncytin as previously defined and more preferentially pseudotyped with HERV-W, HERV-FRD or the murine syncytin-A and packaging a heterologous gene of interest of the invention, and having infected 293T cells or another permissive cell line for instance A20 cells, has been divided at most by 10 between two consecutive time points. The two consecutive time points may represent a duration of a few weeks, such as 1 to 3 weeks. The two consecutive time points may also represent a duration of a few months, such as 1, 2 or 3 months, or 6, 9, 10 months or even 12 or 18 months. The lentiviral pseudotyped particles according to the invention may be frozen, they keep their stability properties. They are indeed resistant to very low temperature treatments, such as freezing or cryopreservation. They may also be resistant to medium temperature treatments: as soon as they present the stability properties as indicated above, they correspond to the present invention.

Such lentiviral pseudotyped particles can thus be centrifugated and/or frozen, while maintaining their fusogenic and infectious properties, as well as their ability to deliver the gene of interest to the target cells, particularly in vivo. Again, the stable pseudotyped lentiviral particles packaging a heterologous gene of interest according to the invention present a high physical titer, as well as a high infectious titer.

By "heterologous" gene, it is meant a gene, which comes from an organism different from the one of the retroviral rev, gag and pol genes.

By "gene of interest", it is meant a functional version of a gene. The functional version means the wild-type version of said gene, a variant gene belonging to the same family, or a truncated version, which preserves the functionality of the encoded protein.

The gene of interest may be derived from a gene, which is deficient or non-functional in a patient, or a gene coding for an immunogenic protein (such as a viral protein, a bacterial protein or a tumor antigen). The heterologous gene of interest may also be a reporter gene (useful for diagnosis purpose, and for identifying ligands of a target protein), a suicide gene, or a gene coding for a therapeutic RNA (ie coding for an antisense RNA complementary to a target DNA or RNA sequence, or a gRNA, a RNAi such as shRNA). The gene of interest is able to produce the encoded protein, peptide or RNA.

By «pseudotype», it is meant a lentiviral particle comprising:
  an envelope glycoprotein derived from a virus, said virus being different from the one from which said lentiviral particle is derived;
  a modified envelope glycoprotein. In such a case, the native viral envelope glycoprotein may be modified by mutation or by any other amino acid modification; or
  a chimeric glycoprotein. Such a glycoprotein is a fusion protein between at least a part of the viral glycoprotein, and another sequence.

In step a), appropriate cell lines are transfected with at least one plasmid. Preferably, the transfection is a transient transfection.

Preferably, appropriate cell lines are transfected with at least one, two, three or four plasmids. These cell types include any eukaryotic cell which support the lentivirus life cycle.

Preferably, the appropriate cell lines are stable cell lines or cell lines refractory to the catastrophic consequences of the fusogenic effects of syncytins, so as to continue growing while producing the particles. Said appropriate cell lines are mammalian cell lines, preferably human cell lines. Representative examples of such cells include Human Embryonic Kidney (HEK) 293 cells and derivatives thereof, HEK293 T cells, as well as subsets of cells selected for their ability to grow as adherent cells, or adapted to grow in suspension under serum-free conditions. Such cells are highly transfectable.

In one embodiment, the appropriate cell lines are already expressing at least one, and at most four of the five sequences which are the heterologous gene of interest, the retroviral rev, gag and pol genes, and the nucleic acid coding for an ERV syncytin such as HERV-W, HERV-FRD or murine syncytinA, preferably in inducible form. In such a case, step a) comprises transfecting said cell line with at least one plasmid comprising at least one sequence which is not already expressed in said cell line. The plasmid mixture, or the single plasmid (if only one plasmid is used) is chosen such that, when transfected into said cell lines in step a), said cell lines express all five above sequences.

For example, if the appropriate cell line expresses the retroviral rev, gag and pol genes, then the plasmid or mixture of plasmids to be transfected comprises the remaining sequences to be expressed, i.e. the heterologous gene of interest and the nucleic acid coding for an ERV syncytin such as HERV-W, HERV-FRD or murine syncytinA.

When one single plasmid is used, it comprises all the 5 sequences of interest, i.e.:
  the heterologous gene of interest,
  the rev, gag and pol genes, and
  a nucleic acid coding for an ERV syncytin as previously described and notably coding for HERV-W, HERV-FRD or the murine syncytinA.

When two or three plasmids are used (plasmid mixture), each of them comprises some of the sequences of interest listed in the previous paragraph, so that the plasmid mixture comprises all the above cited sequences of interest.

Preferably four plasmids are used, and the quadritransfection comprises the following:
the first plasmid comprises the gene of interest,
the second plasmid comprises the rev gene,
the third plasmid comprises the gag and pol genes, and
the fourth plasmid comprises a nucleic acid coding for an ERV syncytin as previously described and notably coding for HERV-W, HERV-FRD or the murine syncytin-A.

Said quadritransfection is preferably performed with specific ratios between the four plasmids. The molar ratio between the different plasmids can be adapted for optimizing the scale-up of the production. The person skilled in the art is able to adapt this parameter to the specific plasmids he uses for producing the lentivirus of interest. In particular, the weight ratios of the first, second, third, fourth plasmids are preferably (0.8-1.2):(0.1-0.4); (0.5-0.8):(0.8-1.2), more preferably around 1:0.25:0.65:1.

The rev, gag and pol genes are retroviral, preferably lentiviral. Preferably, they are HIV genes, preferably HIV-1 genes, but could be also EIAV (Equine Infectious Anemia Virus), SIV (Simian immunodeficiency Virus), Foamy Virus, or MLV (Murine Leukemia Virus) virus genes.

The nucleic acid coding for the ERV syncytin, such as an ERV syncytin as previously defined and more preferentially coding for HERV-W, HERV-FRD or the murine syncytin-A is a DNA or cDNA sequence. Preferably, it corresponds to the cDNA sequence respectively listed in SEQ ID NO:1, 2 or 40, or to a sequence presenting at least 80%, preferably at least 90%, more preferably at least 95%, more preferably at least 99% identity with such SEQ ID NO:1, 2, or 40 respectively. Preferably, step a) comprises the transfection of at least the plasmid comprising, preferably consisting of, the cDNA sequence listed in SEQ ID NO:3 or 4.

The term "identity" refers to the sequence similarity between two polypeptide molecules or between two nucleic acid molecule. When a position in both compared sequences is occupied by the same base or same amino acid residue, then the respective molecules are identical at that position. The percentage of identity between two sequences corresponds to the number of matching positions shared by the two sequences divided by the number of positions compared and multiplied by 100. Generally, a comparison is made when two sequences are aligned to give maximum identity. The identity may be calculated by alignment using, for example, the GCG (Genetics Computer Group, Program Manual for the GCG Package, Version 7, Madison, Wis.) pileup program, or any of sequence comparison algorithms such as BLAST, FASTA or CLUSTALW.

The plasmids encoding the envelope glycoproteins which may be used are known to those skilled in the art such as the commercially available pCDNA3, backbone or any other plasmid cassette using a similar expression system, for instance using the CMV promoter such as the pKG plasmid described in Merten et al. (Hum Gene Ther., 2011).

According to step a), various techniques known in the art may be employed for introducing nucleic acid molecules into cells. Such techniques include chemical-facilitated transfection using compounds such as calcium phosphate, cationic lipids, cationic polymers, liposome-mediated transfection, such as cationic liposome like Lipofectamine (Lipofectamine 2000 or 3000), polyethyleneimine (PEI), non-chemical methods such as electroporation, particle bombardment or microinjection.

According to a preferred embodiment of the invention, the transfection of step a) is carried out using calcium phosphate.

Typically, step a) may be performed by transient transfection of 293T cells with 4 plasmids (quadritransfection), in the presence of calcium phosphate. The 4 plasmids are preferably: a pKL plasmid expressing the HIV-1 gag and pol genes, a pK plasmid expressing HIV-1 rev gene, a pCCL plasmid expressing the heterologous gene of interest under control of a cellular promoter such as the human phosphoglycerate kinase (PGK) promoter and a pCDNA3 plasmid expressing an ERV syncytin, such as an ERV syncytin as previously defined and more preferentially expressing HERV-W (Syncytin-1), HERV-FRD (Syncytin-2) or the murine syncytin-A glycoproteins from a CMV promoter.

Then, after step a), the method according to the present invention comprises a step b) of incubating the transfected cells obtained in a), so that they produce, preferably in the supernatant, the lentiviral particles pseudotyped with an ERV syncytin, such as an ERV syncytin as previously defined and more preferentially pseudotyped with HERV-W, HERV-FRD or the murine syncytin-A including the heterologous gene of interest. Indeed, once step a) is performed, incubation of the obtained cells is performed. This leads to the production in the supernatant of the stable lentiviral particles, which are pseudotyped with an ERV syncytin, such as an ERV syncytin as previously defined and more preferentially pseudotyped with HERV-W, HERV-FRD or the murine syncytin-A and which include the heterologous gene of interest.

After transfection, the transfected cells are thus allowed to grow for a time which may be comprised between 20 and 72 hours post-transfection, in particular after 24 hours.

In a particular embodiment, the medium used for culturing the cells is a classical medium, such as DMEM, comprising a sugar, such as glucose. Preferably, the medium is a serum-free medium. Culture may be carried out in a number of culture devices such as multistack systems or bioreactors adapted to the culture of cells in suspension. The bioreactor may be a single-use (disposable) or reusable bioreactor. The bioreactor may for example be selected from culture vessels or bags and tank reactors. Non-limiting representative bioreactors include a glass bioreactor (e.g. B-DCU® 2L-10L, Sartorius), a single-use bioreactor utilizing rocking motion agitation such as wave bioreactor (e.g. Cultibag RM® 10L-25L, Sartorius), single use stirrer tank bioreactor (Cultibag STR® 50L, Sartorius), or stainless steel tank bioreactor.

After incubation, the obtained stable lentiviral particles are harvested and concentrated; this is step c). Preferably, the stable lentiviral particles obtained in b) are harvested before fusion of the transfected cells, more preferably 24 h post-transfection. Preferably, the stable lentiviral particles present in the supernatant obtained in b) are centrifugated and/or purified. Said concentration step c) may be performed by any known method in the art, such as by centrifugation, ultrafiltration/diafiltration and/or chromatography.

According to one embodiment, the supernatant is centrifugated at a speed comprised between 40000 and 60000 g, during 1 h to 3 h, at a temperature comprised between 1° C. and 5° C., so as to obtain a centrifugate of stable pseudotyped viral particles.

Preferably, the centrifugation is performed at a speed of 45000 to 55000 g, during 1 h30 to 2 h30, at a temperature of 2° C. to 5° C., preferably around 4° C. At the end of this step, the particles are concentrated in the form of a centrifugate, which may be used.

According to another embodiment, step c) is a chromatography, such as an anion exchange chromatography, or an affinity chromatography. The anion exchange chromatography may be preceded or followed by a step of ultrafiltration, in particular an ultrafiltration/diafiltration, including tangential flow filtration. The anion exchange chromatography is for example a weak anion exchange chromatography (including DEAE (D)-diethylaminoethyl, PI-polyethylenimine).

This method allows obtaining lentiviral particles pseudotyped with an ERV syncytin, such as an ERV syncytin as previously defined and more preferentially pseudotyped with HERV-W, HERV-FRD or the murine syncytin-A. Said particles are stable, because, thanks to the above method, they can be concentrated without being degraded, as shown in the examples. Moreover, said particles comprise the heterologous gene of interest.

Preferably, the stable lentiviral particles pseudotyped with an ERV syncytin, such as an ERV syncytin as previously defined and more preferentially pseudotyped with HERV-W, HERV-FRD or the murine syncytin-A and packaging the gene of interest according to the invention, are suspended in a pharmaceutically acceptable carrier, so as to obtain a pharmaceutical composition.

A "pharmaceutically acceptable carrier" refers to a vehicle that does not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type. Preferably, the pharmaceutical composition contains vehicles, which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The pharmaceutical forms suitable for injectable use include sterile aqueous solutions or suspensions. The solution or suspension may comprise additives which are compatible with enveloped viruses and do not prevent virus entry into target cells. In all cases, the form must be sterile and must be fluid to the extent that easy syringability exists. It must be stable under the conditions of manufacture and storage and must be preserved against the contaminating action of microorganisms, such as bacteria and fungi. An example of an appropriate solution is a buffer, such as phosphate buffered saline (PBS).

The stable pseudotyped lentiviral particles of the invention, as they package the heterologous gene of interest, may be used as a medicament.

Indeed, the results provided in the present application clearly demonstrate that a syncytin-pseudotyped lentiviral vector of the invention can be used in immunotherapy in humans and can functionally correct B cells in a human disease. Furthermore, the syncytin-pseudotyped vectors of the invention are able to target B cells in vivo. The data showed herein illustrated that these new tools are very well tolerated in vivo as gene transfer is observed for a long period of time. For in vivo applications, efficient transduction of the target cells (such as B cells) can be obtained without the need of vectofusin 1.

Thus, the stable pseudotyped lentiviral particles may be used in gene therapy or immunotherapy or as a vaccine or in immunoprophylaxis.

Gene therapy can be performed by gene transfer, gene editing, exon skipping, RNA-interference, trans-splicing or any other genetic modification of any coding or regulatory sequences in the cell, including those included in the nucleus, mitochondria or as commensal DNA (viral sequences contained in cells).

The two main types of gene therapy are the following:
- a therapy aiming the replacement of a deficient/abnormal gene: this is replacement gene therapy;
- a therapy aiming gene editing: in such a case, the purpose is to provide to a cell the necessary tools so that the gene of interest is expressed: this is gene editing therapy.

In replacement gene therapy, the gene of interest may be a correct version of a gene which is deficient or mutated in a patient, as is the case for example in a genetic disease. In such a case, the gene of interest will restore the expression of the deficient or mutated gene. Of particular interest are deficient or mutated genes in patients exhibiting a disease which, once corrected in immune cells, preferably in B cells, T cells, monocytes or dendritic cells, more preferably in B cells, improve the patient's disease or symptoms. Examples of mutated genes in genetically defective B cells are the following:
- the gene coding the gamma chain in X-linked severe combined immunodeficiency disease (SCID-X1) (the patients have a T-NK-B+ phenotype), or for SCID-X1 patients already treated by gene therapy but in whom B cell correction was not induced;
- the gene TNFRSFI3B encoding the TACI (transmembrane activator and calcium-modulator and cyclophilin-ligand interactor) which is mutated in common variable immunodeficiency (CVID);
- the CD19 or BAFFR gene which may be mutated in common variable immunodeficiency (CVID);
- any of the genes responsible for hyper-immunoglobulin M, notably caused by mutations in the gene coding for CD40;
- the WAS gene which is mutated in Wiskott-Aldrich syndrome, including WAS patients already treated by stem cell-based gene therapy and in whom B cell correction is incomplete;
- the Fanc genes, which are mutated in either of the Fanconi anemia subtype, for instance FancA or FancC;
- any of the genes responsible for hyperimmunoglobulin E.

Thus, these genes could be used as the gene of interest.

Examples of mutated genes in genetic diseases of phagocyte function, in particular those which lead to the production of non-functional or abnormal monocytes or dendritic cells and which could be treated by expressing or correcting the causal gene in said monocytes or dendritic cells, are the following: Wiskott Aldrich Syndrome (WAS gene), chronic granulomatous disease (CGD, CYBB or p47 genes), leukocyte adhesion deficiency (LAD), IL-12/23 deficiency (IL12 p40, p70, IL23 chains), bare lymphocyte syndrome due to absent HLA molecules, auto-inflammatory disorders such as familial Mediterranean fever (pyrin gene) or cryopyrin-related diseases (NALP3 mutations).

Replacement gene therapy could also be used to treat cancer. Genes of interest in cancer could regulate the cell cycle or the metabolism and migration of the tumor cells, or induce tumor cell death. For instance, inducible caspase-9 could be expressed in B cell leukemias or B cell lymphomas to trigger cell death, preferably in combination therapy to elicit durable anti-tumor immune responses.

Diseases involving cells expressing the receptors for ERV syncytin such as syncytin-1 or syncytin-2 could also be treated by gene transfer into these cells. For example, one can quote gestational pathologies in which placental cells could be treated; cancer such as leukemias, lymphomas or solid tumor cells (including breast or lung tumor cells known to express ASCT2 or MFSD2a) in which the malignant cells could be treated; neurological conditions in which endothelial cells of the blood-brain-barrier could be treated; or any genetic or acquired condition implicating these cells.

In gene therapy, it might be possible to use the stable pseudotyped lentiviral particles of the invention in therapy for immune cell engineering, preferably B cell engineering, by transducing said immune cells. It might be possible to generate regulatory B cells by expressing immunosuppressive proteins in B cells, for instance IL-10, or to induce the production of immunoregulatory proteins such as antibodies or fusion proteins.

It could also be possible to insert sequences favoring gene splicing, expression or regulation or gene editing. Tools such as CRISPR/Cas9 may be used for this purpose. This could be used to modify gene expression in B cells, in the case of auto-immunity or cancer, or to perturb the cycle of viruses in B cells. In such cases, preferably, the heterologous gene of interest is chosen from gRNA, nucleases, DNA templates and RNAi components, such as shRNA.

A specific example of gene editing would be the treatment of WaldenstrÖm macroglobulinemia: in such a disease, a point mutation (L265P) of (MYD88) has been observed in B cells of 80-88% of the patients and contributes to the survival and persistence of these tumor cells. Thus, by gene editing a correct version of this gene in afflicted patients, this may contribute to effective therapies against this disease.

The stable pseudotyped lentiviral particles of the invention could be used together or sequentially to target the same cells through different receptors. This could be an advantage in strategies such as gene editing, in which multiple components of the gene editing platform need to be added to the cells.

In gene editing therapy, it might also be possible to transduce immune cells, preferably B cells, with the stable pseudotyped lentiviral particles of the invention. Preferably then, if the heterologous gene of interest codes for an immunoglobulin, then transduced B cells are able to produce the corresponding immunoglobulins. An example would be to engineer a known sequence of variable immunoglobulin regions which confers specific recognition of pathogens such as viruses (rabies, HIV, Ebola, Flu, CMV, Zika) or parasites (*T. cruzi, P. falciparum*) which could be used for prophylactic or therapeutic use or for diagnostic.

When the transduced immune cells are macrophages, then the therapy may be an anti-inflammatory therapy, tolerance induction or a vaccination.

When the transduced immune cells are B cells, then the therapy may be for treating an autoimmune disease.

When the transduced immune cells are dendritic cells, then the therapy may be as vaccine.

For example, recipient immature dendritic cells transduced with major or minor histocompatibility antigens specific of an allogeneic organ donor may be used to induce allogeneic organ transplant tolerance in the recipient.

Again, immunotherapy applications via genetic engineering of antigen-presenting cells such as human B cells, human myeloid dendritic cells or monocytes, may be found by introducing into these cells a recombinant gene expression cassette containing an antigenic sequence associated or not with immunommodulatory sequences, for antigenic presentation for the purpose of vaccination to protect against infectious diseases; for treating cancer; or for the purpose of inducing cell-specific or antigen-specific immune tolerance, in order to treat diseases with inflammatory immune components, such as diabetes or Alzheimer's disease, or to facilitate organ or bone marrow transplantation.

In gene therapy, the targeted tissue is not only immune cells, but could also be placenta as well as any tissue in which syncytin-mediated heterologous fusion occurs, or any tissue or any cell expressing the receptors for syncytin. Examples include possibilities of treating placenta to prevent pre-eclampsia. Pre-eclampsia is a leading cause of maternal mortality and some studies have detected in the pre-eclamptic placenta that differentially expressed microRNAs deregulate TGF-β2 response (Zhou et al Sci Rep. 2016 Jan. 29; 6:19910. doi: 10.1038/srep19910.). Possibly, gene transfer or gene editing in placental cells through the use of syncytin-pseudotyped vectors may correct this problem. Possibly the target tissue could be skeletal muscle as it was recently shown that syncytins are expressed in myoblasts and may contribute to fusion between myoblasts (Frese et al., 2015). Possibly, syncytin-pseudotyped vectors which may recognize receptor on skeletal muscle cells, may be used for muscle gene therapy.

As used herein, the term "patient" denotes a mammal. Preferably, a patient according to the invention is a human.

An immune cell is a cell involved in the immune system. It comprises notably B cells, T cells, NK cells, macrophages and dendritic cells.

A B cell (or B lymphocyte) is an immune cell responsible for the production of antibodies, and involved in the humoral immune response.

A dendritic cell is an immune cell, which is accessory: it is an antigen-presenting cell. Its main function is to process the antigen material and present it on its cell surface to the T cells.

A T cell (or T lymphocyte) is an immune cell involved in cell-mediated immune response. It may be chosen from killer T cells, helper T cells and gamma delta T cells.

The stable pseudotyped lentiviral particles may be used in immunotherapy or as a vaccine or in immunoprophylaxis. In such a case, the heterologous gene of interest may code for an immunogenic protein, such as a viral protein, a bacterial protein or a tumor antigen. In such a case, the expression of the gene will stimulate immune responses, allowing immunization. This corresponds to a vaccine. In immunoprophylaxis, the heterologous gene of interest may code for a protein which prevents B cell viral infection, such as EBV infection, which may cause malignant transformation in immunodeficient patients.

Thus, the invention also relates to the use of stable lentiviral particles pseudotyped with an ERV syncytin, such as an ERV syncytin as previously defined and more preferentially pseudotyped with HERV-W, HERV-FRD or the murine syncytin-A packaging a heterologous gene of interest, for therapy by transducing immune cells, preferably B cells.

The invention also relates to the use of stable lentiviral particles pseudotyped with an ERV syncytin, such as an ERV syncytin as previously defined and more preferentially pseudotyped with HERV-W, HERV-FRD or the murine syncytin-A packaging a heterologous gene of interest, for bioengineering in human B cells. For instance, one can quote the production of vectored antibodies in B cells which consists of expressing by gene transfer in human B cells recombinant antibodies directed against toxins, pathogens (such as HIV-1) or parasites (such as *Plasmodium*) to facilitate the rapid recognition and neutralization of these pathogens. Examples of recombinant antibodies that are vectored in mice in a different system are described in "Balazs A B, et al. Nat Med. 2014 March; 20(3):296-300. doi: 10.1038/nm" or "Deal C et al. Proc Natl Acad Sci USA. 2014 Aug. 26; 111(34):12528-32. doi: 10.1073/pnas. 1407362111".

Bioengineering in human B cells could also consist of using gene transfer to immortalize the antigen-responsive human B cells (for instance CD27+ germinal center B cells) with genes such as anti-apoptotic genes, or B cell oncogenes (such as Bcl6 or BclX), for the purpose of growing such cells responding to a pathogen and selecting their antibody sequences, as is described in "Kwakkenbos M J et al. Nat Med. 2010 January; 16(1):123-8. doi: 10.1038/nm.2071. Generation of stable monoclonal antibody-producing B cell receptor-positive human memory B cells by genetic programming".

Said lentiviral particles pseudotyped with an ERV syncytin, such as an ERV syncytin as previously defined and more preferentially pseudotyped with HERV-W, HERV-FRD or the murine syncytin-A, packaging a heterologous gene of interest, may be administered to a patient per se, for example by injection. In such a case, the transduction of immune cells will be made in vivo. In another alternative, a sample of immune cells, preferably B cells, or their precursors, of a patient is previously taken, then said lentiviral particles are injected into the immune cells or their precursors of the sample (i.e. thus in vitro), and the treated sample is finally re-administered to the patient. In this latter case, the sample of immune cells or their precursors infected with said lentiviral particles, and thus comprising the heterologous gene of interest, is the medicament. Thus, the invention also aims the use of a sample of immune cells or their precursors infected with said lentiviral particles in therapy, or for a diagnosis purpose (in case the heterologous gene of interest is a reporter gene).

The invention also relates to the use of lentiviral particles pseudotyped with HERV-W or HERV-FRD including a heterologous gene of interest, for treating immune deficiencies, auto-immunities, infectious diseases or B cell-related cancers.

By "immune deficiencies", it is meant a condition leading to increased number or severity of microbial (bacterial, viral, parasitic) infections or reducing the anti-tumor surveillance and leading to increased frequency of cancers.

For this purpose, the heterologous gene of interest may be a suicide gene, a "dominant-negative" gene, a gene coding for an antibody which would block target cell activation, a gene coding for a protein correcting the expression of an oncogene, or a gene coding for a protein reducing or altering the viral cycle of a transformant virus for B cells (such as EBV in case of Burkitt's syndrome).

By "auto-immunities", it is a meant autoimmune diseases. They correspond to conditions involving an abnormal immune response of the body against healthy cells of said body. Auto-immunities may be confined to an organ or a tissue. Autoimmune diseases, in particular autoimmune diseases susceptible to be treated by B cell-depleting strategies (i.e. rituximab) and which could be treated by expressing a gene in the pathological B cells with the intention of killing them (such as caspase 9 or inducible caspase 9, thymidine kinase, or any other "suicide gene"), or with the intention of immunomodulating their function by expressing immunoregulatory genes such as IL-10, are for instance: rheumatoid arthritis, systemic lupus erythematosus, idiopathic thrombocytopenic purpura, anti-neutrophil cytoplasmic antibody associated vasculitis (ANCA vasculitis), Grave's disease, systemic sclerosis, autoimmune hemolytic anemia, pemphigus vulgaris, cold agglutinin disease, Sjogren's syndrome, thrombotic thrombocytopenic purpura, cryoglobulinemia, IgM mediated neuropathy, multiple sclerosis, neuromyelitis optica, idiopathic membranous nephropathy, dermatomyositis, autoimmune neurological disorders, hemophilia A, or organ transplantation (kidney) complications by organ rejection or bone marrow transplantation complications caused by graft versus host disease.

By "infectious diseases", it is meant diseases which are caused by pathogenic microorganisms, such as bacteria, viruses, parasites or fungi; the diseases can be spread, directly or indirectly, from one person to another. Bacterial infections may be due to *Streptococcus, Staphylococcus* and *E. coli*. Viral infections may be due to Papillomaviridae, Polyomaviridae (BK virus, JC virus), Herpesviridae (Herpes simplex type 1 or 2, Varicella-zoster virus, Epstein-Barr virus, cytomegalovirus), Poxviridae (smallpox), Hepadnaviridae (hepatitis B), Parvoviridae (parvovirus B19), Caliciviridae (Norwalk virus), Picomaviridae (coxsakievirus, hepatitis A virus, poliovirus, rhinovirus), Coronoviridae (severe acute respiratory syndrome virus), Flaviviridae (hepatitis C virus, yellow fever virus, dengue virus, West Nile virus, TBE virus, Zika Virus), Retroviridae (HIV), Filoviridae (Ebola virus, Marburg virus), Orthomyxoviridae (Influenza virus), Paramyxoviridae (Measles virus, Mumps virus, respiratory syncytial virus) and Rhabdoviridae (rabies virus). Parasitic infections may be due to protozoan organisms (such as *Plasmodium* spp), helminths organisms or ectoparasites. Fungal infections may be due to *Tinea versicolor*, dermatophytes (*Microsponrum, Trichophylon, Epidermophyton*) or *Candida albicans*.

As used herein, the term "B cell-related cancer" refers to the pathological condition in mammals that is typically characterized by unregulated cell growth of B cells. B cell malignancies may be acute lymphoid leukemia, chronic lymphocytic leukemia, multiple myeloma, Waldenstrtm macroglobulinemia or any type of B cell lymphoma including opsoclonus myoclonus and any type of virus-induced B cell pathology such as those caused by Epstein-Barr-Virus, in which a therapeutic effect could be obtained by gene transfer of a cell cycle modulator or anti-oncogenic gene sequence (such as p53, antisense sequence to an oncogene, shRNA against an oncogene) or a suicide gene (such as icasp9, thymidine kinase) or anti-viral sequences, or any genetic sequence susceptible to arrest the growth, the spreading or the production of pathological molecules by the tumor cells, including sequences for gene editing when specific gene mutations are present, such as mutations in MyD88 in the case of Waldenstrm hyperglobulinemia, or sequences to edit critical viral life cycle genes, or sequences that will activate an anti-tumor immune response or any combination of these approaches.

In the context of the invention, the term "treating" or "treatment", as used herein, means reversing, alleviating or inhibiting the progress of the disorder or condition to which such term applies, or reversing, alleviating or inhibiting the progress of one or more symptoms of the disorder or condition to which such term applies.

Finally, the present invention relates to an ex vivo process for obtaining immune cells modified to express a heterologous gene of interest, comprising a step of infecting immune cells with stable lentiviral particles pseudotyped with an ERV syncytin as previously described and notably pseudotyped with HERV-W, HERV-FRD or the murine syncytin-A packaging a gene of interest, in the presence of a LAH4 peptide or a functional derivative thereof, preferably vectofusin-1.

Preferably, the immune cells are chosen from B cells, T cells, dendritic cells and macrophages.

Preferably, the immune cells are naive. According to the preferred embodiment, the naïve immune cells are not previously stimulated.

According to another embodiment, when stimulation is used, the stimulation step is minimal and performed by incubating naïve immune cells in a medium comprising IL-7 so as to preserve the survival of naïve B cells.

Thus, preferably, the ex vivo process for obtaining immune cells modified to express a heterologous gene of interest according to the invention, comprises a step of directly infecting naïve immune cells, especially naïve B cells, with stable lentiviral particles pseudotyped with an ERV syncytin as previously described and notably pseudotyped with HERV-W, HERV-FRD, or the murine syncytin-A packaging a heterologous gene of interest, in the presence of a LAH4 peptide or a functional derivative thereof. Said naïve immune cells are not previously stimulated. The present invention also relates to the naïve immune cells, preferably naïve B cells, comprising the heterologous gene of interest obtainable by said ex vivo process.

According to another embodiment, the ex vivo process for obtaining immune cells modified to express a heterologous gene of interest according to the invention, may also comprise the following steps:
- optionally stimulating naïve immune cells by incubating them in a medium comprising IL-7, and then
- infecting the naïve immune cells, stimulated or not, with lentiviral particles pseudotyped with an ERV syncytin as previously described and notably pseudotyped with HERV-W, HERV-FRD or the murine syncytin-A including a gene of interest, in the presence of a LAH4 peptide or a functional derivative thereof. The present invention also relates to the naïve immune cells previously stimulated obtainable by said ex vivo process.

Preferably, the LAH4 peptide or functional derivative thereof, preferably vectofusin-1, is present notably at a concentration of 7 to 20 μg/ml, more preferably of 10 to 15 μg/ml.

In the context of the present invention, the "LAH4 peptide" refers to the peptide with the amino acid sequence consisting of SEQ ID NO: 5. As used herein, the term "LAH4 functional derivative" means any peptide whose sequence has been designed based on the primary structure of the LAH4 peptide and having the ability to improve the transduction efficiency of a virus or viral vector. In particular embodiment, a LAH4 functional derivative is a peptide having the ability to improve the transduction efficiency of a virus encapsidated with a an ERV syncytin as previously described and notably encapsidated with HERV-W, HERV-FRD or the murine syncytin-A envelope in eukaryotic cells, in particular human, mouse, rat, monkey, dog or hamster cells, in particular a human CD34+ cell.

The LAH4 peptide or a functional derivative thereof may be selected among the sequences represented in SEQ ID NO: 5 to 31:

```
LAH4:
KKALLALALHHLAHLALHLALALKKA    (SEQ ID NO: 5)

LAH4-L1:
KKALLAHALHLLALLALHLAHALKKA    (SEQ ID NO: 6)

LAH4-L1-dKC:
KKALLAHALHLLALLALHLAHALA      (SEQ ID NO: 7)

LAH4-L1-R:
RRALLAHALHLLALLALHLAHALRRA    (SEQ ID NO: 8)

LAH4-L0:
KKALLAHALAHLALLALHLALHLKKA    (SEQ ID NO: 9)

LAH4-L2:
KKALLALALHHLALLALHLAHALKKA    (SEQ ID NO: 10)

LAH4-L3:
KKALLALALHHLALLAHHLALALKKA    (SEQ ID NO: 11)

LAH4-L4iso:
KKALLHLALLHAALLAHHLALALKKA    (SEQ ID NO: 12)

LAH4-L5:
KKALLHLALLHAALLAHLAALHLKKA    (SEQ ID NO: 13)

LAH4-L6iso:
KKALLHLALLLAALHAHLAALHLKKA    (SEQ ID NO: 14)

LAH4-A1:
KKALLAHALHLLAALALHLAHLLKKA    (SEQ ID NO: 15)

LAH4-A2:
KKALLLAALHHLAALALHLAHLLKKA    (SEQ ID NO: 16)

LAH4-A3:
KKALLLAALHHLLALAHHLAALLKKA    (SEQ ID NO: 17)

LAH4-A4 (also called vectofusin-1):
KKALLHAALAHLLALAHHLLALLKKA    (SEQ ID NO: 18)

LAH4-A5:
KKALLHALLAHLAALLHALLAHLKKA    (SEQ ID NO: 19)

LAH4-A6iso:
KKALLHALLAALLAHLHALLAHLKKA    (SEQ ID NO: 20)

LAH4-A4-K1N:
KALLHAALAHLLALAHHLLALLKKA     (SEQ ID NO: 21)

LAH4-A4-K3N:
KKKLLHAALAHLLALAHHLLALLKKA    (SEQ ID NO: 22)

LAH4-A4-dKC:
KKALLHAALAHLLALAHHLLALLA      (SEQ ID NO: 23)

LAH4-A4-d1aa:
KKALLHAALAHLLALAHHLLALLK      (SEQ ID NO: 24)

LAH4-A4-d2aa:
KKLLHAALAHLLALAHHLLALLK       (SEQ ID NO: 25)

LAH4-A4-d2Caa:
KKALLHAALAHLLALAHHLLALK       (SEQ ID NO: 26)

LAH4-A4-d3aa:
KKLHAALAHLLALAHHLLALLK        (SEQ ID NO: 27)

LAH4-A4-d5aa:
KKLHAALAHLLALAHHLLAK          (SEQ ID NO: 28)

LAH2-A6:
KKALLHAALAHLLALAAALLALLKKA    (SEQ ID NO: 29)

K2-L10A12-K2:
KKALLAAALAALLALAAALLALLKKA    (SEQ ID NO: 30)

LAH4-A4-Leu:
KKLLLHALLAHLLALLHHLLALLKKL.   (SEQ ID NO: 31)
```

Preferably, one uses a functional derivative of the LAH4 peptide. Preferably, said functional derivative is LAH4-A4, which is also called vectofusin-1, and which has SEQ ID NO: 18.

The present invention also relates to a pharmaceutical composition comprising the stable pseudotyped lentiviral particles of the invention, or the immune cells transfected with said stable particles, in a pharmacologically acceptable medium. By "pharmacologically acceptable medium", it is meant a vehicle compatible with an administration to the patient.

The present invention also relates to the use of the stable lentiviral particles pseudotyped with an ERV syncytin as previously described and notably pseudotyped with HERV-W, HERV-FRD or the murine syncytin-A including a heterologous gene of interest, preferably stable lentiviral particles pseudotyped with an ERV syncytin as previously described and notably pseudotyped with HERV-W, HERV-FRD or the murine syncytin-A including a heterologous gene of interest, for generating animal models, particularly in mice (so as to obtain murine models). This may be useful for exploring disease mechanisms, particularly B cell diseases.

The invention will now be exemplified with the following examples, which are not limitative.

FIGURE LEGENDS

FIG. 1: Transduction of BeWO cells with syncytin-pseudotyped vectors in the presence of various transduction additives BeWO cells were infected with GFP-encoding vectors, either with LV-VSVg ($10^8$ TU/mL) or with LV-Syn2 ($10^5$ TU/mL) in the absence or presence of additives protamine sulfate (PS), polybrene (PB) or Vectofusin-1 (VF1) and transgene expression was measured by FACS after 3 days. The percentages of live GFP+ cells in the gate are shown. Results from one experiment.

Figure 2:
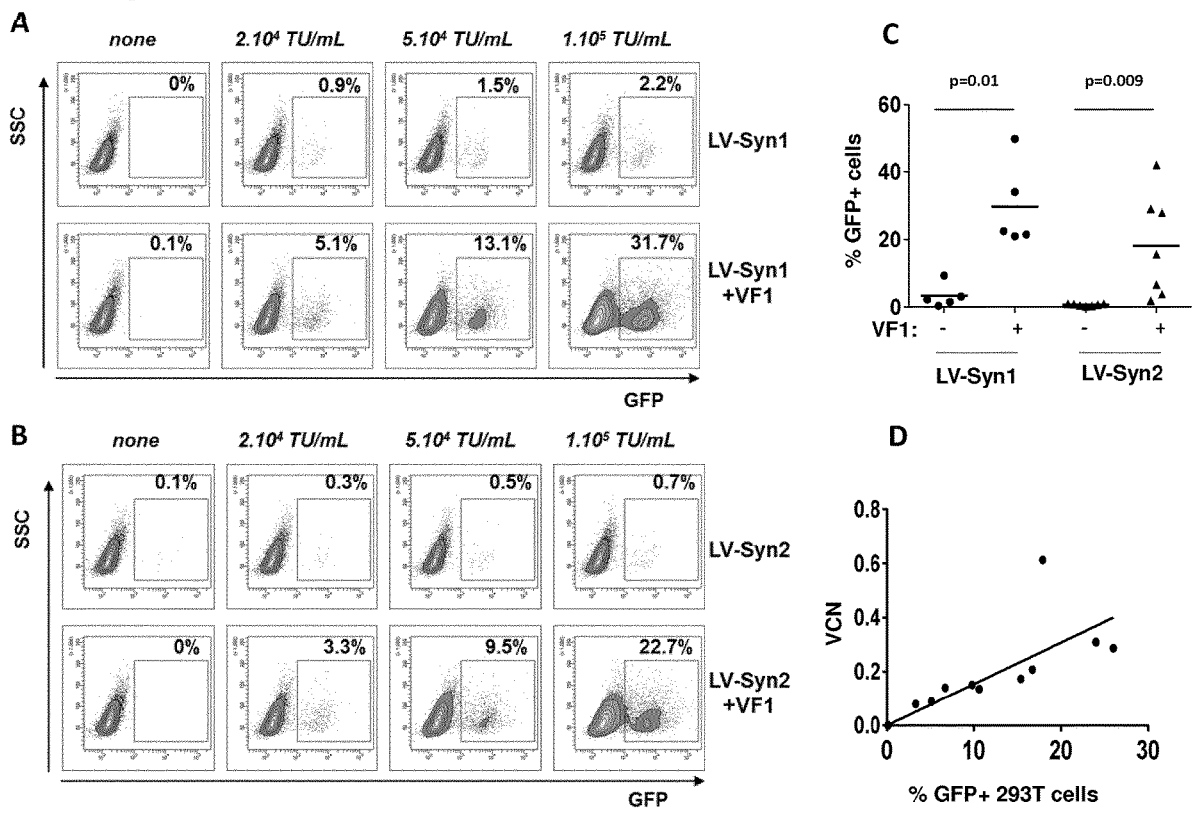

FIG. 2: Transduction of 293T cells with syncytin-pseudotyped vectors and Vectofusin-1 (VF-1)

A. B. One representative experiment out of 3 showing the dose-dependent effects of syncytin-pseudotyped vectors in the presence of VF1. 293 T cells were cultured with GFP-encoding LV-Syn1 (A) or LV-Syn2 (B) using vector concentrations ranging from $10^4$ to $10^5$ TU/mL and in the absence or presence of VF1. GFP expression was measured by FACS after 3 days. C. The enhancing effect of VF1 is statistically-significant as shown in 5-6 experiments using a Mann-Whitney test. D. Correlation between expression of GFP as measured by FACS and vector copy number per cell (VCN) as measured by qPCR was obtained from 3 separate experiments testing different vector concentrations.

Figure 3:
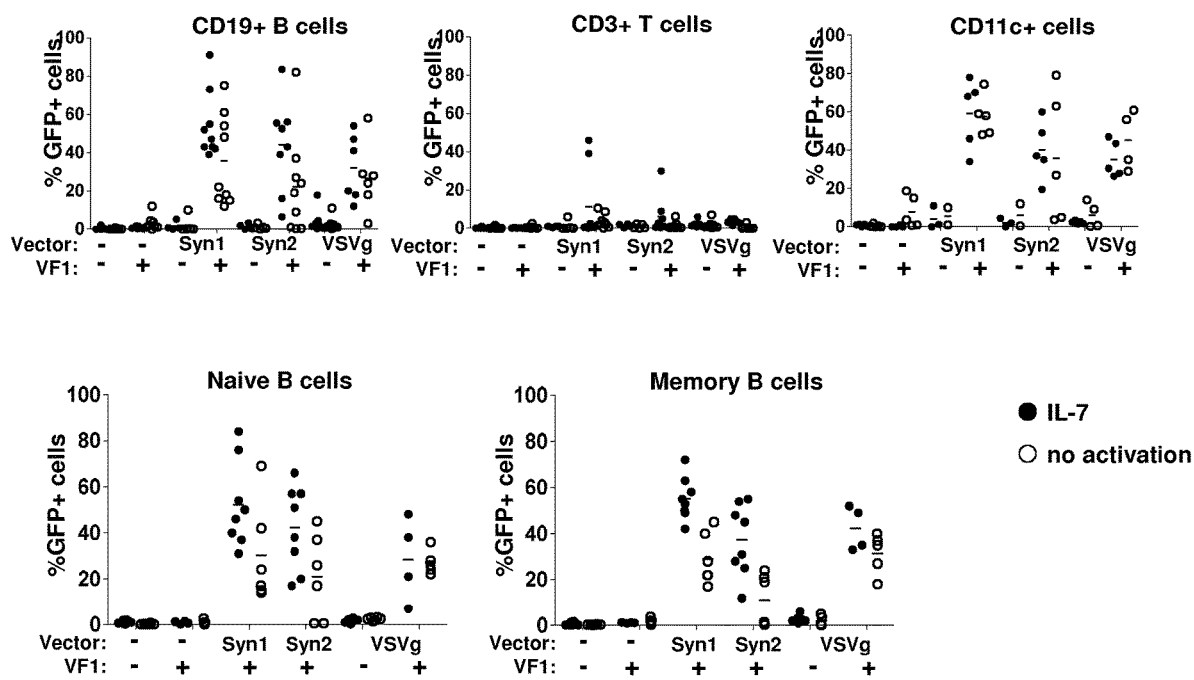

FIG. 3: Transduction of primary blood cell subsets with syncytin-pseudotyped vectors Human peripheral blood mononuclear cells (PBMC) (4 to 9 separate blood donors) were infected with GFP-encoding LV-Syn1 or LV-Syn2 vectors ($10^5$ TU/mL) in the absence or presence of VF1 and either immediately after isolation of the cells (no activation) or following an overnight culture of cells with IL-7 (10 ng/mL). After 3 days, GFP was measured by FACS in different subsets of live cells (CD3+CD19− CD11c− T cells; CD3−CD19+CD11c− B cells; CD3− CD19− CD11c+ myeloid dendritic cells), naïve (CD27−) or memory (CD27+) B cell subsets.

Figure 4:
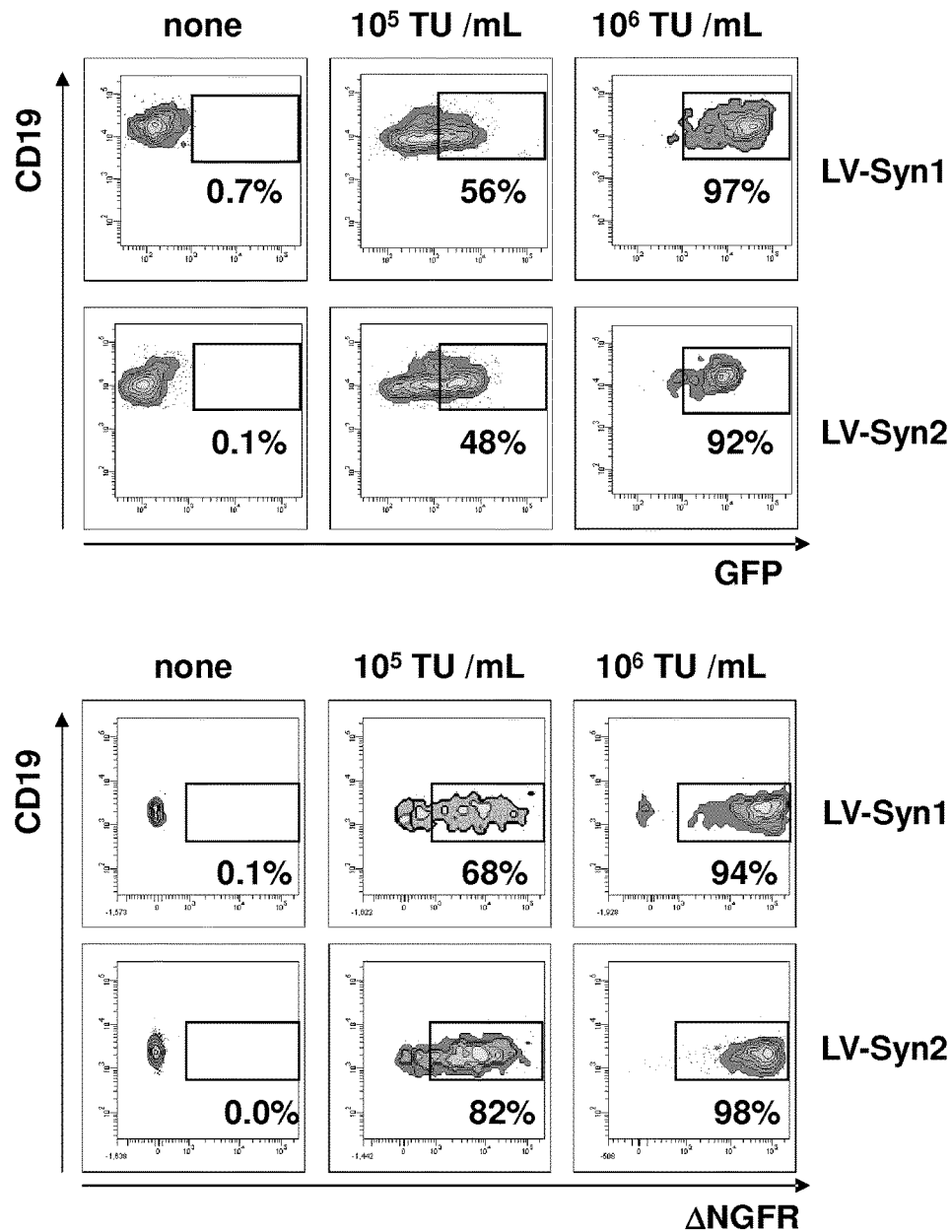

FIG. 4: Dose-dependent effects of syncytin-pseudotyped vectors on blood cell subsets Representative results of 3 donors of PBMC incubated with IL-7 overnight, then transduced with ΔNGFR-encoding LV-Syn1 and LV-Syn2 at concentrations $10^5$ and $10^6$ TU/mL in the presence of VF1. Transgene expression was measured by FACS after 3 days.

Figure 5:
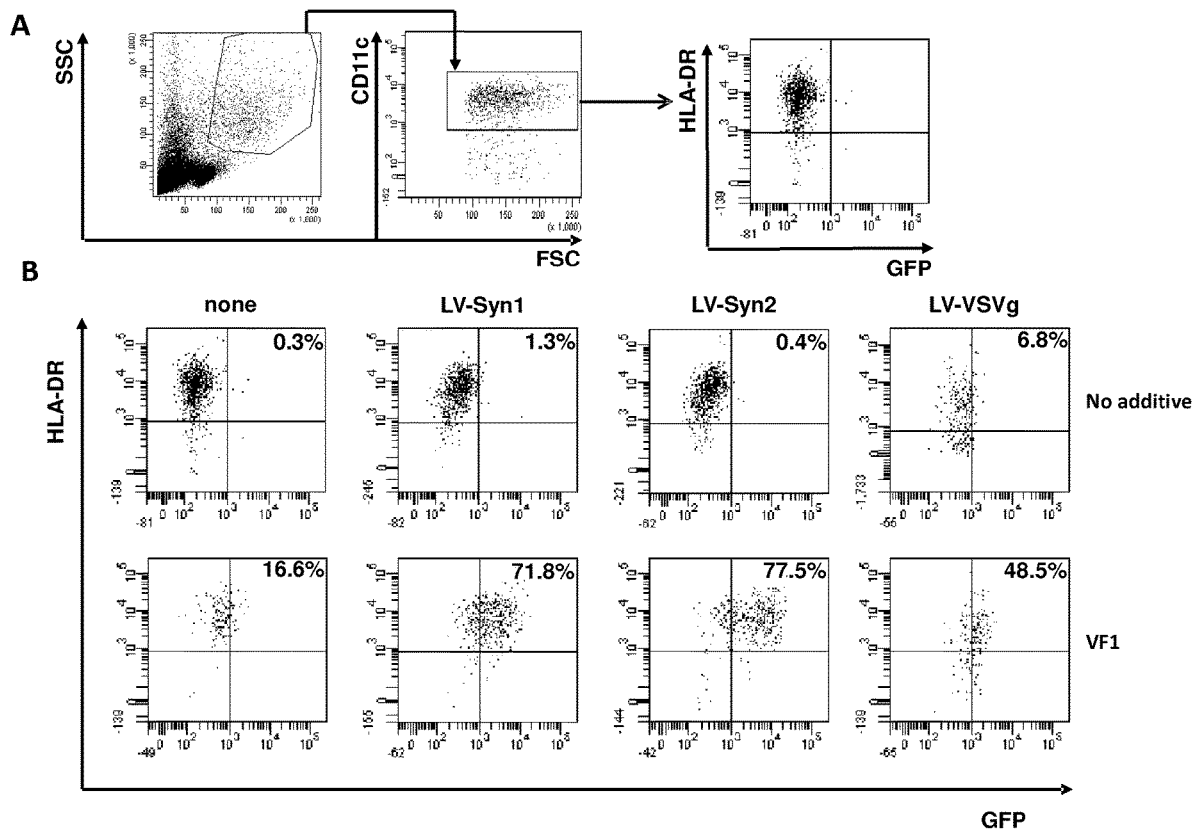

FIG. 5: Transduction of CD11c+ blood cells with syncytin-pseudotyped vectors Whole PBMC (2 donors tested in 2 separate experiments) or plastic-adherent PBMC (1 donor tested in another separate experiment) were transduced with GFP-encoding LV-Syn1 or LV-Syn2 ($2\times10^5$ TU/mL) or LV-VSVg ($10^8$ TU/mL) vector in the absence of presence of VF1 (12 μg/mL). Cells were washed and further cultured in XVivo20+10% FCS+GM-CSF+IL-4 for 3 to 7 days. A. Gating strategy for the analysis of CD11c+ HLD-DR+ myeloid cells. B. Representative experiment out of 3 showing the transduction of CD1c+ HLD-DR+ cells obtained after 3 days in different conditions.

Figure 6:
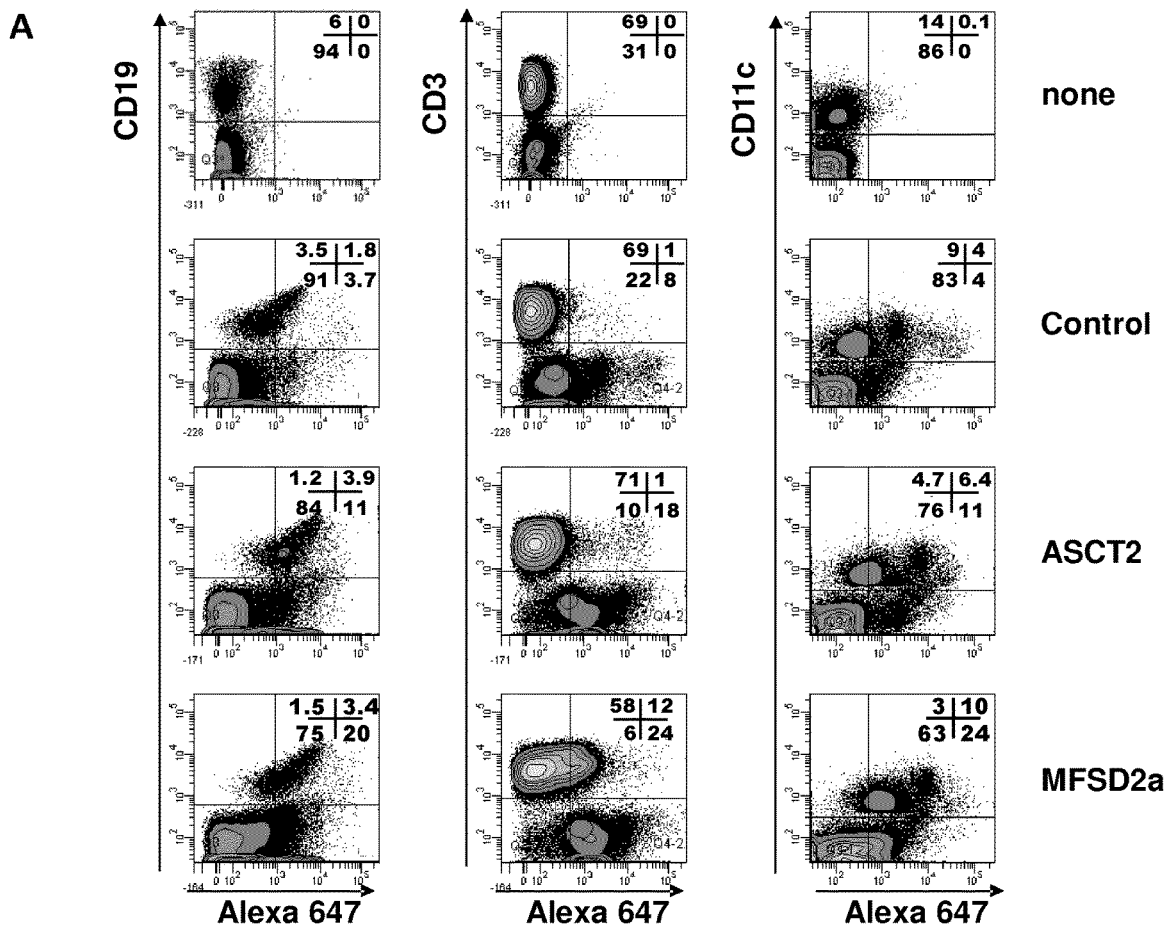
Figure 6:
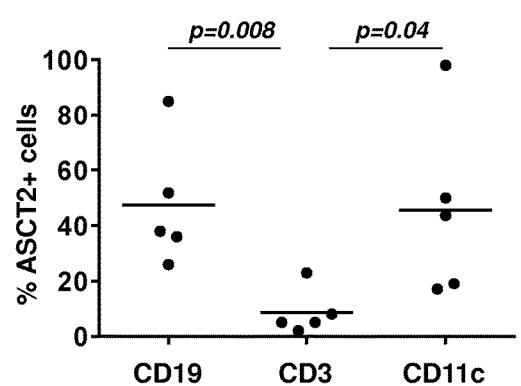
Figure 6:
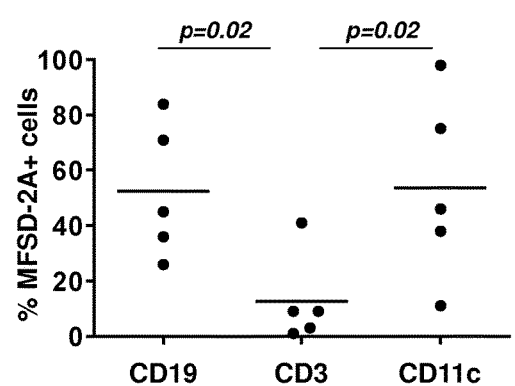
Figure 6:
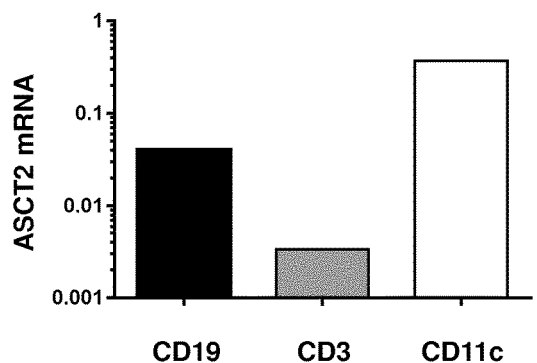
Figure 6:
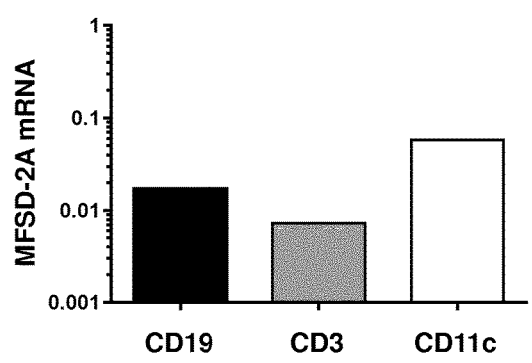

FIG. 6: Expression of ASCT2 and MFSD2a receptors on blood cells

A. Multicolor FACS analysis for ASCT2 and MFSD2a expression in CD19+B cells, CD3+ T cells and CD11c+ myeloid dendritic cells in one representative experiment out of 3 (1 blood donor each). B. Average and standard deviation of the percentage of cells expressing the indicated receptors in 5 experiments, after subtraction of the background obtained with the rabbit immunoglobulin control. C. RT-PCR analysis of MFSD2a and ASCT2 mRNA on PBMC cell subsets averaging 2 experiments.

Figure 7:
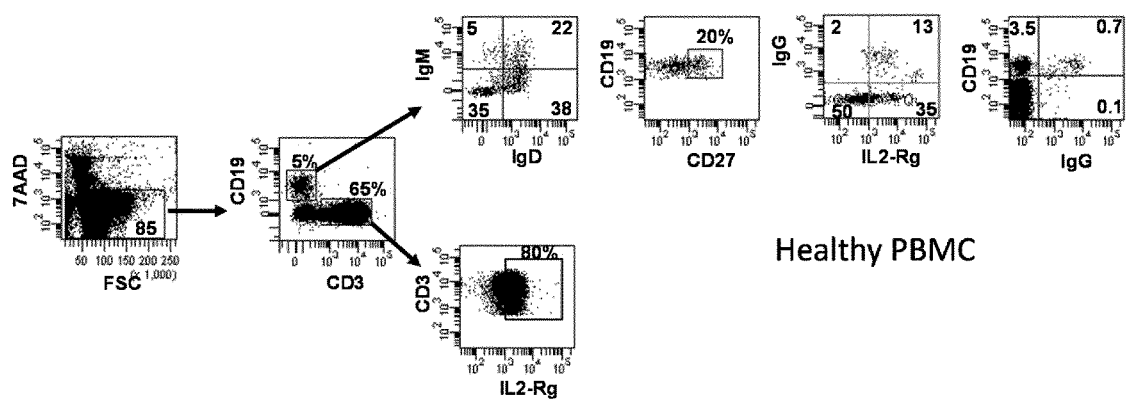
Figure 7:
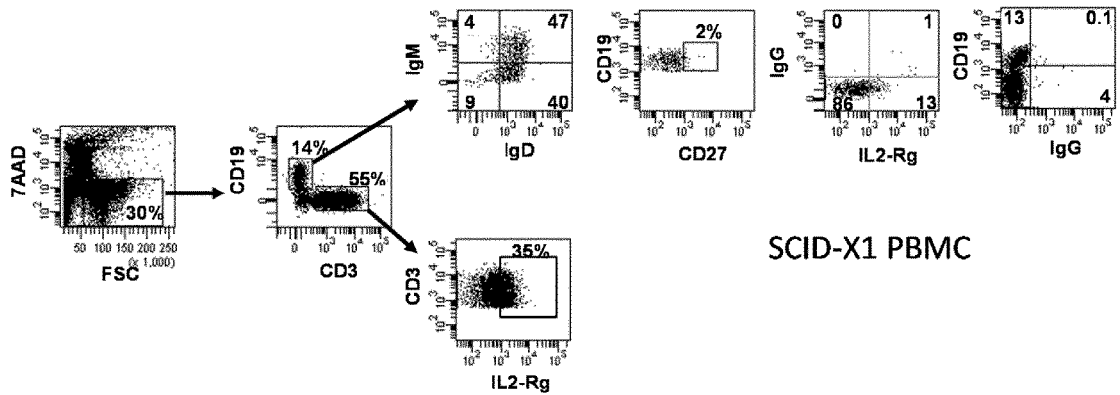

FIG. 7: Phenotype of blood mononuclear cells of a SCIDXI patient treated by gene therapy. Flow cytometry analysis was performed: (A) with a healthy donor PBMC and in comparison (B) after thawing the patient's peripheral blood mononuclear cells (PBMC) and in comparison.

Figure 8:
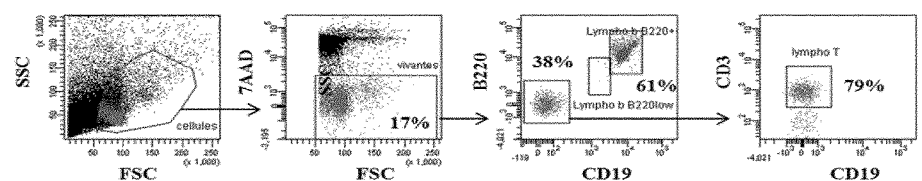
Figure 8:
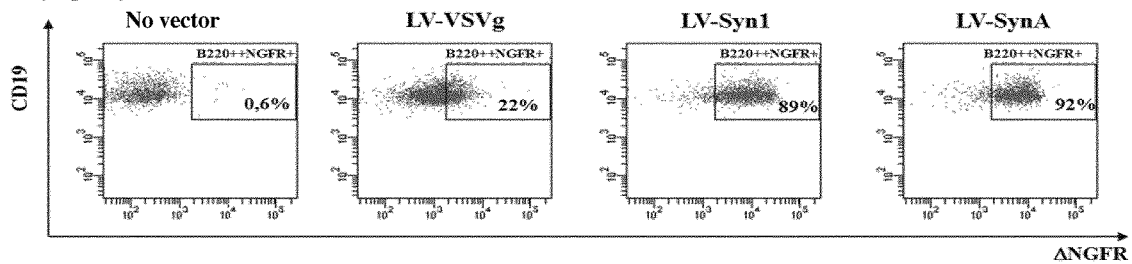
Figure 8:
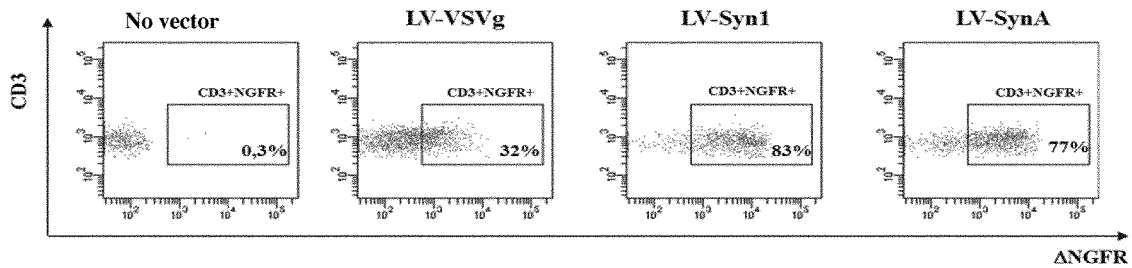
Figure 9:
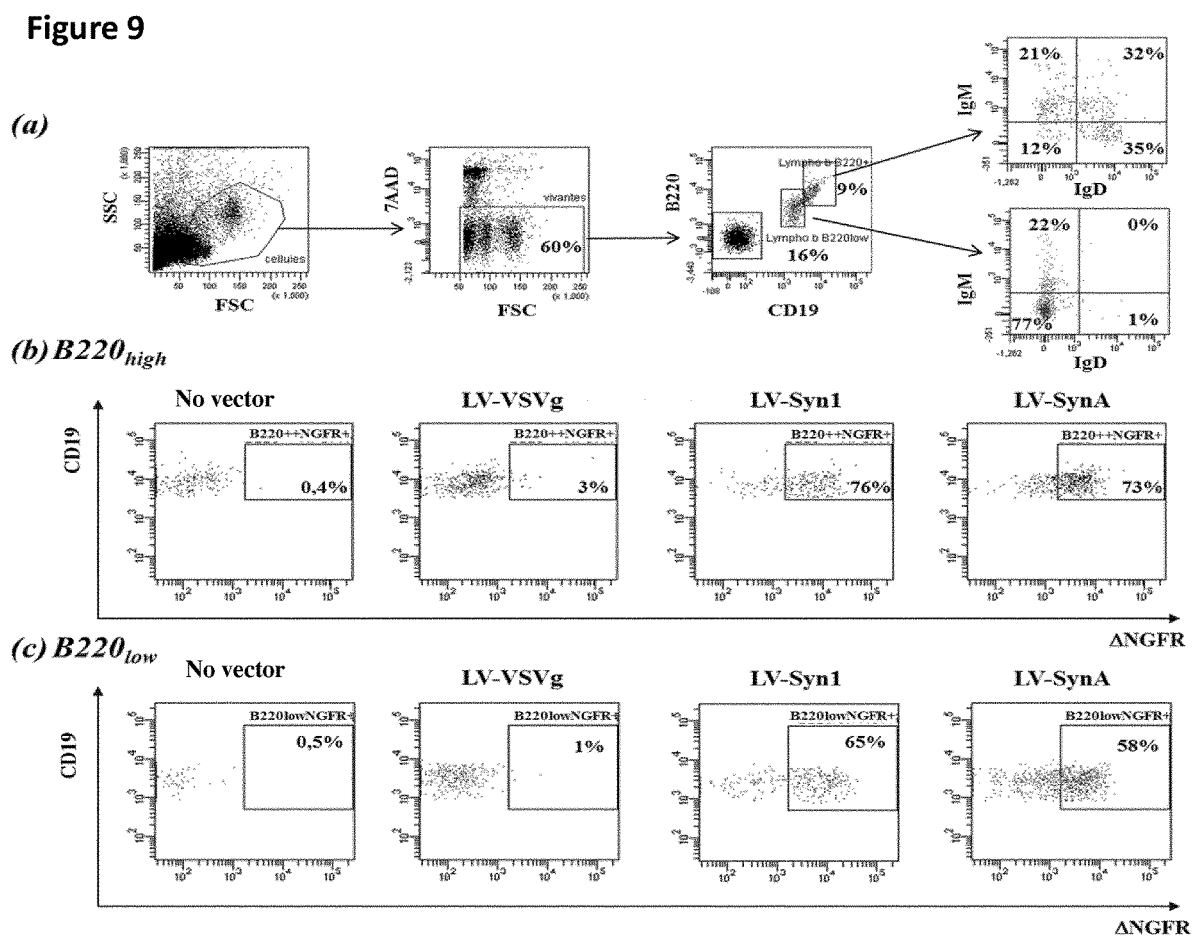

FIGS. 8-9: Transduction of murine spleen cells (FIG. 8) and of bone marrow cells (FIG. 9) with LV-Syn A vectors. LV-SynA vector encoding dNGFR was added on red-blood cell-depleted spleen cells obtained from C57Bl/6 mice. After 3 days, the phenotype of cells and transgene expression were measured by flow cytometry.

Figure 10:
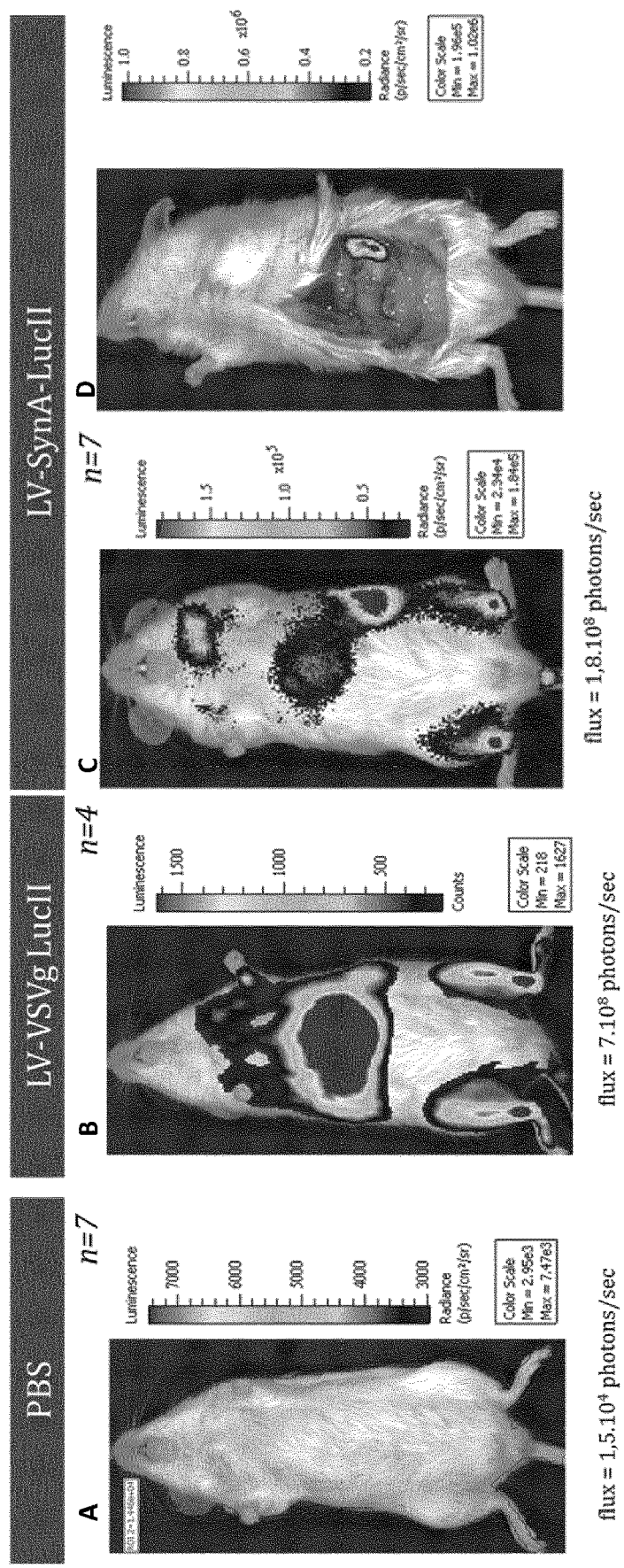

FIG. 10: In vivo delivery of the LucII transgene with LV-SynA. A single bolus of LV-SYn A encoding LucII (C, n=7, flux: $1,8.10^8$ photons/sec) was injected intravenously into albinos C57Bl/6 mice ($5\times10^5$ TU/mouse n=3). As control a LV-VSVg encoding the same transgene was used (B, n=4, flux: $7.10^8$ photons/sec), as well as PBS (A, n=7, flux: $1,5.10^4$ photons/sec). Bioluminescence detection of transgene expression was performed 16 days post IV injection of LVs. One of the anesthetized mice was opened to confirm bioluminescence of the spleen (D).

FIG. 11

A. Optimization of plasmid ratio for LV production by transient transfection in HEK293T cells. Production of LV-Syn2 vector coding for GFP using various amounts of pcDNA3Syn2 plasmid in each T175 cm² flask as indicated on the X axis. Medium was collected 24 h after transfection and p24 was measured by ELISA. Results of average ±SD of 4 measures.

B. Dose-dependent increase in transduction and stability of transduction over time. HEK293T cells were transduced with increasing concentrations of LV-Syn1 encoding GFP. Cells were cultured for the indicated times (d=days) at which GFP expression was measured by FACS. Results are expressed as percentage of GFP+ cells in the culture. Results of 1 experiment representative of 4.

C. Comparative transduction of different cell lines with syncytin-pseudotyped LV. HEK293T cells, BeWO cells or HCT116 cells were transduced with LV-Syn1 ($10^5$ TU/mL), LV-Syn2 ($10^5$ TU/mL) or LV-VSVg ($10^6$ TU/mL) vectors encoding GFP. Expression of GFP was measured by FACS after 3 days. Results obtained with LV-Syn 1 and LV-Syn1 respectively on 5 and 6 separate experiments on 293 T cells; 1 and 3 experiments on BeWO cells and 2 and 4 experiments on HCT116 cells.

FIG. 12

A. Treatment schema of PBMC with vectors

B. FACS gating strategy to analyse the transduction of various B cell subpopulations

FIG. 13

A. FACS gating strategy to analyze the transduction of dendritic cells which are CD3-CD19-, HLA-DR+, CDia+ and express or not GFP and CD86 or CD80. Transduction of PBMC with LV-Syn, LV-Syn2 or LV-VSVG vectors in the same conditions as in FIG. 5 and expression of CD80 and CD86 (percentages indicated in quadrants) on the subset of CD3-CD19-CD14-CDIa+GFP+ cells after 7 days.

B. Same as A. and expression of GFP (percentages indicated in histogram) on the subset of CD3-CD19-CD14+ HLA-DR+ cells after 7 days.

Figure 14:
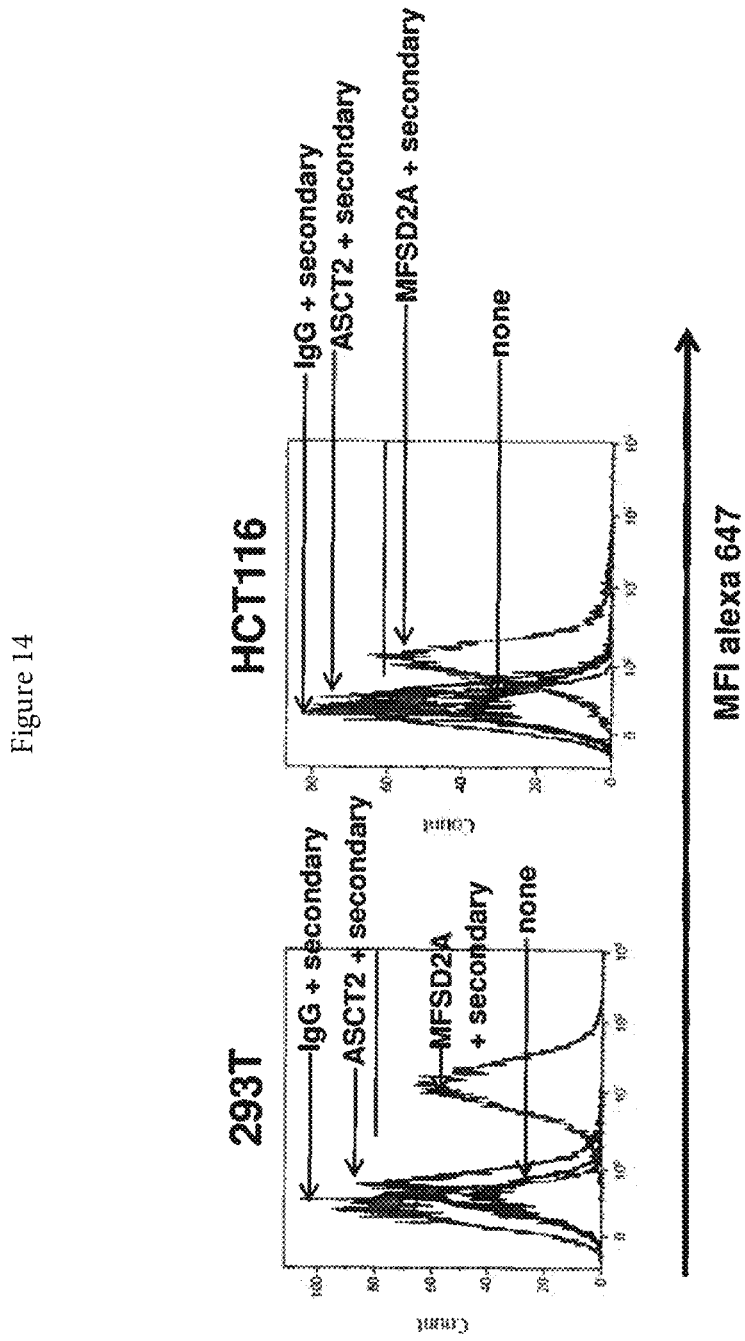

FIG. 14: Immunostaining for ASCT2 and MFSD2a on HEK293T cells and HCT116 cells

Histograms represent the mean fluorescence intensity (MFI) of unstained negative control cells (293T: 5%; HCT116: 3%), cells stained with irrelevant IgG and the Alexa 647-conjugated secondary antibody (293T: and HCT116: 1%), cells stained with the anti-ASCT2 and secondary antibody (293T: 12%, HCT116: 4%) and cells stained with anti-MFSD2a and secondary antibody (293T: 99%, HCT116: 65%).

Figure 15:
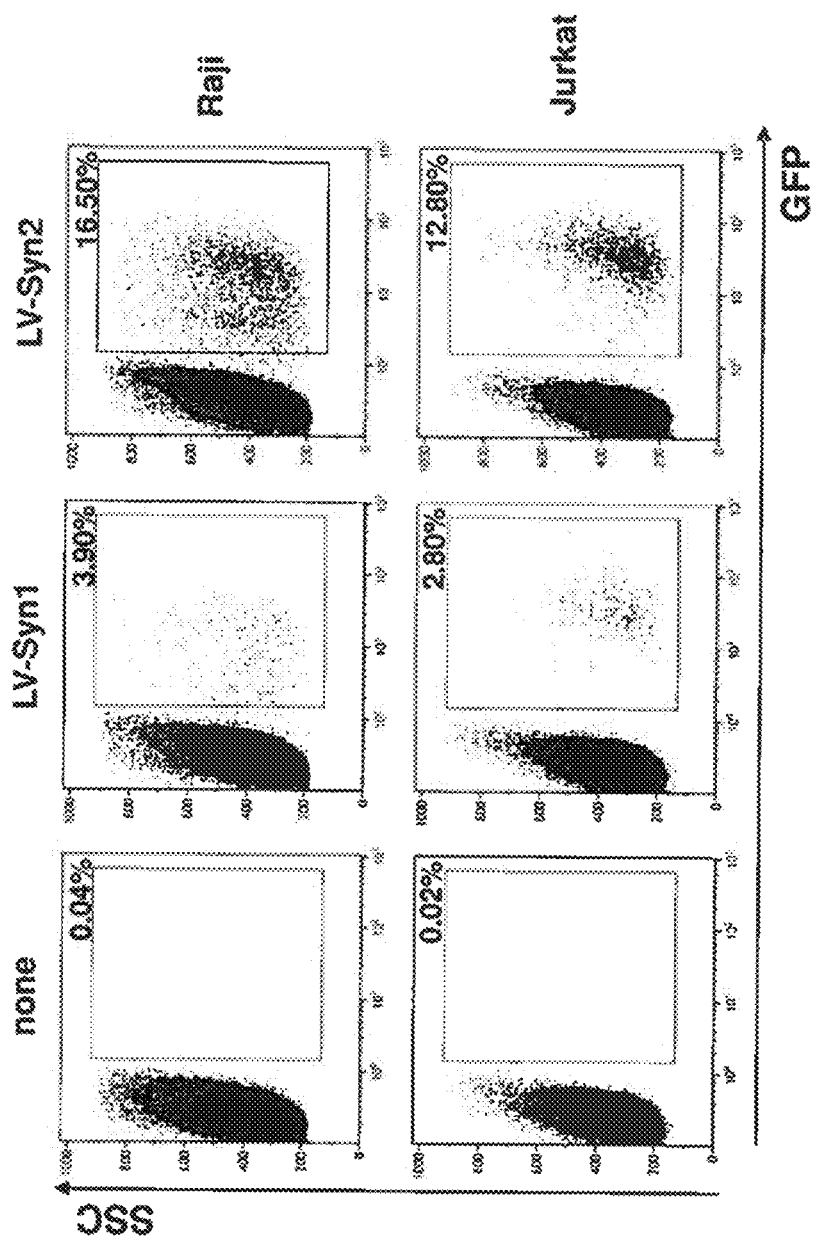

FIG. 15: Transduction of Raji and Jurkat cells with LV-Syn1 and LV-Syn2 vectors encoding GFP using $10^6$ TU/mL vector Cells were analyzed by FACS 8 days after infection.

Figure 16:
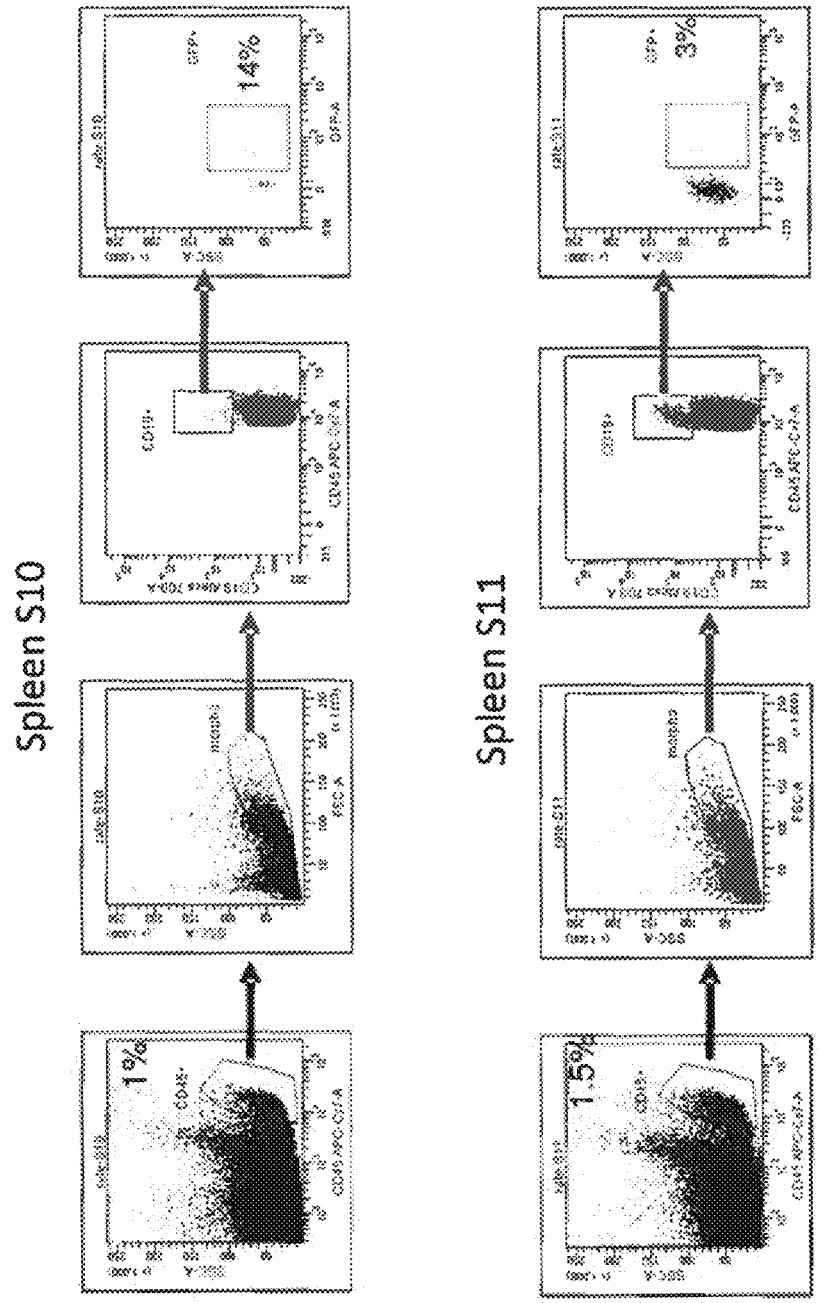

FIG. 16: In vivo transduction with LV-Syn1 vector 7 week-old female NSG mice (Nod/Scid/gc-/-) purchased from Charles River were injected in the retro-orbital sinus with $10^7$ PBMC in 100 µL volume. After 24 hours, the mice were injected intravenously in the tail vein with 150 µL of undiluted LV-Syn1 vector. After 7 days, mice were sacrificed and spleens were collected, lysed with ACK and the red blood cell-depleted fraction was analyzed by FACS to measure GFP on the CD45+ human cell fraction. Results show the FACS plots of 2 mice in which human GFP+ cells were found.

Figure 17:
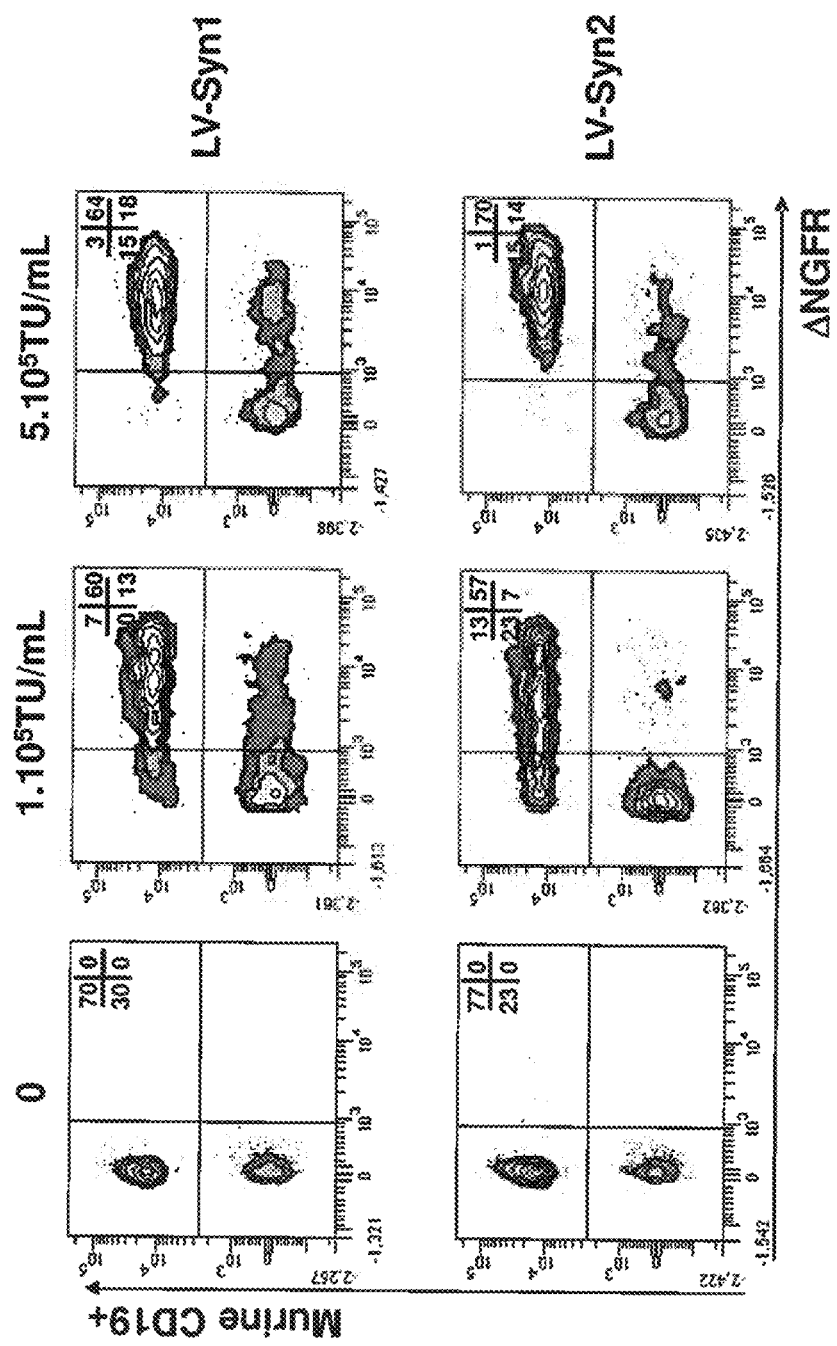

FIG. 17: Ex vivo transduction of murine cells with the LV-Syn1 or LV-Syn2 vectors Spleen cells were obtained from 6 week-old female C57B1/6 mice following red blood cell lysis with ACK. The cells were cultured in RPMI supplemented with 10% FCS and bet2 mercaptoethanol at the concentration of $10^6$ cells/ mL in 100 µL in the presence of LV-SYn1 or LV-Syn2 encoding ΔNGFR at 1 or 5×$10^5$ TU/mL and VF1 (12 µg/mL). After 3 days, expression of ΔNGFR was measured by FACS on live cells.

Figure 18:
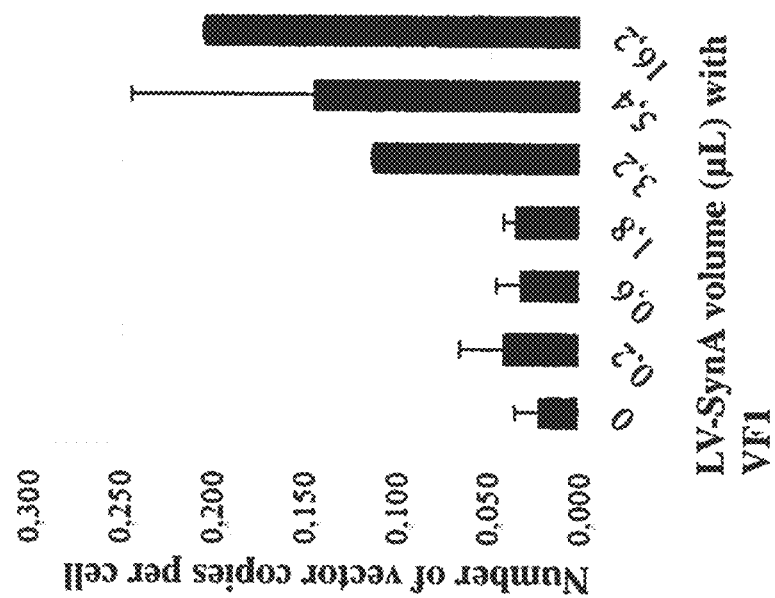

FIG. 18: Infectious titration of LV-SynA on the murine B cell lymphoma cell line A20

A20 cells were transduced with different amounts of LV-SynA vector (0, 0.2, 0.6, 1.8, 3.2, 5.4 and 16.2 µL) with VF1 (red) and without VF1) To 12 µg/mL. The cells are cultured for 7 days in complete medium. Evaluation of the number of copies of syncytin A by qPCR.

EXAMPLE 1

Human Endogenous Retroviral Envelope Glycoproteins Syncytin-1 and Syncytin-2 Enable an Effective Lentiviral Transduction of Human Primary B Cells and Dendritic Cells Materials and Methods Cell Lines Human embryonic kidney 293T cells and human colorectal carcinoma HCT116 cells (CCL-247; ATCC, Manassas, Va.) were cultured at 37° C., 5% CO2 in Dulbecco's modified Eagle's medium (DMEM+glutamax) (Life Technologies, St-Aubin, France) supplemented with 10% of heat inactivated fetal calf serum (FCS) (Life Technologies). Human choriocarcinoma BeWO cells (CCL-98; ATCC) were cultured in Ham's FI2K medium (Life technologies) supplemented with 10% of FCS. Raji cells and Jurkat cells were infected in XVivo 20 medium.

Cloning of Syncytin-Expressing Plasmids and Production of Vectors

Plasmids pCDNA3-syncytin-1 and pCDNA3-syncytin-2 coding for human syncytin-1 (ERVW-1-001) or human syncytin-2 (ERVFRD-1) were constructed by cloning the respective synthesized DNA sequences (Gencust, Dudelange, Luxembourg) corresponding to Ensembl genome browser ENST00000493463 and ENSG00000244476 transcript sequences, into a pCDNA3 plasmid (Invitrogen, Carlsbad, Calif.) using NHeI et XhoI restriction enzymes. Plasmid sequences were verified by two strand sequencing. The syncytin-2 plasmid functionality was verified by immunoblotting protein extracts following transfection of 293T cells using the anti-HERV-FRD antibody (LS-BIO, Nanterre, France) detecting a 65-70Kd protein expected to be syncytin-2. Plasmids were produced with endotoxin-free using DNA RNA purification Nucleobond kit (Macherey-Nagel, Duren, Germany). Lentiviral particles pseudotyped with either syncytin-1 or syncytin-2 were produced by transient transfection of 293T cells with 4 plasmids, using calcium phosphate. Each TI75 cm² flask was transfected with 14.6 µg pKLgagpol expressing the HIV-1 gagpol gene, 5.6 µg pKRev expressing HIV-1 rev sequences, 22.5 µg of the gene transfer cassette (pCCL PGK GFP expressing enhanced green fluorescent protein (GFP) under control of the human phospho glycerate kinase (PGK) promoter (Charrier et al, 2011) or pCCL PGK delta-NGFR expressing a truncated form of the nerve growth factor receptor (NGFR) under control of the human PGK promoter) and 22 µg of either the pCDNA3-syncytin-1 or pCDNA3-syncytin-2 plasmid. Medium was changed the following day and replaced by DMEM 4.5 g/L glucose supplemented with penicillin and streptomycin and 10% FCS. After 24 hours, medium containing viral particles was collected, centrifuged at low speed, sterile-filtered (0.22 µm) and concentrated by ultracentrifugation 50 000 g (19500 RPM using a Beckman ultracentrifuge with rotor SW28) for 2 h at 4° C. The pellet was resuspended in PBS, aliquoted and stored at -80° C. VSVg-pseudotype particles were produced also by transient transfection as reported (Merten et al, 2011).

Transduction Additives

Vectofusin-1 (VF1) peptides were synthetized by standard fluorenyl-methyloxy-carbonyl chloride solid-phase peptide synthesis, followed by HPLC and mass spectrometry purification (Gencust). Peptides were solubilized in H₂O, aliquoted and stored at -80° C. until used. When needed for transduction experiments, VF1 was thawed, resuspended in medium and added to vector and to cells at a final concentration of 12 µg/mL. Protamine sulfate (PS) (Sigma-Aldrich, St Louis, Mo.) and polybrene (PB) (Sigma-Aldrich) were also diluted extemporaneally with vector and cells and respectively used at final concentrations of 8 µg/mL and 6 µg/mL in the transduction culture.

Titration of Vectors

Concentrated and cryopreserved vector was titered before use. Physical particle titer was determined by p24 ELISA (Alliance© HIV-1 Elisa kit, Perkin-Elmer, Villebon/Yvette, France) as previously reported (Charrier et al, 2011). Infectious titer was determined by adding serial dilutions of vector to HEK293T cells in the presence of 12µg/mL VF1 and after 3 days, 293T cells were analyzed by flow cytometry to calculate a transducing units titer (TU/mL) or by qPCR to measure infectious genomes (ig/mL) using standard calculations (Kutner et al, 2009).

Culture and Transduction of Peripheral Blood Mononuclear Cells

Peripheral blood collected with EDTA was purchased from the Etablissement Francais du Sang (Evry, France). Peripheral blood mononuclear cells (PBMC) purified by Ficoll gradient centrifugation (Eurobio, les Ulis, France) were suspended in serum-free medium X-VIVO 20 (Lonza, Levallois-Perret, France) for transduction. In some experiments, cytokines IL-7 (10 ng/µL) (Miltenyi Biotech, Bergisch Gladbach, Germany) was added to the medium overnight prior to transduction. For transduction, LV-Syn1 or LV-Syn2 vectors ($1.10^5$ TU/mL), or LV-VSVg ($1.10^8$ TU/mL) were added to cells in the presence of VF1 (12 µg/mL). After 6 hours, medium was changed to XVivo20 supplemented with 10% FCS and IL-7 (10 ng/mL) and cells were cultured for up to 7 days. To expand transduced B cells, CD40L (2 µg/mL) and IL-4 (20 ng/mL) was added to the medium and cells were cultured in these conditions for up to 2 weeks. To expand myeloid dendritic cells, hGM-CSF (50 ng/ml) and IL-4 (20 ng/ml) were added to medium.

EBV Immortalization

PBMC were cultured overnight with IL-7, then infected with vectors. After 6 hours, the cells were washed and cultured in the presence of B95.8 marmoset cell supernatant with cyclosporin using standard procedures for EBV immortalization. Medium was changed twice weekly.

Transduction of a SCID-X1 Patient Cells

PBMC of SCID-X1 patient treated by gene therapy were rapidly thawed at 37° C. and then washed twice with PBS. After trypan blue counting the cells are labeled with 2 µM CFSE (Molecular Probes, Cambridge, UK), transduced with Lv-Syn1 IL2rg vector and cultured ($3.10^5$/200 µL) in 96-well round bottomed plates in the absence or presence of CD40Ligand [2 µg/mL] (Miltenyi Biotec) and IL-21 [50 ng/mL] (Miltenyi Biotec). After 3, 6 and 7 days culture, B cell transduction (ie, NGFR or IL2Rg expression), B cell proliferation (ie, CFSE dilution) and the frequency of CD19+ CD27+ cells were determined by flow cytometry. Human IgG secretion in medium was determined by ELISA (Sigma-Aldrich, St Louis, Mo.).

In Vitro B Cells Activation

PBMCs were labeled with 2 µM CFSE (Molecular Probes, Cambridge, UK) and cultured ($3.10^5$/200 µL) in 96-well round bottomed plates in the absence or presence of CD40Ligand [2 µg/mL] (Miltenyi Biotec) and IL-21 [50 ng/mL] (Miltenyi Biotec). After 3, 6 and 7 days culture, B cell transduction (ie, NGFR or IL2Rg expression), B cell proliferation (ie, CFSE dilution) and the frequency of CD19+ CD27++ plasmablasts were determined by flow cytometry. Human IgG secretion was determined by ELISA (Sigma-Aldrich, St Louis, Mo.).

Flow Cytometry

Antibodies used for flow cytometry were purchased from BD-Biosciences (Le Pont de Claix, France) and include PE conjugated anti-CD3 and anti-CD1a, Alexa-Fluor 700 conjugated anti-CD19, APC-H7 conjugated anti-CD45 and anti-IgD, CF594 conjugated anti-IgM, PeCy7 conjugated anti-CD27 and anti-HLA-DR, APC conjugated anti-CD14, V450 conjugated anti-CD11c. Prior to adding antibodies to cells, Fc receptors were blocked by incubating cells with gamma-globulin (1 mg/mL) (Sigma Aldrich) for 15 minutes, at 4° C. Saturating amounts of antibodies were then added for 30 minutes at 4° C. in PBS with 0.1% bovine serum albumin (BSA) (Sigma Aldrich) and cells were washed twice. At the end of the procedure, 7-amino-actinomycin D (0.3 mg/mL) (Sigma-Aldrich) was added to exclude dead cells. For receptor studies, rabbit polyclonal anti-SLC1A2 (ASCT2) (Abcam, Paris, France), anti-MFSD2a (Origene, Rockville, Md.) or rabbit immunoglobulin controls (Origene) were used and revealed by Alexa 647-conjugated goat anti-rabbit antibodies (Thermo Fisher Scientific, Waltham, Md.). Acquisitions were performed on a LSRII using Diva software (BD-Biosciences) and analyses were carried out with Kaluza software (Beckman-Coulter, Villepinte, France).

The detection of human IL2Rg was performed using PE conjugated anti-human CD132 antibody (BD bioscience).

Measure of ASCT2 and MFSD2A Expression by RT-qPCR

Total RNA was extracted from purified cells using SV total RNA isolation (Promega, Charbonniére les bains, France). Residual DNA was removed from the samples using the free DNA kit (Ambion, Courtaboeuf, France). cDNA was synthesized from 1 µg of RNA using random hexamers according to the protocol Superscript II first strand synthesis system for reverse transcription-PCR (Invitrogen). Real time PCR was performed using LightCycler 480 system (Roche, Bale, Switzerland) with 0.1 µM of each primer according to the protocol Sybr Green PCR Master Mix (Applied Biosystem, Foster city, Calif., USA). The primer pairs used for amplification of either ASCT2 or MFSD2A were described previously (Cornelis et al, PNAS, 2008 and Toufailly et al, placenta, 2013). Sequences of ASCT2 primers are (sense, 5'-GGCTTGGTAGTGTTTGCCAT-3'; antisense, 5'-GGGCAAAGAGTAAACCCACA-3') and MFSD2A primers are (sense, 5'-CTCCTGGCCAT-CATGCTCTC-3'; antisense, 5'-GGCCACCAAGAT-GAGAAA-3'). We also used TFIID (Transcription Final II D) primers as normalization. TFIID primers sequences are (sense, 5'-ACGGACAACTGCGTTGATTTT-3'; antisens, 5'-ACTTAGCTGGGAAGCCCAAC-3'). Results are expressed in fold change using the formula: relative abundance=$2^{-\Delta\Delta Ct}$ with ΔCt=Ct ASCT2 or MFSD2A−Ct TFIID and ΔΔCt=ΔCtsample−ΔCtcalibrator.

In Vivo Transduction with LV-Syn1 Vector 7 week-old female NSG mice (Nod/Scid/gc−/−) purchased from Charles River were injected in the retro-orbital sinus with $10^7$ PBMC in 100 µL volume. After 24 hours, the mice were injected intravenously in the tail vein with 150 µL of undiluted LV-Syn1 vector. After 7 days, mice were sacrificed and spleens were collected, lysed with ACK and the red blood cell-depleted fraction was analyzed by FACS Ex Vivo Transduction of Murine Cells with the LV-Syn1 or LV-Syn2 Vectors Spleen cells were obtained from 6 week-old female C57B1/6 mice following red blood cell lysis with ACK. The cells were cultured in RPMI supplemented with 10% FCS and bet2 mercaptoethanol at the concentration of $10^6$ cells/mL in 100 µL in the presence of LV-SYn 1 or LV-Syn2 encoding ΔNGFR at 1 or 5×10⁵ TU/mL and VF1 (12 µg/mL). After 3 days, expression of ΔNGFR was measured by FACS on live cells.

Statistical Analysis

Statistical significance was assessed by one-way ANOVA analysis, Mann-Whitney or Student's t test, as specified, using GraphPad Prism software (GraphPad Inc, La Jolla, Calif.).

Results

Figure 11:
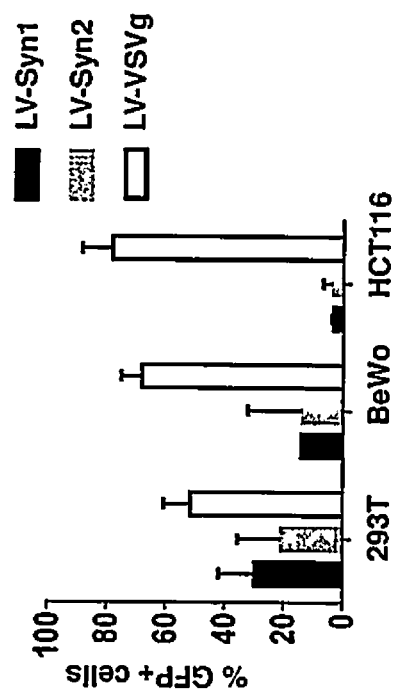
Figure 11:
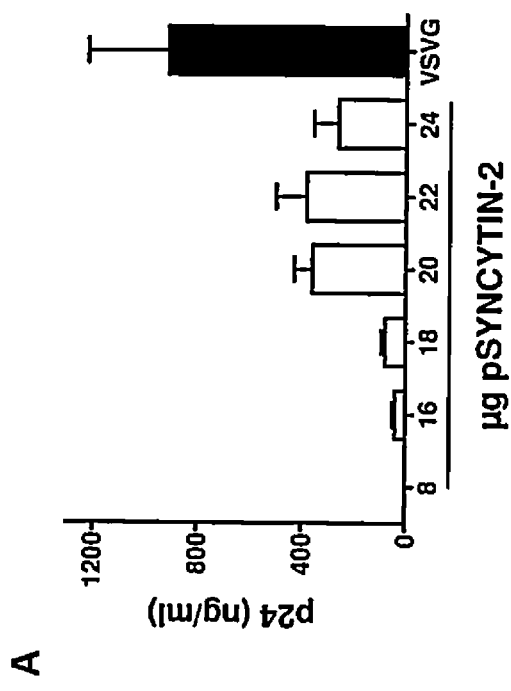

Syncytin-1 and Syncytin-2 Pseudotyped LVs can be Produced as Stable and Infectious Particles Two human endogenous retroviral envelope glycoproteins, syncytin-1 and syncytin-2, were explored as possible new pseudotypes for recombinant HIV-1-derived LV. The full-length cDNAs of these glycoproteins were expressed in a transient LV production system in 293T cells. An optimization of the amount of syncytin-1 and syncytin-2 plasmids for the transfection step increased the production of LV particles based on p24 levels in medium (FIG. 11A). In the conditions defined (see Materials and Methods), it was possible to produce stable and infectious particles pseudotyped with either of these envelopes. Using different transgenes (GFP and dNGFR), harvested raw stocks of LV-Syn-1 titered on average 705 ng p24/mL (n=7 productions) and LV-Syn-2 titered on average 496 ng p24/mL (n=4 productions) (Table 1). Lentiviral particles pseudotyped with either of these envelopes could be successfully concentrated by ultracentrifugation using the same conditions as used for VSVg-pseudotyped particles (Charrier et al, 2011). The concentrated stocks were cryopreserved at −80° C. and were stable for several months. Upon thawing of the LV stocks, titers of 4.1±1.7 E+05 ng p24/mL were obtained for LV-Syn1 (n=6 productions) and 1.7±0.6 E+05 ng p24/mL for LV-Syn2 (n=6 productions) and vectors could be produced to code different transgenes (GFP or ΔNGFR) (Table 1).

TABLE 1

Titers of syncytin 1- and 2-pseudotyped LVs

| Vector | Transgene | Titer harvest ng p24/mL | n | Titer concentrate ng p24/mL × 10⁵ | 293T TU/mL × 10⁶ | n |
|---|---|---|---|---|---|---|
| LV-Syn1 | GFP | 794 ± 217 | 5 | 4.1 ± 1.7 | 2.8 ± 6.0 | 6 |
| LV-Syn2 | GFP | 366 ± 165 | 4 | 1.7 ± 0.6 | 2.7 ± 6.0 | 6 |
| LV-Syn1 | ΔNGFR | 485 ± 64 | 2 | 4.5 ± 3.4 | 6.3 ± 7.5 | 3 |
| LV-Syn2 | ΔNGFR | 671 ± 141 | 3 | 6.4 ± 4.2 | 4.4 ± 1.5 | 2 |

Legend:
Separate batches of LV with the indicated envelope and transgene (n = number of batches tested) were produced by transient transfection, clarified, sterile-filtered, concentrated or not, cryopreserved, thawed and titered. Concentration was performed by ultracentrifugation (19500 rpm (50000 g) for 2 hours). Physical titers in p24 levels were measured by ELISA and infectious titers were measured as 293T cells transducing units (TU) in the presence of Vectofusin-1 using flow cytometry.

To determine the infectious properties of these particles, the inventors first infected the human BeWo choriocarcinoma cell line known to express both the ASCT2 receptor for syncytin-1 and the more restricted MFSD2a receptor for syncytin-2 (Esnault et al, 2008). BeWo cells were not transduced effectively with LV-Syn1 or LV-Syn2 whereas they were well-transduced with VSVg-pseudotyped LV. However, adding cationic agents such as protamine sulfate (PS), polybrene (PB), or Vectofusin-1 (VF1) enhanced the transduction of BeWo cells as shown with LV-Syn2 (FIG. 1).

Of these agents, the greatest level of transduction enhancement was obtained with VF1. Vectofusin-1 is a short histidine-rich amphipathic peptide which enhances the infectivity of lentiviral and γ-retroviral vectors pseudotyped with various envelope glycoproteins including RD114-TR (Fenard et al, 2015 et Majdoul et al, 2015). The effects of Vectofusin-1 had not been tested before with syncytins, and this short peptide reveals the gene transfer potential of syncytin-pseudotyped LV particles.

In the presence of VF1, it was possible to transduce 293 T cells with either of the syncytins-pseudotyped vectors in a dose-dependent manner and reaching levels comparable to those obtained in BeWo cells (FIG. 2 A,B). In contrast, only about 1 to 2% of 293T cells were transduced without this additive. The enhancing effects of VF1 were statistically-significant over repeated experiments in 293T cells using LV-Syn1 or LV-Syn2 (FIG. 2C). The transduction of 293T cells with syncytin-pseudotyped vectors led to a stable genomic integration of the transgene over time as examined in continuous cultures lasting 2 weeks (FIG. 11B). The level of gene expression was coherent with the number of copies per cell, showing no evidence of transgene silencing over time (FIG. 2D).

The discovery of the enhancing effects of the VF1 peptide on LV-Syn1 and LV-Syn2 infectivity enabled the development of a robust infectious titration assay using 293T cells. The choice of the 293T cell line was prompted by failure to transduce HCT116 colon carcinoma cells which are routinely used to titer VSVg-pseudotyped LV in the laboratory. HCT116 could not be transduced with LV-Syn1 or LV-Syn2 at any concentration tested and even in the presence of Vectofusin-1 (FIG. 11C). In addition, 293 T cells were preferred over BeWo cells for this infectious titer assay because of more consistent growth patterns and a trend to higher transduction levels in repeat experiments (FIG. 11C). In the conditions defined for the assay (see Materials and Methods), the infectious titer of concentrated and cryopreserved batches of GFP-encoding LV-Syn1 and LV-Syn2 were respectively 2.8±6×E+06 TU/mL (n=6 batches) and 2.7±6 xE+06 TU/mL (n=6 batches) for GFP transgene and 6.3±7.5×E+06 TU/mL (n=3 batches) and 4.4±1.5 xE+06 TU/mL (n=2 batches) for dNGFR transgene (Table 1). Thus syncytin-1 and syncytin-2 glycoproteins can pseudotype rHIV vectors to obtain stable particles that are infectious and useful for stable gene transfer. Their infectivity requires co-factors and is selective at the cellular level.

LV-Syn1 and LV-Syn2 Vectors Efficiently Transduce Naive Blood Cells

Figure 12:
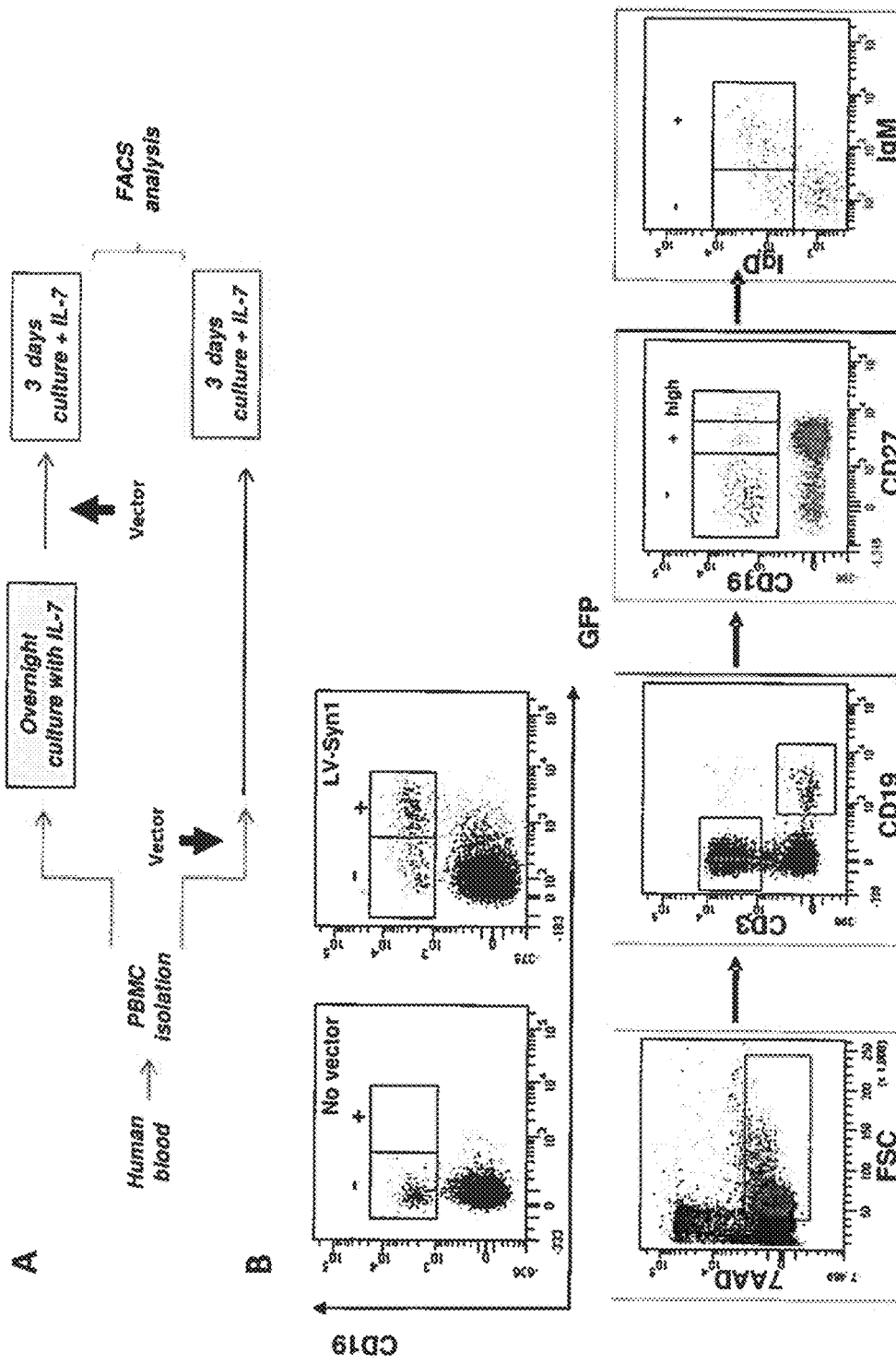

Syncytins are cellular proteins, which may be useful to derive immunologically-tolerated vectors for in vivo applications. Thus, to evaluate if syncytin-pseudotyped vectors would interact with blood cells, the inventors added the vectors to peripheral blood mononuclear cell (PBMC) in vitro. PBMCs were infected either immediately after their in vitro isolation, or following an overnight culture in the presence of IL-7 aiming at maintaining the viability of naive lymphocytes (FIG. 12A). After the infection step, cells were cultured in the presence of IL-7 to support cell viability for at least 3 days. Globally, transgene expression was low on the total nucleated cell population expressing CD45 (Supplementary Table S1). However, significantly higher amounts of cells were transduced in the presence of VF1 compared to mock controls without vector (Supplementary Table S1). The effects of LV-Syn1 were comparable to those of VSVg. Cells that had been preactivated with IL-7 were better transduced than cells infected immediately upon isolation.

SUPPLEMENTARY TABLE S1

Transduction of whole PBMC with LV-Syn1 and LV-Syn2 in the presence of Vectofusin-1

|  | No vector | | LV-Syn1 | | LV-Syn2 | | LV-VSVg | |
|---|---|---|---|---|---|---|---|---|
| VF1 | − | + | − | + | − | + | − | + |
| | | | Prior activation with IL-7 | | | | | |
| Average ± SD | 0.1 ± 0.1 | 0.3 ± 0.2 | 1.0 ± 0.1 | 12.7 ± 14.6[&] | 1.7 ± 1 | 4.5 ± 2.7[&] | 5.9 ± 7.8[&] | 5.4 ± 1[&] |
| n | 9 | 7 | 3 | 9 | 3 | 7 | 9 | 6 |
| | | | Non-activated PBMC | | | | | |
| Average ± SD | 0.2 ± 0.2 | 0.7 ± 0.7 | 2.7 ± 3.3 | 5.7 ± 6.7[&] | 1.4 ± 1.6 | 0.8 ± 0.5 | 4.0 ± 2.0[&] | 6.0 ± 2.5[&] |
| n | 6 | 6 | 2 | 6 | 2 | 6 | 6 | 6 |

Legend:
Average percentage ± SD of total nucleated cells (CD45+) expressing GFP, 3 days after infection of PBMC. The cells were preactivated with IL-7 or not as indicated, and were transduced with indicated LV in the presence or absence of Vectofusin-1 (VF1) additive. PBMC were obtained from different donors and the number of donors (n) tested is indicated.
[&] $p < 0.05$ compared to "no vector" in a paired Student's t test PBMC contain multiple subsets of cells in different proportion. As shown in FIG. 3 and Table 2, transgene expression was found in a large proportion of CD19+ B lymphocytes and CD11c+ myeloid/dendritic cells (which are a minority in PBMC) whereas only a fraction of CD3+ T cells (which are more abundant in PBMC) were marked in agreement with the overall low results of transduction obtained in CD45+ cells. An average of 59% each of CD19+ cells or of CD11c+ cells were transduced by LV-Syn1 following a pre-activation with IL-7 (Table 2). As observed with 293T and BeWo cells, adding VF1 was necessary to achieve PBMC transduction as few cells were transduced in the absence of this additive. The VF1 peptide also enhanced the transduction of PBMC by LV-VSVg.

TABLE 2

Transduction of human peripheral blood cell subsets with the syncytin-pseudotyped LV

| | CD19+ B cells | CD3+ T cells | CD11c+ myeloid cells |
|---|---|---|---|
| no activation | | | |
| PBS | 0.0 ± 0 | 0.1 ± 0.1 | 0.2 ± 0.3 |
| LV-Syn1 | 2.3 ± 4.3 | 1.3 ± 2.6 | 5.5 ± 6.3 |
| LV-Syn2 | 0.6 ± 0.4 | 0.4 ± 1.0 | 0.2 ± 8.2 |
| LV-VSVg | 3.6 ± 5.0 | 2.8 ± 2.9 | 11.5 ± 3.5 |
| VF1 | 3.3 ± 4.0 | 0.24 ± 0.2 | 7.8 ± 8.4 |
| LV-Syn1 + VF1 | 35.7 ± 24 | 3.61 ± 3.6 | 57.7 ± 11 |
| LV-Syn2 + VF1 | 22.2 ± 26 | 1.49 ± 1.9 | 35.5 ± 34 |
| LV-VSVg + VF1 | 27.6 ± 17 | 0.97 ± 0.6 | 45.2 ± 16 |
| IL-7 activation | | | |
| PBS | 0.3 ± 0.4 | 0.5 ± 0.4 | 0.8 ± 0.6 |
| LV-Syn1 | 2.1 ± 2.6 | 0.8 ± 0.3 | 4.1 ± 6.0 |
| LV-Syn2 | 1.8 ± 1.5 | 1.5 ± 1.0 | 2.2 ± 2.2 |
| LV-VSVg | 2.6 ± 1.6 | 1.3 ± 0.6 | 2.4 ± 0.8 |
| VF1 | 0.8 ± 0.5 | 0.18 ± 0.2 | 0.25 ± 0.5 |
| LV-Syn1 + VF1 | 59.3 ± 23 | 11.2 ± 19 | 59.2 ± 18 |
| LV-Syn2 + VF1 | 44.0 ± 24 | 6.1 ± 10 | 40.1 ± 15 |
| LV-VSVg + VF1 | 32.1 ± 18 | 3.5 ± 1.4 | 35.1 ± 10 |

Legend: Human PBMC were transduced with the indicated vectors and with or without Vectofusin-1 (VF1) in steady-state conditions (no activation) or following a short overnight pre-activation with IL-7, the subsequently cultured with IL-7 for 3 days. Transduction results are expressed as the average percentage ± SD of cells positive for GFP in CD3+ (T cells), CD19+ (B cells) or CD11c+ (dendritic myeloid cells) cells in culture, 3 days after infection. Data represent 3 separate experiments without VF1 and 8 to 9 separate experiments in the presence of VF1.

Remarkably, it was possible to transduce non-activated CD19+ cells suggesting that truly naïve cells can be targeted by syncytins. Various subsets of CD19+B cells have been characterized (Kaminski et al, 2012) including naïve CD19+ CD27-IgD+ cells (50-70% of the population); memory non-switched CD19+ CD27+ IgD+ cells (15-20% of the population); memory switched CD19+ CD27+ IgD− IgM− cells (2-5% of the population); memory switched IgM only CD19+ CD27+ IgD-IgM+ cells (2-5% of the population) and plasmablasts CD19+ CD27hi (1-2% of the population). The FACS gating strategies following infection of PBMC are shown in FIG. 12B. Overall, both naïve and memory B cell subsets were effectively transduced with the syncytin-pseudotyped vectors regardless of prior activation (FIG. 3). In greater detail, all memory B cell subsets were found to be transduced in the absence of prior activation (Table 3). In such non-activated conditions, syncytin-pseudotyped vectors transduced B cells more effectively than LV-VSVg suggesting a specific tropism of the syncytins for these cells. The B cell transducing effects of LV-Syn1 and LV-Syn2 were found to be vector concentration dependent (FIG. 4) and transgene independent. Almost all peripheral blood CD19+ cells could be transduced using $10^6$ TU/mL of LV-Syn1 or LV-Syn2 vectors encoding either GFP or ΔNGFR thereby providing a very effective system to express various types of heterologous proteins in these cells.

TABLE 3

Percentage of transduction of B cells subsets

| | Naïve | Memory non-switch | Memory IgM only | Memory switched | Plasmablasts |
|---|---|---|---|---|---|
| PBS | 0.2 ± 0.3 | 0.0 ± 0 | 0.3 ± 0.5 | 0.5 ± 1 | 0.3 ± 0.6 |
| VF1 | 0.6 ± 0.5 | 1 ± 0.1 | 0 ± 0 | 0.3 ± 0.5 | 0.3 ± 0.6 |

TABLE 3-continued

Percentage of transduction of B cells subsets

|  | Naive | Memory non-switch | Memory IgM only | Memory switched | Plasmablasts |
|---|---|---|---|---|---|
| LV-Syn1 | 0.4 ± 1.1 | 1 ± 0.9 | 0.2 ± 0.3 | 0 ± 0 | 0.3 ± 0.6 |
| LV-Syn1 + VF1 | 62 ± 26 | 23 ± 3.3 | 16 ± 13 | 41 ± 11 | 32 ± 13 |
| LV-Syn2 | 1 ± 0.1 | 4 ± 5.2 | 5 ± 6 | 4 ± 5.3 | 1.00 ± 1.4 |
| LV-Syn2 + VF1 | 52 ± 29 | 29 ± 15 | 27 ± 34 | 26 ± 30 | 29 ± 8.5 |
| LV-VSVg | 0.1 ± 0.1 | 9 ± 8.4 | 4 ± 4 | 10 ± 16 | 2 ± 1.1 |
| LV-VSVg + VF1 | 14 ± 14 | 18 ± 16 | 12 ± 11 | 20 ± 11 | nd |

Legend: Human PBMC were transduced in steady-state conditions with LV-Syn1 or LV-Syn2 (1E10$^5$ TU/mL) or LV-VSVg (1E10$^7$ TU/mL). Results are the average percentage ± SD of cells positive for GFP in the indicated populations defined as naive B cells (CD3−, CD19+, CD27−, IgM+, IgD+ cells); memory non-switch B cells (CD3−, CD19+, CD27+, IgM+, IgD+ cells); memory IgM only B cells (CD3−, CD19+, CD27+, IgM+, IgD− cells); memory switched B cells (CD3−, CD19+, CD27+, IgM−, IgD−) and plasmablasts (CD3−, CD19+, CD27high), 3 days after infection. Data represent 2 to 3 separate experiments with 1 to 2 different donor per experiment. nd = not determined because too few cells to analyze in the gate.

Functional B Cells are Stably Transduced with Syncytin-Pseudotyped Vectors

To exclude that the observed effects were non-specific, caused by pseudo-transduction or by artefactual auto-fluorescence of Vectofusin-1 which can occur upon aggregation (Fenard et al 2013) the inventor verified proviral integration in cells treated with the vector and cultured over time. Following addition of the vector to the cells, the inventors added CD40L and IL-4 to activate and expand the culture for 8-14 days. In such cultures, the inventors detected vector copies specifically when vectors were added together with Vectofusin-1 (Table 4) even though conditions were not optimal to ensure the survival of all cells. In addition, using B cell-activation signals such as CD40 ligand (CD40L) and IL-21 previously reported to be essential for the development of memory B cells (Recher et al 2011), the inventors confirmed that transduced B cells could be activated efficiently (Table 5). Using CFSE marking and flow cytometry to detect B cell division and transgene expression, the inventors confirmed the marking of cells capable of responding to CD40L and IL-21 and with activated B cell, including plasmablast, phenotype (Table 5). To further confirm the transduction of functional B cells, the inventors used EBV to transform PBMC immediately after they had been infected with the LV-Syn1 vector and obtained lymphoblastic cells containing stably integrated vector sequences (Table 4). These results confirm that the syncytin vectors can stably transduce primary B cells that retain functional ability to proliferate and be expanded.

TABLE 4

Functional B cells are stably transduced by syncytin-pseudotyped LV

| | VCN | |
|---|---|---|
| CD40L + IL-4 | Experiment 1 (Day 13) | Experiment 2 (Day 7) |
| PBMC | 0.0 | 0.0 |
| PBMC + VF1 | 0.0 | 0.0 |
| PBMC + LV-Syn1 + VF1 | 3.8 | 0.4 |
| PBMC + LV-Syn2 + VF1 | 0.3 | 0.0 |
| PBMC + LV-VSVg | 0.2 | 0.1 |
| PBMC + LV-VSVg + VF1 | 0.2 | 0.0 |

| | VCN | |
|---|---|---|
| EBV | Experiment 1 (Day 14) | Experiment 2 (Day 14) |
| PBMC | 0 | 0; 0; 0 |
| PBMC + VF1 | 0 | not done |
| PBMC + LV-Syn1 + VF1 | 0.5 | 0.02; 0.06; 0.2 |
| PBMC + LV-Syn2 + VF1 | not done | 0.02; 0.02; 0.2 |
| PBMC + LV-VSVg | 0.05 | not done |

Legend: PBMC were activated with IL-7 and transduced in the indicated conditions, then cultured for 6-13 days in the presence of CD40L and IL4 (top table) or incubated with EBV and cyclosporin A for immortalization using standard procedures and cultured for 2 weeks (bottom table). At the indicated times, genomic DNA was extracted from the culture and the average number of integrated vector copy per cell (VCN) was measured by qPCR. In experiment 2 of EBV transformation, results are shown with 3 different blood donors.

TABLE 5

In vitro activation of transduced primary CD19+ B cells

| | Day 3 | | | | Day 6 | | | |
|---|---|---|---|---|---|---|---|---|
| | IL-21 | | IL-21 + CD40L | | IL-21 | | IL-21 + CD40L | |
| | LV-Syn1 | LV-Syn2 | LV-Syn1 | LV-Syn2 | LV-Syn1 | LV-Syn2 | LV-Syn1 | LV-Syn2 |
| % NGFR+ B cells | 37.2 ± 5.3 | 60.2 ± 8 | 26.8 ± 9.4 | 45.8 ± 11.5 | 39.8 ± 9.4 | 45.3 ± 6.9 | 17.3 ± 2.7 | 23.3 ± 6.8 |
| % NGFR+ B cells in CFSE division | 25.2 ± 15.7 | 16.7 ± 6 | 77.5 ± 16.4 | 82.3 ± 10 | 28.8 ± 12.8 | 28.7 ± 14.1 | 93.2 ± 3.4 | 93.5 ± 4 |
| % NGFR− B cells in CFSE division | 35.3 ± 16.7 | 34.2 ± 17 | 85.8 ± 7.4 | 91.0 ± 4.4 | 40.5 ± 18.9 | 31.7 ± 8.6 | 94.8 ± 1.2 | 95.2 ± 1.5 |
| % plasmablast on NGFR+ B cells | 4.4 ± 1.8 | 5.7 ± 2.7 | 13.6 ± 4.8 | 14.1 ± 5.2 | 17.8 ± 13.1 | 18.2 ± 11.2 | 29.8 ± 13.1 | 28.9 ± 12.2 |

TABLE 5-continued

In vitro activation of transduced primary CD19+ B cells

| | Day 3 | | | | Day 6 | | | |
| --- | --- | --- | --- | --- | --- | --- | --- | --- |
| | IL-21 | | IL-21 + CD40L | | IL-21 | | IL-21 + CD40L | |
| | LV-Syn1 | LV-Syn2 | LV-Syn1 | LV-Syn2 | LV-Syn1 | LV-Syn2 | LV-Syn1 | LV-Syn2 |
| % plasmablast on NGFR− B cells | 4.7 ± 1.2 | 6.0 ± 3.0 | 15.8 ± 5.7 | 14.5 ± 5.6 | 20.8 ± 14.1 | 16.3 ± 12 | 32.7 ± 15 | 30.2 ± 10.9 | n = 6 different healthy donors
Legend.
PBMCs were labeled with 2 μM CFSE, transduced with Lv-Syn1-2 NGFR, and cultured in the absence or presence of CD40Ligand [2 μg/mL] and IL-21 [50 ng/mL] After 3 and 6 days culture, B cell transduction (ie, NGFR expression), B cell proliferation (ie, CFSE dilution) and the frequency of CD19+ CD27++ plasmablasts were determined by flow cytometry.

Transduction of Murine Primary B Cells

Freshly-isolated murine spleen cells were cultured with LV-Syn1 or LV-SYn2 vectors encoding ΔNGFR for 3 days. As shown in FIG. 17 this resulted in a very efficient transduction of CD19+B cells. In these cultures, much fewer CD19− cells were transduced in proportion, thus confirming the particular tropism of the syncytin-pseudotyped vectors for B cells in mice as in humans. The data also show that the syncytin-1 and syncytin-2 glycoproteins recognize murine counterparts and these findings will facilitate future preclinical studies with these vectors.

Transduction of CD11c+ Cells

Figure 13:
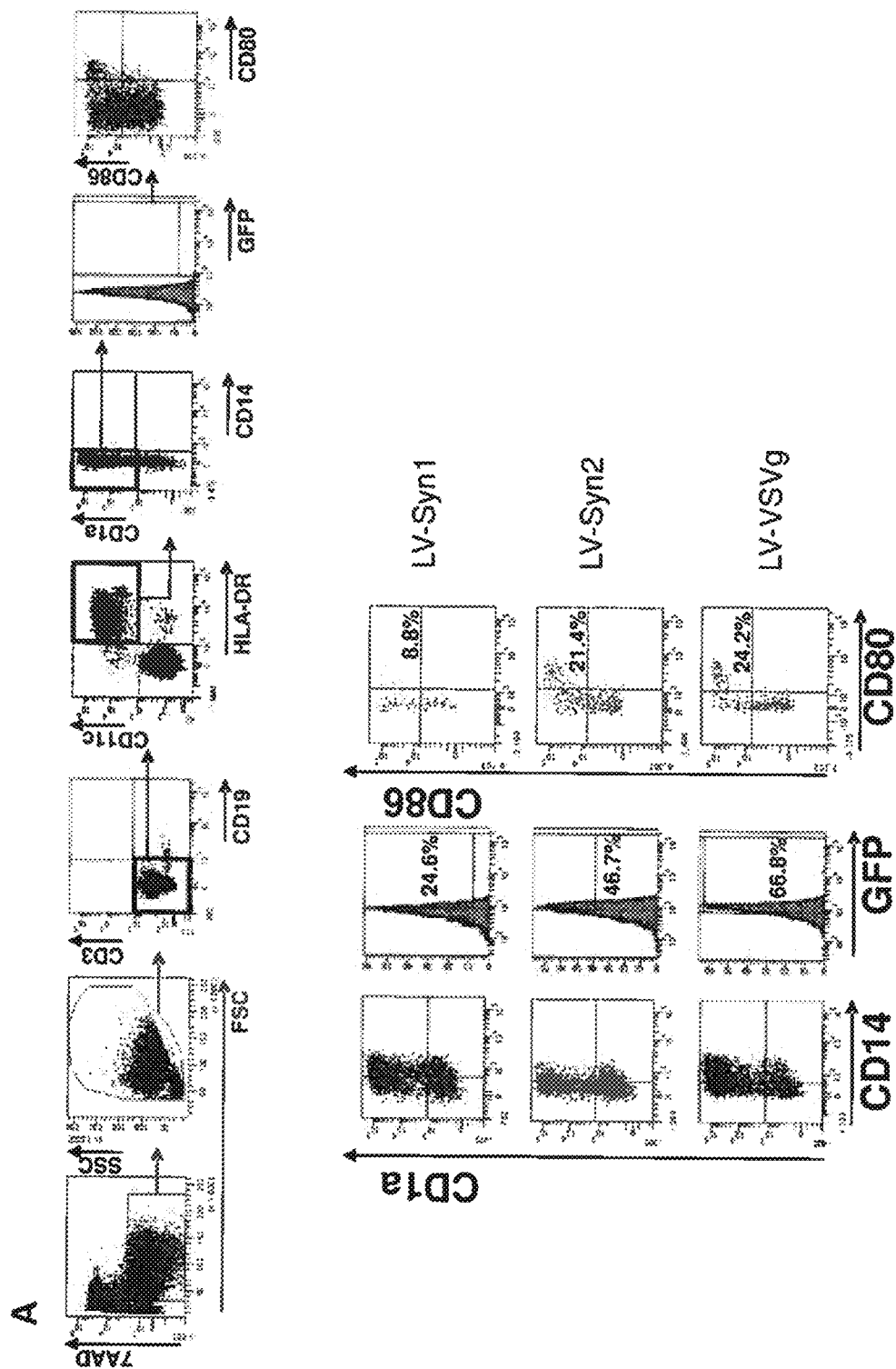
Figure 13:
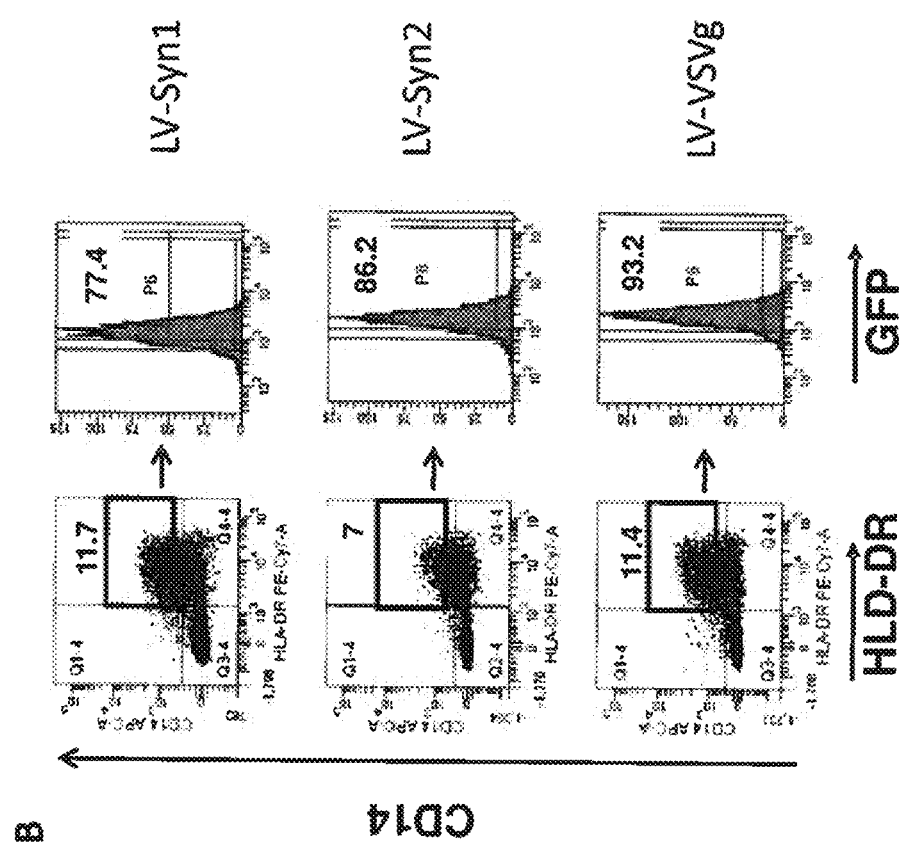

As seen in FIG. 3, a large proposition of CD19− CD3− CD11c+ cells was transduced with LV-Syn1 and LV-Syn2 from PBMC without prior activation and in the presence of Vectofusin-1. Further phenotyping showed that such CD11c cells also expressed high levels of HLA-DR and were transduced effectively with the syncytin-pseudotyped vectors (FIG. 5). The cells were grown in GM-CSF+IL-4, expressed CDIa, CD80, CD86 and lacked CD14, suggesting that they were immature dendritic cells (FIG. 13A). In addition, CD14+ HLA-DR+ cells which have the phenotype of monocytic cells are also transduced (FIG. 13B). Thus, both LV-Syn1 and LV-Syn2 can be used effectively to express a transgene in antigen presenting cells.

LV-Syn1 and LV-Syn2 Vectors do not Efficiently Transduce Primary Human T Cells

Peripheral blood T cells were not efficiently transduced by the syncytin-pseudotyped LV, although some cells could be transduced upon activation. Following prior activation with IL-7, a small proportion of peripheral blood T cells was transduced with LV-Syn1 or LV-Syn2 vectors but these effects were not consistent from experiment to experiment (FIG. 3 and Table 2). Without prior activation, transduction levels were always low.

Thus, differential transduction of blood cell subsets is observed with syncytin-pseudotyped vectors.

Expression of the ASCT2 and MFSD2a Receptors on Blood Cell Subsets and Cell Lines ASCT2 and MFSD2a which are respectively the entry receptors for syncytin-1 and syncytin-2 were detected on the cell surface of blood cell subsets using and indirect immunofluorescence detection (FIG. 6A). The highest percentage of cells expressing these markers were CD19+ and CD11c+ cells, whereas T cells expressed lower levels of these receptors (FIG. 6B).

These results were confirmed by qRT-PCR, which show for the first time that human B cells express MFSD2a and ASCT2 (FIG. 6-C). Expression of ASCT2 and MFSD2a was also found on 293T cells whereas it was at a much lower level of HCT1 16 cells which are not transduced with the vectors (FIG. 14). On cells tested, the expression of the receptors correlated well with the transduction levels that were achieved.

Human B and T Cell Lines are Transduced with Syncytin-Pseudotyped Vectors

To extend the results obtained on primary cells and to further assess the cellular specificity of the syncytin-pseudotyped vectors, the inventors attempted to transduce a panel of human cell lines. The Burkitt's lymphoma Raji B cells and Jurkat T cells were tested. Raji B cells could be transduced with the Syncytin-pseudotyped vectors (FIG. 15). The highest levels obtained in Raji cells using $2\times10^6$ TU/mL of LV-Syn2 vector reached 16% (as opposed to >90% reached with $10^6$TU/mL in primary B cells as seen in FIG. 4). The inventors verified that Raji cells were permissive for transduction with LV because 88% transduction of Raji cells were transduced with $10^8$TU/mL LV-VSVg (control of FIG. 15, not shown). In one experiment, transduced Raji cells were sorted by flow cytometry and cultured for 49 days, demonstrating the stable integration of the transgene for prolonged periods of time (Supplementary Table S2). Jurkat T cells were partially transduced with syncytin-pseudotyped vectors (FIG. 15). Thus syncytin-pseudotyped LV can be used as gene transfer tools for some cell lines. In B cells, transduction appears to be more effective in primary cells than with established B cell lines.

SUPPLEMENTARY TABLE S2

Stable transduction of Raji cells with Syncytin-pseudotyped vectors

| | % GFP+ cells | | VCN | |
| --- | --- | --- | --- | --- |
| Vector | Sorted GFP− cells | Sorted GFP+ cells | Sorted GFP− cells | Sorted GFP+ cells |
| LV-Syn1 | 0 | 72.8 | 0 | 1.003 |
| LV-Syn2 | 0 | 93.8 | 0.001 | 1.017 |
| LV-VSVg | 0.3 | 86.3 | 0.116 | 6.177 |

Legend: Three different GFP-encoding vectors were used at the concentration of $1.2\ 10^5$ TU/mL to infect Raji cells in the presence of Vectofusin-1 (12 μg/mL). After 2 weeks, the expression of GFP was 2.5% with LV-Syn1, 5% with LV-Syn2, and 100% with LV-VSVg vector. After 30 days, cells expressing GFP (GFP+) or not (GFP−) were sorted by flow cytometry and these sorted cells were cultured until day 49 to measure GFP expression by FACS and the average vector copy number per cell (VCN) by qPCR.

Functional Correction in a Primary Immune Deficit

Severe combined immunodeficiency type −1 (SCIDXI) is an X-linked primary immunodeficiency which is caused by mutations in the interleukin 2-receptor gamma chain (IL2Rg) gene. Allogeneic bone marrow transplantation can cure the disease but some patients remain incompletely corrected with only partial chimerism in B cells (Recher et al 2011). Patients with less than 5% B cell chimerism remain incapable of maturing and producing immunoglobulins. Their B cells remain incapable of becoming mature memory IgG secreting B cells. Indeed, it was found recently that IL2Rg is also the receptor for IL-21 providing essential signals for the maturation of B cells (Recher et al 2011). Several gene therapy trials have been attempted to treat this disease using IL2Rg gene transfer in hematopoietic stem and progenitor cells. However, without conditioning of the patient, the gene-corrected cells only produce corrected T cells and B cells remain uncorrected as shown in the most recent gene therapy trial (Hacein-Bey-Abina et al 2014). As a result, such patients B cells are non-functional and patients remain dependent upon immunoglobulin infusion to prevent infections. This prompted the inventors to ask if syncytin-pseudotyped vectors could be used to transfer IL2Rg to peripheral B cells in patients who have been incompletely corrected by gene therapy. Cells from a patient were obtained. The patient blood mononuclear cells were found to contain CD3+ IL2Rg+ T cells but contrary to healthy individuals, the patient blood CD19+B cells did not express the maturation marker CD27, did not express IL2Rg (FIG. 7 A and B) and did not produce IgG (Table 6). Upon gene transfer with LV-syncytinl vectors encoding the IL2Rg, patients cells were able to respond to CD40L+IL-21 by producing IgG in medium, even though activation markers were not detected on the cells, probably due to the high level of mortality of these fragile cells in culture. These results demonstrate that peripheral blood B cells can be targeted by gene transfer to provide some functional correction in SCIDX 1 and that syncytin-pseudotyped LV are useful tools for this application.

In Vivo Experiments

The efficient transduction of primary human B cells by LV-Syn1 prompted to test if this vector functioned in vivo. Immunodeficient NSG mice were first engrafted with $10^7$ PBMC per mouse and the next day received a single bolus of LV-Syn1 intravenously. After 7 days, mice were sacrificed and different tissues were examined. In 2 mice out of 3, the inventors found the presence of CD45+ CD19+ human B cells in the spleen in which a small proportion (3-15%) expressed GFP suggesting that they had been transduced in vivo (FIG. 16). These preliminary results suggest the possibility of using syncytin-pseudotyped vectors to target human B cells in vivo.

EXAMPLE 2

Murine Syncytin-A and In Vivo Gene Delivery in Mice with LV-SynA. Production of Stable and Infectious LV-SynA Particles Materials and Methods (See Also Materials and Methods for Example 1)

Cloning of Syncytin A and production of LV-Syn A.

a. Generation of a plasmid expressing murine Syncytin-A.

The cloning of the murine syncytin-A cDNA into the HindIII and XbaI sites of the pcDNA3.1 eukaryotic expression plasmid was performed by inserting a PCR-amplified fragment from the pUC-SynA plasmid generated by Genecust (Ellange, Luxembourg) and which contains the Syn-A murine gene full-length cDNA (Ensembl reference ENSMUSG00000085957) using the following primers forward 5' AGCAAGCTTATGGTTCGTCCTTGG 3' (SEQ ID NO:32) (Tm=69,8° C.; % GC=50%; Sigma, Saint-Louis, USA) and reverse 5' AGCTCTAGACTAGACGG-CATCCTC 3' (SEQ ID NO:33) (Tm=65° C.; % GC=54%; Sigma) and ligation. The plasmid was verified by sequencing (Beckman Coulter Genomics, Takeley, UK).

b. Production of Syn-A-pseudotyped lentiviral vectors.

HEK293T cells plated in T175 cm2 flasks in DMEM+ 10% fetal calf serum (FCS) were co-transfected with the following 4 plasmids (quantities per flask): pKLgagpol (14.6 µg), pKRev (5.6 µg), pcDNA3.1-SynA (20 µg), and transfer plasmid either PRRL-SFFV LucII or pRRL-SFFV-LucII-2A-ΔNGFR-WPRE (22.5 µg). After 24 hours, the cells are washed and fresh medium is added. The following day, medium is harvested, clarified by centrifugation 1500 rpm for 5 min and filtered 0.45 m, then concentrated by ultra-centrifugation 50000 g for 2 h at 12° C. and stored at −80° C. until used.

c. Titration of Syncytin-A-pseudoptyped LV.

Physical titer was determined by p24 ELISA as for other types of LV. Infectious titer was determined as infectious genome titer (IG/mL) using the murine lymphoma cell line A20. Serial dilutions of vector are added to A20 cells in the presence of Vectofusin-I® (12 µg/µL) for 6 hours. Medium is renewed and cells are incubated for 7 days and genomic DNA is obtained to measure vector copy number per cells using duplex qPCR on iCycler 7900HT (Applied Biosystems) with the primers: PSI forward 5'CAGGA-CTCGGCTTGCTGAAG3' (SEQ ID NO:34), PSI reverse 5'TCCCCCGCTTAATACTGACG3' (SEQ ID NO:35), and a PSI probe labeled with FAM (6-carboxyfluoresceine) 5'CGCACGGCAAGAGGCGAGG3' (SEQ ID NO:36), Titin forward 5'AAAACGAGCAGTGACGTGAGC3' (SEQ ID NO:37), Titin reverse 5'TTCAGTCATGCTGC-TAGCGC3' (SEQ ID NO:38) and a Titin probe labeled with VIC 5'TGCACGGAAGCGTCTCGTCTCAGTC3' (SEQ ID NO:39).

In vivo bioluminescent gene transfer in mice.

LV-SynA encoding LucII vector was produced and $5×10^5$ TU of vector were injected intravenously into albinos C57Bl/6 mice. Controls included LV-VSVg encoding LucII and PBS. For the detection of bioluminescence, mice were anesthetized with ketamine (100 mg/kg)/xylasine (10 mg/kg), and 100 µL of 150 µg/mL D-luciferin was administered intra-peritoneally and imaged 10 min later with a CCD camera ISO14N4191 (IVIS Lumina, Xenogen, MA, USA). A 3 min bioluminescent image was obtained using 15 cm filed-of-view, binning (resolution) factor 4, 1/f stop and open filter. Region of interest (ROIs) were defined manually (using a standard area in each case), signal intensities were calculated using the living image 3.0 software (Xenogen) and expressed as photons per second. Background photon flux was defined from an ROI drawn over the control mice or control muscle where no vector had been administered.

Results

Murine Syncytins were explored for in vivo applications. Syncytin A is non-orthologue but functionally similar murine counterpart to human Syncytins-1 and -2 (Dupressoir et al 2005).

We cloned the murine SynA into an expression plasmid and used it to produce lentiviral vector particles. We found that SyncytinA can successfully pseudotype rHIV-derived LV. We used the same conditions already defined for the production of human syncytin-pseudotype LV (22 Ug DNA per plate, one harvest only) to generate stable LV-SynA. LV-Syn A were very efficient at transducing the murine A20 B lymphoma cell line in the presence of VF1 (Figure S8) (Supplementary table S4). We found that SynA was as efficient as its human counterparts to transduce primary non-activated murine B cells in vitro. As seen in FIG. 8 and FIG. 9 LV-SynA were capable of transducing without pretreatment murine B cells from spleen (FIG. 8) and from bone marrow (FIG. 9). These experiments also show that murine T cells can be transduced as well. The transduction of B220 low cells suggests that immature B cells were transduced and can be targeted for biological applications. Interestingly, it was possible to transduce human CD19+B cells with LV pseudotyped with the murine syncytin A (supplementary table S5)

LV-Syn A proved to be efficient for gene delivery in vivo in mice. FIG. 10 shows the bioluminescent detection of the transgene 16 days after injection of a LV-SynA vector encoding Lucli. The vector was injected through the mice tail vein and the inventors did not use vectofusin for this. The presence of vector in the spleen CD45+ CD19+ cells was confirmed by purifying spleen cells by flow cytometry cell sorting and measuring the levels of transduction by q-PCR (supplementary table S3). Thus, Syncytins are unique tools to mediate entry into human and murine B cells in vitro and in vivo.

SUPPLEMENTARY TABLE S3

In vivo delivery of the LucII transgene with LV-SynA.
Vector copy number

| Whole spleen | Spleen CD45 cells | Spleen CD45+ 19+ cells |
|---|---|---|
| 0.039 | 0.002 | 0.039 |

Legend: the table shows the vector copy number obtained on cell subpopulations obtained by flowcytometry cell sorting of spleen cells using CD45 and CD19 antibodies. CD45− cells represent stromal cells of non-hematopoietic origin. CD45+ CD19+ cells are B cells.

SUPPLEMENTARY TABLE S4

Infectious titration of Lv-SynA on the murine B lymphoma cell line A20.

| | n | Titer ng P24/mL | Titer TU/mL | Titer GI/mL |
|---|---|---|---|---|
| SynA | 10 | $1.74 \cdot 10^5$ | $7.1 \cdot 10^6$ | $1.3 \cdot 10^6$ |
| | 10 | $2.3 \cdot 10^5$ | $1.98 \cdot 10^7$ | $4.72 \cdot 10^6$ |
| LV-VSVg | 1 | $5.23 \cdot 10^5$ | $2.1 \cdot 10^7$ | — |

Legend: different LV-SynA and LV-VSVg productions and titers obtained in physical particles (ng p24/mL) and infectious particles (TU/mL and GI/ML). TU: transduction unit, GI: infectious genome.

SUPPLEMENTARY TABLE S5

Transduction of human CD19+
B cells with syncytin-A-pseudotyped LV.

| CD19+ B ells | Conditions | nb copies |
|---|---|---|
| donor 1 | Non transduced | 0.04 |
| | LV-SA LucII | 9.4 |
| | LV-S1 NGFR | 3.6 |
| donor 2 | Non transduced | 0.1 |
| | LV-SA LucII | 1.9 |
| | LV-S1 NGFR | 1.1 |
| donor 3 | Non transduced | 0.05 |
| | LV-SA LucII | 3.7 |
| | LV-S1 NGFR | 2.0 |

Legend: Human peripheral blood CD19+ B cells were obtained from 3 separate blood donors, and were prepared by Ficoll separation of the mononuclear cells followed by positive selection of CD19+ B cells using magnetic beads and the Miltenyi AutoMacs system. CD19+ cells were incubated in the indicated conditions, using various preparations of LV pseudotyped with syncytin A, or syncytin 1 and expressing different transgenes. We used 2 μL of concentrated vector on the cells in the presence of Vectofusin-1 (12 μg/mL). Cells were washed after 6 hours and cultured for 4 days before measuring the number of integrated vector copies per cell using a duplex qPCR as described in (Merten et al. 2011).

EXAMPLE 3

Physical Titers Determination: Correspondence Between Physical Titer Obtained by p24 RT ELISA and by Direct Particle Counting with an Automated Counter Physical titers were determined by 2 different methods for HIV-1-derived lentiviral vectors (LV) pseudotyped with syncytin-1 (S1), syncytin-2 (S2), syncytin A (SA) or with VSVg, and encoding either the truncated form of the nerve growth factor receptor (ΔNGFR) or the green fluorescent protein (GFP). The LV were produced by transient transfection, concentrated by ultracentrifugation and cryopreserved a −80° C. before titration.

The methods consisted either of (a) an ELISA measuring the p24 concentration in the sample followed by a calculation of the titer as physical particles (pp) assuming that 1 fg of p24 corresponds to 12 pp of LV (Farson ef al, 2001) or (b) using the NS300 Nanosight particle counter from Malvem Instruments (UK) which directly measures the particle concentration in the sample using automated microscopy.

SUPPLEMENTARY TABLE S6

| Vectors | Titer pp/mL ELISA P24 | Titer pp/mL Nanosight |
|---|---|---|
| LV-S1-DNGFR | $9.6 \cdot 10^{12}$ | $7.1 \cdot 10^{11}$ |
| LV-S2-DNGFR | $6 \cdot 10^{12}$ | $1.4 \cdot 10^{12}$ |
| LV-SA Luc2-2A-DNGFR | $2.8 \cdot 10^{12}$ | $9.9 \cdot 10^{11}$ |
| LV-SA-DNGFR | $2.4 \cdot 10^{12}$ | $7.7 \cdot 10^{11}$ |
| LV-S2-DNGFR | $9.4 \cdot 10^{11}$ | $5 \times 10^{11}$ |
| LV-S1-DNGFR | $1.6 \times 10^{11}$ | $1.8 \times 10^{11}$ |
| LV-SA-Luc2 | $4.4 \times 10^{11}$ | $3.1 \times 10^{11}$ |
| LV-VSVg-DNGFR | $1.6 \cdot 10^{12}$ | $8.9 \cdot 10^{11}$ |

On average, a conversion factor between the titer pp/mL (ELISA P24) and the titer pp/mL (Nanosight) obtained as a [(mean titer ELISA P24)/(mean titer Nanosight)] is about 3.7, i.e. about 4.

REFERENCES

An DS, Xie Y, Chen I S (2001). Envelope gene of the human endogenous retrovirus HERV-W encodes a functional retrovirus envelope. *Journal of virology* 75: 3488-3489.

Antony J M, Ellestad K K, Hammond R, Imaizumi K, Mallet F, Warren K G et al (2007). The human endogenous retrovirus envelope glycoprotein, syncytin-1, regulates neuroinflammation and its receptor expression in multiple sclerosis: a role for endoplasmic reticulum chaperones in astrocytes. *Journal of immunology* 179: 1210-1224.

Biffi A (2015). Gene therapy for lysosomal storage disorders: a good start. *Human molecular genetics*.

Blaise S, de Parseval N, Benit L, Heidmann T (2003). Genomewide screening for fusogenic human endogenous retrovirus envelopes identifies syncytin 2, a gene conserved on primate evolution. *Proceedings of the National Academy of Sciences of the United States of America* 100: 13013-13018.

Blaise S, Ruggieri A, Dewannieux M, Cosset F L, Heidmann T (2004). Identification of an envelope protein from the FRD family of human endogenous retroviruses (HERV-FRD) conferring infectivity and functional conservation among simians. *Journal of virology* 78: 1050-1054.

Blaise S, de Parseval N, Heidmann T (2005). Functional characterization of two newly identified Human Endogenous Retrovirus coding envelope genes. *Retrovirology* 2: 19.

Blond J L, Lavillette D, Cheynet V, Bouton O, Oriol G, Chapel-Fernandes S et al (2000). An envelope glycoprotein of the human endogenous retrovirus HERV-W is expressed in the human placenta and fuses cells expressing the type D mammalian retrovirus receptor. *Journal of virology* 74: 3321-3329.

Charrier S, Ferrand M, Zerbato M, Precigout G, Viornery A, Bucher-Laurent S et al (2011). Quantification of lentiviral vector copy numbers in individual hematopoietic colony-forming cells shows vector dose-dependent effects on the frequency and level of transduction. *Gene therapy* 18: 479-487.

Cheynet V, Ruggieri A, Oriol G, Blond J L, Boson B, Vachot L et al (2005). Synthesis, assembly, and processing of the Env ERVWEI/syncytin human endogenous retroviral envelope. *Journal of virology* 79: 5585-5593.

Cire S, Da Rocha S, Yao R, Fisson S, Buchholz C J, Collins M K et al (2014). Immunization of mice with lentiviral vectors targeted to MHC class II+ cells is due to preferential transduction of dendritic cells in vivo. *PloS one* 9: e101644.

Cornelis G, Heidmann O, Degrelle S A, Vernochet C, Lavialle C, Letzelter C, et al (2013). Captured retroviral envelope syncytin gene associated with the unique placental structure of higher ruminants PNAS 110(9): E828-E837.

Dewannieux M, Blaise S, Heidmann T (2005). Identification of a functional envelope protein from the HERV-K family of human endogenous retroviruses. *Journal of virology* 79: 15573-15577.

Dewannieux M, Heidmann T (2013). Endogenous retroviruses: acquisition, amplification and taming of genome invaders. *Current opinion in virology* 3: 646-656.

Dupressoir A, Marceau G, Vemochet C, Benit L, Kanellopoulos C, Sapin V et al (2005). Syncytin-A and syncytin-B, two fusogenic placenta-specific murine envelope genes of retroviral origin conserved in Muridae. *Proceedings of the National Academy of Sciences of the United States of America* 102: 725-730.

Esnault C, Priet S, Ribet D, Vernochet C, Bruls T, Lavialle C et al (2008). A placenta-specific receptor for the fusogenic, endogenous retrovirus-derived, human syncytin-2. *Proceedings of the National Academy ofSciences of the United States ofAAmerica* 105: 17532-17537.

Farson D, Witt R, McGuinness R, Dull T, Kelly M, Song et al (2001) A new-generation stable inducible packaging cell line for lentiviral vectors. *Hum Gene Ther.* 20; 12(8):981-97.

Fenard D, Ingrao D, Seye A, Buisset J, Genries S, Martin S et al (2013). Vectofusin-1, a new viral entry enhancer, strongly promotes lentiviral transduction of human hematopoietic stem cells. *Molecular therapy Nucleic acids* 2: e90.

Fischer A, Hacein-Bey Abina S, Touzot F, Cavazzana M (2015). Gene therapy for primary immunodeficiencies. *Clinical genetics* 88: 507-515.

Frecha C, Costa C, Levy C, Negre D, Russell S J, Maisner A et al (2009). Efficient and stable transduction of resting B lymphocytes and primary chronic lymphocyte leukemia cells using measles virus gp displaying lentiviral vectors. *Blood* 114: 3173-3180.

Frese S, Ruebner M, Suhr F, Konou T M, Tappe K A, Toigo M et al (2015). Long-Term Endurance Exercise in Humans Stimulates Cell Fusion of Myoblasts along with Fusogenic Endogenous Retroviral Genes In Vivo. *PloS one* 10: e0132099.

Funke S, Maisner A, Muhlebach M D, Koehl U, Grez M, Cattaneo R et al (2008). Targeted cell entry of lentiviral vectors. *Molecular therapy: the journal of the American Society of Gene Therapy* 16: 1427-1436.

Ghosh S, Thrasher A J, Gaspar H B (2015). Gene therapy for monogenic disorders of the bone marrow. *British journal of haematology*.

Girard-Gagnepain A, Amirache F, Costa C, Levy C, Frecha C, Fusil F et al (2014). Baboon envelope pseudotyped LVs outperform VSV-G-LVs for gene transfer into early-cytokine-stimulated and resting HSCs. *Blood* 124: 1221-1231.

Hacein-Bey-Abina S, Pai S Y, Gaspar H B, Armant M, Berry C C, Blanche S et al (2014). A modified gamma-retrovirus vector for X-linked severe combined immunodeficiency. *The New England journal of medicine* 371: 1407-1417.

Hacein-Bey Abina S, Gaspar H B, Blondeau J, Caccavelli L, Charrier S, Buckland K et al (2015). Outcomes following gene therapy in patients with severe Wiskott-Aldrich syndrome. *Jama* 313: 1550-1563.

Hummel J, Kammerer U, Muller N, Avota E, Schneider-Schaulies S (2015). Human endogenous retrovirus envelope proteins target dendritic cells to suppress T-cell activation. *European journal of immunology* 45: 1748-1759.

Imakawa K, Nakagawa S, Miyazawa T (2015). Baton pass hypothesis: successive incorporation of unconserved endogenous retroviral genes for placentation during mammalian evolution. *Genes to cells: devoted to molecular &cellular mechanisms* 20: 771-788.

Ingrao D, Majdoul S, Seye A K, Galy A, Fenard D (2014). Concurrent measures of fusion and transduction efficiency of primary CD34+ cells with human immunodeficiency virus 1-based lentiviral vectors reveal different effects of transduction enhancers. *Human gene therapy methods* 25: 48-56.

Kaminski D A, Wei C, Qian Y, Rosenberg A F, Sanz I (2012). Advances in human B cell phenotypic profiling. *Frontiers in immunology* 3: 302.

Kichler A, Mason A J, Marquette A, Bechinger B (2013). Histidine-rich cationic amphipathic peptides for plasmid DNA and siRNA delivery. *Methods in molecular biology* 948: 85-103.

Kneissl S, Zhou Q, Schwenkert M, Cosset F L, Verhoeyen E, Buchholz C J (2013). CD19 and CD20 targeted vectors induce minimal activation of resting B lymphocytes. *PloS one* 8: e79047.

Kutner R H, Zhang X Y, Reiser J (2009). Production, concentration and titration of pseudotyped HIV-1-based lentiviral vectors. *Nature protocols* 4: 495-505.

Lavillette D, Marin M, Ruggieri A, Mallet F, Cosset F L, Kabat D (2002). The envelope glycoprotein of human endogenous retrovirus type W uses a divergent family of amino acid transporters/cell surface receptors. *Journal of virology* 76: 6442-6452.

Majdoul S, Seye A K, Kichler A, Holic N, Galy A, Bechinger B et al (2015). Molecular determinants of Vectofusin-1 and its derivatives for the enhancement of lentiviral-mediated gene transfer into hematopoietic stem/progenitor cells. *The Journal of biological chemistry*.

Malassine A, Blaise S, Handschuh K, Lalucque H, Dupressoir A, Evain-Brion D et al (2007). Expression of the fusogenic HERV-FRD Env glycoprotein (syncytin 2) in human placenta is restricted to villous cytotrophoblastic cells. *Placenta* 28: 185-191.

Mangeney M, Renard M, Schlecht-Louf G, Bouallaga 1, Heidmann O, Letzelter C et al (2007). Placental syncytins: Genetic disjunction between the fusogenic and immunosuppressive activity of retroviral envelope proteins. *Proceedings of the National Academy of Sciences of the United States of America* 104: 20534-20539.

Merten O W, Charrier S, Laroudie N, Fauchille S, Dugue C, Jenny C et al (2011). Large-scale manufacture and characterization of a lentiviral vector produced for clinical ex vivo gene 50 therapy application. *Human gene therapy* 22: 343-356.

Nguyen L N, Ma D, Shui G, Wong P, Cazenave-Gassiot A, Zhang X et al (2014). Mfsd2a is a transporter for the essential omega-3 fatty acid docosahexaenoic acid. *Nature* 509: 503-506.

Oburoglu L, Tardito S, Fritz V, de Barros S C, Merida P, Craveiro M el al (2014). Glucose and glutamine metabolism regulate human hematopoietic stem cell lineage specification. *Cell stem cell* 15: 169-184.

Pochini L, Scalise M, Galluccio M, Indiveri C (2014). Membrane transporters for the special amino acid glutamine: structure/function relationships and relevance to human health. *Frontiers in chemistry* 2: 61.

Porter C D, Collins M K, Tailor C S, Parkar M H, Cosset F L, Weiss R A et al (1996). Comparison of efficiency of infection of human gene therapy target cells via four different retroviral receptors. *Human gene therapy* 7: 913-919.

Porter D L, Hwang W T, Frey N V, Lacey S F, Shaw P A, Loren A W el al (2015). Chimeric antigen receptor T cells persist and induce sustained remissions in relapsed refractory chronic lymphocytic leukemia. *Science translational medicine* 7: 303ra139.

Recher M, Berglund U, Avery D T, Cowan M J, Gennery A R, Smart J et al (2011). IL-21 is the primary common gamma chain-binding cytokine required for human B-cell differentiation in vivo. *Blood* 118: 6824-6835.

Renard M, Varela P F, Letzelter C, Duquerroy S, Rey F A, Heidmann T (2005). Crystal structure of a pivotal domain of human syncytin-2, a 40 million years old endogenous retrovirus fusogenic envelope gene captured by primates. *Journal of molecular biology* 352: 1029-1034.

Tolosa J M, Schjenken J E, Clifton V L, Vargas A, Barbeau B, Lowry P et al (2012). The endogenous retroviral envelope protein syncytin-1 inhibits LPS/PHA-stimulated cytokine responses in human blood and is sorted into placental exosomes. *Placenta* 33: 933-941.

The invention claimed is:

1. A method for obtaining stable lentiviral particles pseudotyped with an endogenous retroviral syncytin (ERV syncytin) and packaging a heterologous gene of interest, which have a high physical and/or infectious titer(s), comprising the following steps:

a) transfecting four plasmids in appropriate cell lines, wherein said four plasmids comprise a first plasmid comprising the heterologous gene of interest, a second plasmid comprising the lentiviral rev gene, a third plasmid comprising the gag and pol genes, and a fourth plasmid comprising a nucleotide sequence coding for an envelope glycoprotein, wherein the envelope glycoprotein consists of an ERV syncytin selected from the group consisting of HERV-W, HERV-FRD, murine syncytin-A and murine syncytin-B;

b) incubating the transfected cells obtained in a), so that they produce the stable lentiviral particles pseudotyped with an ERV syncytin, and packaging the heterologous gene of interest;

c) harvesting the stable lentiviral particles obtained in b) 24 hours after the transfection, before fusion of the transfected cells, and d) concentrating the stable lentiviral particles harvested in c) to obtain a preparation of concentrated stable lentiviral particles having a high infectious titer higher than $1 \times 10^6$ TU/mL or a high physical titer higher than $1.5 \times 10^5$ ng p24/mL after freezing and thawing of the preparation.

2. Particles obtained by the method of claim 1.

3. Particles obtained by the method of claim 1 having a titer of infectious particles produced at the end of step d) higher than $1 \times 10^6$ TU/mL, or $2 > 10^6$ TU/mL, and/or a physical titer of particles produced at the end of step d) higher than $1.5 \times 10^5$ ng p24/mL.

4. The method according to claim 1, wherein the concentration of step d) comprises centrifugating and/or purifying the harvested stable lentiviral particles obtained in c).

5. The method according to claim 1, wherein the preparation of stable concentrated lentiviral particles produced in step d) have a high infectious titer higher than $2 \times 10^6$ TU/mL after freezing and thawing of the preparation.

* * * * *

SEQUENCE LISTING

```
<160> NUMBER OF SEQ ID NOS: 41

<210> SEQ ID NO 1
<211> LENGTH: 1617
<212> TYPE: DNA
<213> ORGANISM: Artificial Sequence
<220> FEATURE:
<223> OTHER INFORMATION: Synthetic cDNA of human HERV-W

<400> SEQUENCE: 1
atggccctcc cttatcatat ttttctcttt actgttcttt taccctcttt cactctcact      60
gcaccccctc catgccgctg tatgaccagt agctcccctt accaagagtt tctatggaga     120
atgcagcgtc ccggaaatat tgatgcccca tcgtatagga gtctttctaa gggaaccccc     180
accttcactg cccacaccca tatgccccgc aactgctatc actctgccac tctttgcatg     240
catgcaaata ctcattattg gacaggaaaa atgattaatc ctagttgtcc tggaggactt     300
ggagtcactg tctgttggac ttacttcacc caaactggta tgtctgatgg gggtggagtt     360
caagatcagg caagagaaaa acatgtaaaa gaagtaatct cccaactcac ccgggtacat     420
ggcacctcta gcccctacaa aggactagat ctctcaaaac tacatgaaac cctccgtacc     480
catactcgcc tggtaagcct atttaatacc accctcactg ggctccatga ggtctcggcc     540
caaaacccta ctaactgttg gatatgcctc cccctgaact tcaggccata tgtttcaatc     600
cctgtacctg aacaatggaa caacttcagc acagaaataa acaccacttc cgttttagta     660
ggacctcttg tttccaatct ggaaataacc cataccctcaa acctcacctg tgtaaaattt     720
agcaatacta catacacaac caactcccaa tgcatcaggt gggtaactcc tcccacacaa     780
atagtctgcc taccctcagg aatattttt gtctgtggta cctcagccta tcgttgtttg     840
aatggctctt cagaatctat gtgcttcctc tcattcttag tgcccctat gaccatctac     900 actgaacaag atttatacag ttatgtcata tctaagcccc gcaacaaaag agtacccatt     960
cttccttttg ttataggagc aggagtgcta ggtgcactag tactggcat tggcggtatc    1020 acaacctcta ctcagttcta ctacaaacta tctcaagaac taaatgggga catggaacgg    1080
gtcgccgact ccctggtcac cttgcaagat caacttaact ccctagcagc agtagtcctt    1140
```

-continued

```
caaaatcgaa gagctttaga cttgctaacc gctgaaagag ggggaacctg tttatttta      1200 ggggaagaat gctgttatta tgttaatcaa tccggaatcg tcactgagaa agttaaagaa      1260
attcgagatc gaatacaacg tagagcagag gagcttcgaa acactggacc ctggggcctc      1320
ctcagccaat ggatgccctg gattctcccc ttcttaggac tctagcagc tataatattg       1380 ctactcctct ttggaccctg tatctttaac ctccttgtta actttgtctc ttccagaatc      1440
gaagctgtaa aactacaaat ggagcccaag atgcagtcca agactaagat ctaccgcaga      1500
cccctggacc ggcctgctag cccacgatct gatgttaatg acatcaaagg caccccctcct    1560 gaggaaatct cagctgcaca acctctacta cgccccaatt cagcaggaag cagttag         1617
```

```
<210> SEQ ID NO 2
<211> LENGTH: 1617
<212> TYPE: DNA
<213> ORGANISM: Artificial Sequence
<220> FEATURE:
<223> OTHER INFORMATION: Synthetic cDNA of human HERV-FRD

<400> SEQUENCE: 2
```

```
atgggcctgc tcctgctggt tctcattctc acgccttcac tagcagccta ccgccatcct      60
gatttcccgt tattggaaaa agctcagcaa ctgctccaaa gtacaggatc cccttactcc      120
accaattgct ggttatgtac tagctcttcc actgaaacac cagggacagc ttatccagcc      180
tcgcccagag aatggacaag catagaggcg aattacata tttcctatcg atgggaccct      240
aatctgaaag gactgatgag gcctgcaaat agtcttcttt caacagtaaa gcaagatttc      300
cctgatatcc gccagaaacc tcccattttc ggacccatct ttactaatat caacctaatg      360
ggaatagccc ctatttgtgt tatggccaaa aggaaaaatg aacaaatgt aggcactctt      420 ccaagtacag tctgtaatgt tactttcact gtagattcta accaacgac ttaccaaaca       480 tacacccaca accaattccg ccatcaacca agattcccca aacctccaaa tattactttt      540
cctcagggaa ctttgctaga taaatccagc cggttttgcc agggacgccc aagctcatgc      600
agtactcgaa acttctggtt ccggcctgct gattataacc aatgtctgca aatttccaac      660
ctcagctcta cagcggaatg ggttctattg gaccaaactc gaaattctct tttttgggaa      720
aataaaacca agggagctaa ccagagccaa acaccctgcg tccaagtctt agcaggcatg      780
actatagcca ccagctacct gggcatatca gcagtctcag aatttttgg aacctccctc      840 acccccttat ttcatttcca tatctctaca tgccttaaaa ctcaaggagc cttttatatt      900
tgtggccagt cgattcacca atgcctcccc agtaactgga ctggaacttg taccataggc      960
tatgtaaccc cagacatctt catagcccct ggcaatctct ctcttccaat accaatctat     1020
gggaattccc cgttgcccag ggtgaggagg gcaatccatt tcattcccct ctctcgcggga    1080 ctcggcattc tagctggtac gggaaccgga attgctggaa tcacaaaagc ttccctcacc     1140
tatagccagc tctcaaagga aatagccaac aacattgaca ccatggctaa agccttaacg    1200
accatgcaag aacaaatcga ctctttagca gccgtagtcc ttcaaaatcg tcgaggacta    1260
gacatgttaa cggcagcaca gggaggaatt tgtttggcct tagatgaaaa atgttgcttt     1320
tgggtaaatc aatcaggaaa agtacaagac aacatcagac aactcctaaa tcaagcctcc    1380
agtttacggg aacgagccac tcagggttgg ttaaattggg aaggaacttg gaaatggttc    1440
tcttgggttc ttcccttac aggcccactt gttagtctcc tactttgct ccttttggt       1500 ccatgtctcc taaatctaat aacccaattt gtctcctctc gccttcaggc cataaagctc    1560
cagacgaatc tcagtgcagg acgccatcct cgcaatattc aagagtcacc cttctaa        1617
```

<210> SEQ ID NO 3
<211> LENGTH: 7150
<212> TYPE: DNA
<213> ORGANISM: Artificial Sequence
<220> FEATURE:
<223> OTHER INFORMATION: Synthetic pcDNA3.1 SYNCYTIN-1

<400> SEQUENCE: 3

| | | | | | |
|---|---|---|---|---|---|
| tcgagtctag | agggcccgtt | taaacccgct | gatcagcctc | gactgtgcct | tctagttgcc | 60 |
| agccatctgt | tgtttgcccc | tcccccgtgc | cttccttgac | cctggaaggt | gccactccca | 120 |
| ctgtcctttc | ctaataaaat | gaggaaattg | catcgcattg | tctgagtagg | tgtcattcta | 180 |
| ttctgggggg | tggggtgggg | caggacagca | agggggagga | ttgggaagac | aatagcaggc | 240 |
| atgctgggga | tgcggtgggc | tctatggctt | ctgaggcgga | agaaccagc | tggggctcta | 300 |
| ggggtatcc | ccacgcgccc | tgtagcggcg | cattaagcgc | ggcgggtgtg | gtggttacgc | 360 |
| gcagcgtgac | cgctacactt | gccagcgccc | tagcgcccgc | tcctttcgct | ttcttccctt | 420 |
| cctttctcgc | cacgttcgcc | ggctttcccc | gtcaagctct | aaatcggggc | atccctttag | 480 |
| ggttccgatt | tagtgcttta | cggcacctcg | accccaaaaa | acttgattag | ggtgatggtt | 540 |
| cacgtagtgg | gccatcgccc | tgatagacgg | ttttcgccc | tttgacgttg | gagtccacgt | 600 |
| tctttaatag | tggactcttg | ttccaaactg | gaacaacact | caaccctatc | tcggtctatt | 660 |
| cttttgattt | ataagggatt | ttggggattt | cggcctattg | gttaaaaaat | gagctgattt | 720 |
| aacaaaaatt | taacgcgaat | taattctgtg | gaatgtgtgt | cagttagggt | gtggaaagtc | 780 |
| cccaggctcc | ccaggcaggc | agaagtatgc | aaagcatgca | tctcaattag | tcagcaacca | 840 |
| ggtgtggaaa | gtccccaggc | tccccagcag | gcagaagtat | gcaaagcatg | catctcaatt | 900 |
| agtcagcaac | catagtcccg | cccctaactc | cgcccatccc | gcccctaact | ccgcccagtt | 960 |
| ccgcccattc | tccgccccat | ggctgactaa | ttttttttat | ttatgcagag | gccgaggccg | 1020 |
| cctctgcctc | tgagctattc | cagaagtagt | gaggaggctt | ttttggaggc | ctaggctttt | 1080 |
| gcaaaaagct | cccgggagct | tgtatatcca | ttttcggatc | tgatcagcac | gtgatgaaaa | 1140 |
| agcctgaact | caccgcgacg | tctgtcgaga | agtttctgat | cgaaaagttc | gacagcgtct | 1200 |
| ccgacctgat | gcagctctcg | gagggcgaag | aatctcgtgc | tttcagcttc | gatgtaggag | 1260 |
| ggcgtggata | tgtcctgcgg | gtaaatagct | gcgccgatgg | tttctacaaa | gatcgttatg | 1320 |
| tttatcggca | ctttgcatcg | gccgcgctcc | cgattccgga | agtgcttgac | attggggaat | 1380 |
| tcagcgagag | cctgacctat | tgcatctccc | gccgtgcaca | gggtgtcacg | ttgcaagacc | 1440 |
| tgcctgaaac | cgaactgccc | gctgttctgc | agccggtcgc | ggaggccatg | gatgcgatcg | 1500 |
| ctgcggccga | tcttagccag | acgagcgggt | tcggcccatt | cggaccgcaa | ggaatcggtc | 1560 |
| aatacactac | atggcgtgat | ttcatatgcg | cgattgctga | tccccatgtg | tatcactggc | 1620 |
| aaactgtgat | ggacgacacc | gtcagtgcgt | ccgtcgcgca | ggctctcgat | gagctgatgc | 1680 |
| tttgggccga | ggactgcccc | gaagtccggc | acctcgtgca | cgcggatttc | ggctccaaca | 1740 |
| atgtcctgac | ggacaatggc | cgcataacag | cggtcattga | ctggagcgag | gcgatgttcg | 1800 |
| gggattccca | atacgaggtc | gccaacatct | tcttctggag | gccgtggttg | gcttgtatgg | 1860 |
| agcagcagac | gcgctacttc | gagcggaggc | atccggagct | tgcaggatcg | ccgcggctcc | 1920 |
| gggcgtatat | gctccgcatt | ggtcttgacc | aactctatca | gagcttggtt | gacgcaattt | 1980 |
| tcgatgatgc | agcttgggcg | cagggtcgat | gcgacgcaat | cgtccgatcc | ggagccggga | 2040 |

-continued

```
ctgtcgggcg tacacaaatc gcccgcagaa gcgcggccgt ctggaccgat ggctgtgtag    2100
aagtactcgc cgatagtgga aaccgacgcc ccagcactcg tccgagggca aaggaatagc    2160
acgtgctacg agatttcgat tccaccgccg ccttctatga aaggttgggc ttcggaatcg    2220
ttttccggga cgccggctgg atgatcctcc agcgcgggga tctcatgctg gagttcttcg    2280 cccacccaa cttgtttatt gcagcttata atggttacaa ataaagcaat agcatcacaa    2340
atttcacaaa taaagcattt ttttcactgc attctagttg tggtttgtcc aaactcatca    2400
atgtatctta tcatgtctgt ataccgtcga cctctagcta gagcttggcg taatcatggt    2460
catagctgtt tcctgtgtga aattgttatc cgctcacaat tccacacaac atacgagccg    2520
gaagcataaa gtgtaaagcc tggggtgcct aatgagtgag ctaactcaca ttaattgcgt    2580
tgcgctcact gcccgctttc cagtcgggaa acctgtcgtg ccagctgcat taatgaatcg    2640
gccaacgcgc ggggagaggc ggtttgcgta ttgggcgctc ttccgcttcc tcgctcactg    2700
actcgctgcg ctcggtcgtt cggctgcggc gagcggtatc agctcactca aaggcggtaa    2760
tacggttatc cacagaatca ggggataacg caggaaagaa catgtgagca aaaggccagc    2820
aaaaggccag gaaccgtaaa aaggccgcgt tgctggcgtt tttccatagg ctccgccccc    2880
ctgacgagca tcacaaaaat cgacgctcaa gtcagaggtg gcgaaacccg acaggactat    2940
aaagatacca ggcgtttccc cctggaagct ccctcgtgcg ctctcctgtt ccgaccctgc    3000
cgcttaccgg atacctgtcc gcctttctcc cttcgggaag cgtggcgctt tctcaatgct    3060
cacgctgtag gtatctcagt tcggtgtagg tcgttcgctc caagctgggc tgtgtgcacg    3120 aacccccgt tcagcccgac cgctgcgcct tatccggtaa ctatcgtctt gagtccaacc    3180
cggtaagaca cgacttatcg ccactggcag cagccactgg taacaggatt agcagagcga    3240
ggtatgtagg cggtgctaca gagttcttga agtggtggcc taactacggc tacactagaa    3300
ggacagtatt tggtatctgc gctctgctga agccagttac cttcggaaaa agagttggta    3360
gctcttgatc cggcaaacaa accaccgctg gtagcggtgg ttttttttgtt tgcaagcagc    3420 agattacgcg cagaaaaaaa ggatctcaag aagatccttt gatcttttct acggggtctg    3480
acgctcagtg gaacgaaaac tcacgttaag ggattttggt catgagatta tcaaaaagga    3540
tcttcaccta gatcctttta aattaaaaat gaagttttaa atcaatctaa agtatatatg    3600
agtaaacttg gtctgacagt taccaatgct taatcagtga ggcacctatc tcagcgatct    3660
gtctatttcg ttcatccata gttgcctgac tccccgtcgt gtagataact acgatacggg    3720
agggcttacc atctggcccc agtgctgcaa tgataccgcg agacccacgc tcaccggctc    3780
cagatttatc agcaataaac cagccagccg gaagggccga gcgcagaagt ggtcctgcaa    3840
ctttatccgc ctccatccag tctattaatt gttgccggga agctagagta agtagttcgc    3900
cagttaatag tttgcgcaac gttgttgcca ttgctacagg catcgtggtg tcacgctcgt    3960
cgtttggtat ggcttcattc agctccggtt cccaacgatc aaggcgagtt acatgatccc    4020
ccatgttgtg caaaaaagcg gttagctcct tcggtcctcc gatcgttgtc agaagtaagt    4080
tggccgcagt gttatcactc atggttatgg cagcactgca taattctctt actgtcatgc    4140
catccgtaag atgcttttct gtgactggtg agtactcaac caagtcattc tgagaatagt    4200
gtatgcggcg accgagttgc tcttgcccgg cgtcaatacg ggataatacc gcgccacata    4260
gcagaacttt aaaagtgctc atcattggaa aacgttcttc ggggcgaaaa ctctcaagga    4320
tcttaccgct gttgagatcc agttcgatgt aacccactcg tgcacccaac tgatcttcag    4380
catcttttac tttcaccagc gtttctgggt gagcaaaaac aggaaggcaa aatgccgcaa    4440
```

```
aaaagggaat aagggcgaca cggaaatgtt gaatactcat actcttcctt tttcaatatt    4500
attgaagcat ttatcagggt tattgtctca tgagcggata catatttgaa tgtatttaga    4560
aaaataaaca aatagggtt ccgcgcacat ttccccgaaa agtgccacct gacgtcgacg     4620
gatcgggaga tctcccgatc ccctatggtc gactctcagt acaatctgct ctgatgccgc    4680
atagttaagc cagtatctgc tccctgcttg tgtgttggag gtcgctgagt agtgcgcgag    4740
caaaatttaa gctacaacaa ggcaaggctt gaccgacaat tgcatgaaga atctgcttag    4800
ggttaggcgt tttgcgctgc ttcgcgatgt acgggccaga tatacgcgtt gacattgatt    4860
attgactagt tattaatagt aatcaattac ggggtcatta gttcatagcc catatatgga    4920
gttccgcgtt acataactta cggtaaatgg cccgcctggc tgaccgccca acgaccccg     4980 cccattgacg tcaataatga cgtatgttcc catagtaacg ccaataggga ctttccattg    5040
acgtcaatgg gtggactatt tacggtaaac tgcccacttg gcagtacatc aagtgtatca    5100
tatgccaagt acgcccccta ttgacgtcaa tgacggtaaa tggcccgcct ggcattatgc    5160
ccagtacatg accttatggg actttcctac ttggcagtac atctacgtat tagtcatcgc    5220
tattaccatg gtgatgcggt tttggcagta catcaatggg cgtggatagc ggtttgactc    5280
acggggattt ccaagtctcc accccattga cgtcaatggg agtttgtttt ggcaccaaaa    5340
tcaacgggac tttccaaaat gtcgtaacaa ctccgcccca ttgacgcaaa tgggcggtag    5400
gcgtgtacgg tgggaggtct atataagcag agctctctgg ctaactagag aacccactgc    5460
ttactggctt atcgaaatta atacgactca ctatagggag acccaagctg gctagcgttt    5520
aaacttaagc ttatggccct cccttatcat attttctct ttactgttct tttaccctct     5580
ttcactctca ctgcacccc tccatgccgc tgtatgacca gtagctcccc ttaccaagag     5640
tttctatgga gaatgcagcg tcccggaaat attgatgccc catcgtatag gagtctttct    5700
aagggaaccc ccaccttcac tgcccacacc catatgcccc gcaactgcta tcactctgcc    5760
actctttgca tgcatgcaaa tactcattat tggacaggaa aaatgattaa tcctagttgt    5820
cctggaggac ttggagtcac tgtctgttgg acttacttca cccaaactgg tatgtctgat    5880
gggggtggag ttcaagatca ggcaagagaa aaacatgtaa aagaagtaat ctcccaactc    5940
acccgggtac atggcacctc tagccctac aaaggactag atctctcaaa actacatgaa     6000
accctccgta cccatactcg cctggtaagc ctatttaata ccaccctcac tgggctccat    6060
gaggtctcgg cccaaaaccc tactaactgt tggatatgcc tccccctgaa cttcaggcca    6120
tatgtttcaa tccctgtacc tgaacaatgg aacaacttca gcacagaaat aaacaccact    6180
tccgttttag taggacctct tgtttccaat ctggaaataa cccataccct aaacctcacc    6240
tgtgtaaaat ttagcaatac tacatacaca accaactccc aatgcatcag gtgggtaact    6300
cctcccacac aaatagtctg cctaccctca ggaatatttt ttgtctgtgg tacctcagcc    6360
tatcgttgtt tgaatggctc ttcagaatct atgtgcttcc tctcattctt agtgcccct     6420 atgaccatct acactgaaca agatttatac agttatgtca tatctaagcc ccgcaacaaa    6480
agagtaccca ttcttccttt tgttatagga gcaggagtgc taggtgcact aggtactggc    6540
attggcggta tcacaacctc tactcagttc tactacaaac tatctcaaga actaaatggg    6600
gacatggaac gggtcgccga ctccctggtc accttgcaag atcaacttaa ctccctagca    6660
gcagtagtcc ttcaaaatcg aagagcttta gacttgctaa ccgctgaaag aggggaacc    6720 tgtttatttt taggggaaga atgctgttat tatgttaatc aatccggaat cgtcactgag    6780
```

-continued

```
aaagttaaag aaattcgaga tcgaatacaa cgtagagcag aggagcttcg aaacactgga    6840
ccctggggcc tcctcagcca atggatgccc tggattctcc ccttcttagg acctctagca    6900
gctataatat tgctactcct ctttggaccc tgtatcttta acctccttgt taactttgtc    6960
tcttccagaa tcgaagctgt aaaactacaa atggagccca agatgcagtc caagactaag    7020
atctaccgca gaccccctgga ccggcctgct agcccacgat ctgatgttaa tgacatcaaa    7080
ggcacccctc ctgaggaaat ctcagctgca aacctctac tacgcccaa ttcagcagga     7140 agcagttagc                                                           7150
```

<210> SEQ ID NO 4
<211> LENGTH: 7134
<212> TYPE: DNA
<213> ORGANISM: Artificial Sequence
<220> FEATURE:
<223> OTHER INFORMATION: Synthetic pcDNA3.1 SYNCYTIN-2

<400> SEQUENCE: 4

```
cactcatggt tatggcagca ctgcataatt ctcttactgt catgccatcc gtaagatgct      60
tttctgtgac tggtgagtac tcaaccaagt cattctgaga atagtgtatg cggcgaccga    120
gttgctcttg cccggcgtca atacgggata taccgcgcc acatagcaga actttaaaag    180
tgctcatcat tggaaaacgt tcttcggggc gaaaactctc aaggatctta ccgctgttga    240
gatccagttc gatgtaaccc actcgtgcac ccaactgatc ttcagcatct tttactttca    300
ccagcgtttc tgggtgagca aaaacaggaa ggcaaaatgc cgcaaaaaag gaataagggg    360
cgacacggaa atgttgaata ctcatactct ccttttttca atattattga agcatttatc    420
agggttattg tctcatgagc ggatacatat ttgaatgtat ttagaaaaat aaacaaatag    480
gggttccgcg cacatttccc cgaaaagtgc cacctgacgt cgacggatcg ggagatctcc    540
cgatccccta tggtcgactc tcagtacaat ctgctctgat gccgcatagt taagccagta    600 tctgctcccct gcttgtgtgt tggaggtcgc tgagtagtgc gcgagcaaaa tttaagctac    660
aacaaggcaa ggcttgaccg acaattgcat gaagaatctg cttagggtta ggcgttttgc    720
gctgcttcgc gatgtacggg ccagatatac gcgttgacat tgattattga ctagttatta    780
atagtaatca attacggggt cattagttca tagcccatat atggagttcc gcgttacata    840
acttacggta atggcccgcc tggctgaccg cccaacgac ccccgcccat tgacgtcaat     900
aatgacgtat gttcccatag taacgccaat agggactttc cattgacgtc aatgggtgga    960
ctatttacgg taaactgccc acttggcagt acatcaagtg tatcatatgc caagtacgcc   1020
ccctattgac gtcaatgacg gtaaatggcc cgcctggcat tatgcccagt acatgacctt   1080
atgggacttt cctacttggc agtacatcta cgtattagtc atcgctatta ccatggtgat   1140
gcggttttgg cagtacatca atgggcgtgg atagcggttt gactcacggg gatttccaag   1200 tctccaccc attgacgtca atgggagttt gttttggcac caaaatcaac gggactttcc   1260
aaaatgtcgt aacaactccg ccccattgac gcaaatgggc ggtaggcgtg tacggtggga   1320
ggtctatata agcagagctc tctggctaac tagagaaccc actgcttact ggcttatcga   1380
aattaatacg actcactata gggagaccca agctggctag catgggcctg ctcctgctgg   1440
ttctcattct cacgccttca ctagcagcct accgccatcc tgatttcccg ttattggaaa   1500
aagctcagca actgctccaa agtacaggat ccccttactc caccaattgc tggttatgta   1560
ctagctcttc cactgaaaca ccagggacag cttatccagc ctcgcccaga gaatggacaa   1620
gcatagaggc ggaattacat atttcctatc gatgggaccc taatctgaaa ggactgatga   1680
```

```
ggcctgcaaa tagtcttctt tcaacagtaa agcaagattt ccctgatatc cgccagaaac    1740
ctcccatttt cggacccatc tttactaata tcaacctaat gggaatagcc cctatttgtg    1800
ttatggccaa aaggaaaaat ggaacaaatg taggcactct tccaagtaca gtctgtaatg    1860
ttactttcac tgtagattct aaccaacaga cttaccaaac atacacccac aaccaattcc    1920
gccatcaacc aagattcccc aaacctccaa atattacttt tcctcaggga actttgctag    1980
ataaatccag ccggttttgc cagggacgcc aagctcatg cagtactcga aacttctggt    2040
tccggcctgc tgattataac caatgtctgc aaatttccaa cctcagctct acagcggaat    2100
gggttctatt ggaccaaact cgaaattctc ttttttggga aaataaaacc aagggagcta    2160
accagagcca acaccctgc gtccaagtct tagcaggcat gactatagcc accagctacc    2220
tgggcatatc agcagtctca gaattttttg gaacctccct cacccccta tttcatttcc    2280 atatctctac atgccttaaa actcaaggag ccttttatat ttgtggccag tcgattcacc    2340
aatgcctccc cagtaactgg actgaacttg taccatagg ctatgtaacc ccagacatct    2400
tcatagcccc tggcaatctc tctcttccaa taccaatcta tgggaattcc ccgttgccca    2460
gggtgaggag ggcaatccat ttcattcccc ttctcgcggg actcggcatt ctagctggta    2520
cgggaaccgg aattgctgga atcacaaaag cttccctcac ctatagccag ctctcaaagg    2580
aaatagccaa caacattgac accatggcta aagccttaac gaccatgcaa gaacaaatcg    2640
actctttagc agccgtagtc cttcaaaatc gtcgaggact agacatgtta acggcagcac    2700
agggaggaat ttgtttggcc ttagatgaaa aatgttgctt ttgggtaaat caatcaggaa    2760
aagtacaaga caacatcaga caactcctaa atcaagcctc cagtttacgg gaacgagcca    2820 ctcaggttg gttaaattgg gaaggaactt ggaaatggtt ctcttgggtt cttcccctta    2880
caggcccact tgttagtctc ctactttgc tccttttgg tccatgtctc ctaaatctaa    2940
taacccaatt tgtctcctct cgccttcagg ccataaagct ccagacgaat ctcagtgcag    3000
gacgccatcc tcgcaatatt caagagtcac ccttctaact cgagtctaga gggcccgttt    3060
aaacccgctg atcagcctcg actgtgcctt ctagttgcca gccatctgtt gtttgcccct    3120
cccccgtgcc ttccttgacc ctggaaggtg ccactcccac tgtcctttcc taataaaatg    3180
aggaaattgc atcgcattgt ctgagtaggt gtcattctat tctggggggt ggggtggggc    3240
aggacagcaa gggggaggat tgggaagaca atagcaggca tgctgggat gcggtgggct    3300 ctatggcttc tgaggcggaa agaaccagct ggggctctag ggggtatccc cacgcgccct    3360
gtagcggcgc attaagcgcg gcgggtgtgg tggttacgcg cagcgtgacc gctacacttg    3420
ccagcgccct agcgcccgct cctttcgctt tcttcccttc ctttctcgcc acgttcgccg    3480
gctttccccg tcaagctcta aatcgggca tccctttagg gttccgattt agtgctttac    3540
ggcacctcga ccccaaaaaa cttgattagg gtgatggttc acgtagtggg ccatcgccct    3600
gatagacggt ttttcgccct ttgacgttgg agtccacgtt ctttaatagt ggactcttgt    3660
tccaaactgg aacaacactc aaccctatct cggtctattc ttttgattta agggattt    3720 tggggatttc ggcctattgg ttaaaaaatg agctgattta caaaaattt aacgcgaatt    3780 aattctgtgg aatgtgtgtc agttagggtg tggaaagtcc ccaggctccc caggcaggca    3840
gaagtatgca aagcatgcat ctcaattagt cagcaaccag gtgtggaaag tccccaggct    3900
ccccagcagg cagaagtatg caaagcatgc atctcaatta gtcagcaacc atagtcccgc    3960
ccctaactcc gcccatcccg cccctaactc cgcccagttc cgcccattct ccgccccatg    4020
```

-continued

```
gctgactaat tttttttatt tatgcagagg ccgaggccgc ctctgcctct gagctattcc    4080
agaagtagtg aggaggcttt tttggaggcc taggcttttg caaaaagctc ccgggagctt    4140
gtatatccat tttcggatct gatcagcacg tgatgaaaaa gcctgaactc accgcgacgt    4200
ctgtcgagaa gtttctgatc gaaaagttcg acagcgtctc cgacctgatg cagctctcgg    4260
agggcgaaga atctcgtgct ttcagcttcg atgtaggagg gcgtggatat gtcctgcggg    4320
taaatagctg cgccgatggt ttctacaaag atcgttatgt ttatcggcac tttgcatcgg    4380
ccgcgctccc gattccggaa gtgcttgaca ttggggaatt cagcgagagc ctgacctatt    4440
gcatctcccg ccgtgcacag ggtgtcacgt tgcaagacct gcctgaaacc gaactgcccg    4500
ctgttctgca gccggtcgcg gaggccatgg atgcgatcgc tgcggccgat cttagccaga    4560
cgagcgggtt cggcccattc ggaccgcaag gaatcggtca atacactaca tggcgtgatt    4620
tcatatgcgc gattgctgat ccccatgtgt atcactggca aactgtgatg gacgacaccg    4680
tcagtgcgtc cgtcgcgcag gctctcgatg agctgatgct ttgggccgag gactgccccg    4740
aagtccggca cctcgtgcac gcggatttcg gctccaacaa tgtcctgacg gacaatggcc    4800
gcataacagc ggtcattgac tggagcgagg cgatgttcgg ggattcccaa tacgaggtcg    4860
ccaacatctt cttctggagg ccgtggttgg cttgtatgga gcagcagacg cgctacttcg    4920
agcggaggca tccggagctt gcaggatcgc cgcggctccg ggcgtatatg ctccgcattg    4980
gtcttgacca actctatcag agcttggttg acggcaattt cgatgatgca gcttgggcgc    5040
agggtcgatg cgacgcaatc gtccgatccg gagccgggac tgtcgggcgt acacaaatcg    5100
cccgcagaag cgcggccgtc tggaccgatg gctgtgtaga agtactcgcc gatagtggaa    5160
accgacgccc cagcactcgt ccgagggcaa aggaatagca cgtgctacga gatttcgatt    5220
ccaccgccgc cttctatgaa aggttgggct tcggaatcgt tttccgggac gccggctgga    5280
tgatcctcca gcgcggggat ctcatgctgg agttcttcgc ccaccccaac ttgtttattg    5340
cagcttataa tggttacaaa taaagcaata gcatcacaaa tttcacaaat aaagcatttt    5400
tttcactgca ttctagttgt ggtttgtcca aactcatcaa tgtatcttat catgtctgta    5460
taccgtcgac ctctagctag agcttggcgt aatcatggtc atagctgttt cctgtgtgaa    5520
attgttatcc gctcacaatt ccacacaaca tacgagccgg aagcataaag tgtaaagcct    5580
ggggtgccta atgagtgagc taactcacat taattgcgtt gcgctcactg cccgctttcc    5640
agtcgggaaa cctgtcgtgc cagctgcatt aatgaatcgg ccaacgcgcg gggagaggcg    5700
gtttgcgtat tgggcgctct tccgcttcct cgctcactga ctcgctgcgc tcggtcgttc    5760
ggctgcggcg agcggtatca gctcactcaa aggcggtaat acggttatcc acagaatcag    5820
gggataacgc aggaaagaac atgtgagcaa aaggccagca aaaggccagg aaccgtaaaa    5880
aggccgcgtt gctggcgttt ttccataggc tccgcccccc tgacgagcat cacaaaaatc    5940
gacgctcaag tcagaggtgg cgaaacccga caggactata aagataccag gcgtttcccc    6000
ctggaagctc cctcgtgcgc tctcctgttc cgaccctgcc gcttaccgga tacctgtccg    6060
cctttctccc ttcgggaagc gtggcgcttt ctcaatgctc acgctgtagg tatctcagtt    6120
cggtgtaggt cgttcgctcc aagctgggct gtgtgcacga accccccgtt cagcccgacc    6180
gctgcgcctt atccggtaac tatcgtcttg agtccaaccc ggtaagacac gacttatcgc    6240
cactggcagc agccactggt aacaggatta gcagagcgag gtatgtaggc ggtgctacag    6300
agttcttgaa gtggtggcct aactacggct acactagaag gacagtattt ggtatctgcg    6360
ctctgctgaa gccagttacc ttcggaaaaa gagttggtag ctcttgatcc ggcaaacaaa    6420
```

```
ccaccgctgg tagcggtggt ttttttgttt gcaagcagca gattacgcgc agaaaaaaag    6480
gatctcaaga agatcctttg atcttttcta cggggtctga cgctcagtgg aacgaaaact    6540
cacgttaagg gattttggtc atgagattat caaaaaggat cttcacctag atccttttaa    6600
attaaaaatg aagttttaaa tcaatctaaa gtatatatga gtaaacttgg tctgacagtt    6660
accaatgctt aatcagtgag gcacctatct cagcgatctg tctatttcgt tcatccatag    6720
ttgcctgact ccccgtcgtg tagataacta cgatacggga gggcttacca tctggcccca    6780
gtgctgcaat gataccgcga gacccacgct caccggctcc agatttatca gcaataaacc    6840
agccagccgg aagggccgag cgcagaagtg gtcctgcaac tttatccgcc tccatccagt    6900
ctattaattg ttgccgggaa gctagagtaa gtagttcgcc agttaatagt ttgcgcaacg    6960
ttgttgccat tgctacaggc atcgtggtgt cacgctcgtc gtttggtatg gcttcattca    7020
gctccggttc ccaacgatca aggcgagtta catgatcccc catgttgtgc aaaaaagcgg    7080
ttagctcctt cggtcctccg atcgttgtca gaagtaagtt ggccgcagtg ttat          7134
```

```
<210> SEQ ID NO 5
<211> LENGTH: 26
<212> TYPE: PRT
<213> ORGANISM: Artificial Sequence
<220> FEATURE:
<223> OTHER INFORMATION: Synthetic LAH4

<400> SEQUENCE: 5

Lys Lys Ala Leu Leu Ala Leu Ala Leu His His Leu Ala His Leu Ala
1               5                   10                  15

Leu His Leu Ala Leu Ala Leu Lys Lys Ala
            20                  25

<210> SEQ ID NO 6
<211> LENGTH: 26
<212> TYPE: PRT
<213> ORGANISM: Artificial Sequence
<220> FEATURE:
<223> OTHER INFORMATION: Synthetic LAH4-L1

<400> SEQUENCE: 6

Lys Lys Ala Leu Leu Ala His Ala Leu His Leu Leu Ala Leu Leu Ala
1               5                   10                  15

Leu His Leu Ala His Ala Leu Lys Lys Ala
            20                  25

<210> SEQ ID NO 7
<211> LENGTH: 24
<212> TYPE: PRT
<213> ORGANISM: Artificial Sequence
<220> FEATURE:
<223> OTHER INFORMATION: Synthetic LAH4-L1-dKC

<400> SEQUENCE: 7

Lys Lys Ala Leu Leu Ala His Ala Leu His Leu Leu Ala Leu Leu Ala
1               5                   10                  15

Leu His Leu Ala His Ala Leu Ala
            20

<210> SEQ ID NO 8
<211> LENGTH: 26
<212> TYPE: PRT
<213> ORGANISM: Artificial Sequence
<220> FEATURE:
```

```
<223> OTHER INFORMATION: Synthetic LAH4-L1-R

<400> SEQUENCE: 8

Arg Arg Ala Leu Leu Ala His Ala Leu His Leu Leu Ala Leu Leu Ala
1               5                   10                  15

Leu His Leu Ala His Ala Leu Arg Arg Ala
            20                  25

<210> SEQ ID NO 9
<211> LENGTH: 26
<212> TYPE: PRT
<213> ORGANISM: Artificial Sequence
<220> FEATURE:
<223> OTHER INFORMATION: Synthetic LAH4-L0

<400> SEQUENCE: 9

Lys Lys Ala Leu Leu Ala His Ala Leu Ala His Leu Ala Leu Leu Ala
1               5                   10                  15

Leu His Leu Ala Leu His Leu Lys Lys Ala
            20                  25

<210> SEQ ID NO 10
<211> LENGTH: 26
<212> TYPE: PRT
<213> ORGANISM: Artificial Sequence
<220> FEATURE:
<223> OTHER INFORMATION: Synthetic LAH4-L2

<400> SEQUENCE: 10

Lys Lys Ala Leu Leu Ala Leu Ala Leu His His Leu Ala Leu Leu Ala
1               5                   10                  15

Leu His Leu Ala His Ala Leu Lys Lys Ala
            20                  25

<210> SEQ ID NO 11
<211> LENGTH: 26
<212> TYPE: PRT
<213> ORGANISM: Artificial Sequence
<220> FEATURE:
<223> OTHER INFORMATION: Synthetic LAH4-L3

<400> SEQUENCE: 11

Lys Lys Ala Leu Leu Ala Leu Ala Leu His His Leu Ala Leu Leu Ala
1               5                   10                  15

His His Leu Ala Leu Ala Leu Lys Lys Ala
            20                  25

<210> SEQ ID NO 12
<211> LENGTH: 26
<212> TYPE: PRT
<213> ORGANISM: Artificial Sequence
<220> FEATURE:
<223> OTHER INFORMATION: Synthetic LAH4-L4iso

<400> SEQUENCE: 12

Lys Lys Ala Leu Leu His Leu Ala Leu Leu His Ala Ala Leu Leu Ala
1               5                   10                  15

His His Leu Ala Leu Ala Leu Lys Lys Ala
            20                  25

<210> SEQ ID NO 13
<211> LENGTH: 26
<212> TYPE: PRT
<213> ORGANISM: Artificial Sequence
```

```
<220> FEATURE:
<223> OTHER INFORMATION: Synthetic LAH4-L5

<400> SEQUENCE: 13

Lys Lys Ala Leu Leu His Leu Ala Leu Leu His Ala Ala Leu Leu Ala
1               5                   10                  15

His Leu Ala Ala Leu His Leu Lys Lys Ala
            20                  25

<210> SEQ ID NO 14
<211> LENGTH: 26
<212> TYPE: PRT
<213> ORGANISM: Artificial Sequence
<220> FEATURE:
<223> OTHER INFORMATION: Synthetic LAH4-L6iso

<400> SEQUENCE: 14

Lys Lys Ala Leu Leu His Leu Ala Leu Leu Leu Ala Ala Leu His Ala
1               5                   10                  15

His Leu Ala Ala Leu His Leu Lys Lys Ala
            20                  25

<210> SEQ ID NO 15
<211> LENGTH: 26
<212> TYPE: PRT
<213> ORGANISM: Artificial Sequence
<220> FEATURE:
<223> OTHER INFORMATION: Synthetic LAH4-A1

<400> SEQUENCE: 15

Lys Lys Ala Leu Leu Ala His Ala Leu His Leu Leu Ala Ala Leu Ala
1               5                   10                  15

Leu His Leu Ala His Leu Leu Lys Lys Ala
            20                  25

<210> SEQ ID NO 16
<211> LENGTH: 26
<212> TYPE: PRT
<213> ORGANISM: Artificial Sequence
<220> FEATURE:
<223> OTHER INFORMATION: Synthetic LAH4-A2

<400> SEQUENCE: 16

Lys Lys Ala Leu Leu Leu Ala Ala Leu His His Leu Ala Ala Leu Ala
1               5                   10                  15

Leu His Leu Ala His Leu Leu Lys Lys Ala
            20                  25

<210> SEQ ID NO 17
<211> LENGTH: 26
<212> TYPE: PRT
<213> ORGANISM: Artificial Sequence
<220> FEATURE:
<223> OTHER INFORMATION: Synthetic LAH4-A3

<400> SEQUENCE: 17

Lys Lys Ala Leu Leu Leu Ala Ala Leu His His Leu Leu Ala Leu Ala
1               5                   10                  15

His His Leu Ala Ala Leu Leu Lys Lys Ala
            20                  25

<210> SEQ ID NO 18
<211> LENGTH: 26
<212> TYPE: PRT
```

```
<213> ORGANISM: Artificial Sequence
<220> FEATURE:
<223> OTHER INFORMATION: Synthetic vectofusin-1

<400> SEQUENCE: 18

Lys Lys Ala Leu Leu His Ala Ala Leu Ala His Leu Leu Ala Leu Ala
1               5                   10                  15

His His Leu Leu Ala Leu Leu Lys Lys Ala
            20                  25

<210> SEQ ID NO 19
<211> LENGTH: 26
<212> TYPE: PRT
<213> ORGANISM: Artificial Sequence
<220> FEATURE:
<223> OTHER INFORMATION: Synthetic LAH4-A5

<400> SEQUENCE: 19

Lys Lys Ala Leu Leu His Ala Leu Leu Ala His Leu Ala Ala Leu Leu
1               5                   10                  15

His Ala Leu Leu Ala His Leu Lys Lys Ala
            20                  25

<210> SEQ ID NO 20
<211> LENGTH: 26
<212> TYPE: PRT
<213> ORGANISM: Artificial Sequence
<220> FEATURE:
<223> OTHER INFORMATION: Synthetic LAH4-A6iso

<400> SEQUENCE: 20

Lys Lys Ala Leu Leu His Ala Leu Leu Ala Ala Leu Leu Ala His Leu
1               5                   10                  15

His Ala Leu Leu Ala His Leu Lys Lys Ala
            20                  25

<210> SEQ ID NO 21
<211> LENGTH: 25
<212> TYPE: PRT
<213> ORGANISM: Artificial Sequence
<220> FEATURE:
<223> OTHER INFORMATION: Synthetic LAH4-A4-K1N

<400> SEQUENCE: 21

Lys Ala Leu Leu His Ala Ala Leu Ala His Leu Leu Ala Leu Ala His
1               5                   10                  15

His Leu Leu Ala Leu Leu Lys Lys Ala
            20                  25

<210> SEQ ID NO 22
<211> LENGTH: 26
<212> TYPE: PRT
<213> ORGANISM: Artificial Sequence
<220> FEATURE:
<223> OTHER INFORMATION: Synthetic LAH4-A4-K3N

<400> SEQUENCE: 22

Lys Lys Lys Leu Leu His Ala Ala Leu Ala His Leu Leu Ala Leu Ala
1               5                   10                  15

His His Leu Leu Ala Leu Leu Lys Lys Ala
            20                  25

<210> SEQ ID NO 23
<211> LENGTH: 24
```

```
<212> TYPE: PRT
<213> ORGANISM: Artificial Sequence
<220> FEATURE:
<223> OTHER INFORMATION: Synthetic LAH4-A4-dKC

<400> SEQUENCE: 23

Lys Lys Ala Leu Leu His Ala Ala Leu Ala His Leu Leu Ala Leu Ala
1               5                   10                  15

His His Leu Leu Ala Leu Leu Ala
            20

<210> SEQ ID NO 24
<211> LENGTH: 24
<212> TYPE: PRT
<213> ORGANISM: Artificial Sequence
<220> FEATURE:
<223> OTHER INFORMATION: Synthetic LAH4-A4-dlaa

<400> SEQUENCE: 24

Lys Lys Ala Leu Leu His Ala Ala Leu Ala His Leu Leu Ala Leu Ala
1               5                   10                  15

His His Leu Leu Ala Leu Leu Lys
            20

<210> SEQ ID NO 25
<211> LENGTH: 23
<212> TYPE: PRT
<213> ORGANISM: Artificial Sequence
<220> FEATURE:
<223> OTHER INFORMATION: Synthetic LAH4-A4-d2aa

<400> SEQUENCE: 25

Lys Lys Leu Leu His Ala Ala Leu Ala His Leu Leu Ala Leu Ala His
1               5                   10                  15

His Leu Leu Ala Leu Leu Lys
            20

<210> SEQ ID NO 26
<211> LENGTH: 23
<212> TYPE: PRT
<213> ORGANISM: Artificial Sequence
<220> FEATURE:
<223> OTHER INFORMATION: Synthetic LAH4-A4-d2Caa

<400> SEQUENCE: 26

Lys Lys Ala Leu Leu His Ala Ala Leu Ala His Leu Leu Ala Leu Ala
1               5                   10                  15

His His Leu Leu Ala Leu Lys
            20

<210> SEQ ID NO 27
<211> LENGTH: 22
<212> TYPE: PRT
<213> ORGANISM: Artificial Sequence
<220> FEATURE:
<223> OTHER INFORMATION: Synthetic LAH4-A4-d3aa

<400> SEQUENCE: 27

Lys Lys Leu His Ala Ala Leu Ala His Leu Leu Ala Leu Ala His His
1               5                   10                  15

Leu Leu Ala Leu Leu Lys
            20

<210> SEQ ID NO 28
```

```
<211> LENGTH: 20
<212> TYPE: PRT
<213> ORGANISM: Artificial Sequence
<220> FEATURE:
<223> OTHER INFORMATION: Synthetic LAH4-A4-d5aa

<400> SEQUENCE: 28

Lys Lys Leu His Ala Ala Leu Ala His Leu Leu Ala Leu Ala His His
1               5                   10                  15

Leu Leu Ala Lys
            20

<210> SEQ ID NO 29
<211> LENGTH: 26
<212> TYPE: PRT
<213> ORGANISM: Artificial Sequence
<220> FEATURE:
<223> OTHER INFORMATION: Synthetic LAH2-A6

<400> SEQUENCE: 29

Lys Lys Ala Leu Leu His Ala Ala Leu Ala His Leu Leu Ala Leu Ala
1               5                   10                  15

Ala Ala Leu Leu Ala Leu Leu Lys Lys Ala
            20                  25

<210> SEQ ID NO 30
<211> LENGTH: 26
<212> TYPE: PRT
<213> ORGANISM: Artificial Sequence
<220> FEATURE:
<223> OTHER INFORMATION: Synthetic K2-L10A12-K2

<400> SEQUENCE: 30

Lys Lys Ala Leu Leu Ala Ala Ala Leu Ala Ala Leu Leu Ala Leu Ala
1               5                   10                  15

Ala Ala Leu Leu Ala Leu Leu Lys Lys Ala
            20                  25

<210> SEQ ID NO 31
<211> LENGTH: 26
<212> TYPE: PRT
<213> ORGANISM: Artificial Sequence
<220> FEATURE:
<223> OTHER INFORMATION: Synthetic LAH4-A4-Leu

<400> SEQUENCE: 31

Lys Lys Leu Leu Leu His Ala Leu Leu Ala His Leu Leu Ala Leu Leu
1               5                   10                  15

His His Leu Leu Ala Leu Leu Lys Lys Leu
            20                  25

<210> SEQ ID NO 32
<211> LENGTH: 24
<212> TYPE: DNA
<213> ORGANISM: Artificial Sequence
<220> FEATURE:
<223> OTHER INFORMATION: Synthetic primer forward

<400> SEQUENCE: 32
agcaagctta tggttcgtcc ttgg                                      24

<210> SEQ ID NO 33
<211> LENGTH: 24
<212> TYPE: DNA
<213> ORGANISM: Artificial Sequence
```

```
<220> FEATURE:
<223> OTHER INFORMATION: Synthetic primer reverse

<400> SEQUENCE: 33
agctctagac tagacggcat cctc                                    24

<210> SEQ ID NO 34
<211> LENGTH: 20
<212> TYPE: DNA
<213> ORGANISM: Artificial Sequence
<220> FEATURE:
<223> OTHER INFORMATION: Synthetic primer PSI forward

<400> SEQUENCE: 34
caggactcgg cttgctgaag                                         20

<210> SEQ ID NO 35
<211> LENGTH: 20
<212> TYPE: DNA
<213> ORGANISM: Artificial Sequence
<220> FEATURE:
<223> OTHER INFORMATION: Synthetic primer PSI reverse

<400> SEQUENCE: 35
tcccccgctt aatactgacg                                         20

<210> SEQ ID NO 36
<211> LENGTH: 19
<212> TYPE: DNA
<213> ORGANISM: Artificial Sequence
<220> FEATURE:
<223> OTHER INFORMATION: Synthetic probe

<400> SEQUENCE: 36
cgcacggcaa gaggcgagg                                          19

<210> SEQ ID NO 37
<211> LENGTH: 21
<212> TYPE: DNA
<213> ORGANISM: Artificial Sequence
<220> FEATURE:
<223> OTHER INFORMATION: Synthetic  titin forward

<400> SEQUENCE: 37
aaaacgagca gtgacgtgag c                                       21

<210> SEQ ID NO 38
<211> LENGTH: 20
<212> TYPE: DNA
<213> ORGANISM: Artificial Sequence
<220> FEATURE:
<223> OTHER INFORMATION: Synthetic titin reverse

<400> SEQUENCE: 38
ttcagtcatg ctgctagcgc                                         20

<210> SEQ ID NO 39
<211> LENGTH: 25
<212> TYPE: DNA
<213> ORGANISM: Artificial Sequence
<220> FEATURE:
<223> OTHER INFORMATION: Synthetic titin probe

<400> SEQUENCE: 39
tgcacggaag cgtctcgtct cagtc                                   25
```

<210> SEQ ID NO 40
<211> LENGTH: 1854
<212> TYPE: DNA
<213> ORGANISM: Artificial Sequence
<220> FEATURE:
<223> OTHER INFORMATION: Synthetic cDNA of mus musculus syncytin-A

<400> SEQUENCE: 40

```
atggttcgtc cttgggtttt ctgtctcctc ctgttcccct gttcctctgc ctactcggac     60
agctggatgc ccctggtaaa cctcactcaa cacctcctcc aggaggctaa ctcttccttc    120
tcttccaact gctgggtctg cttatccatc caaacccagc gctctctagc catgccagcc    180
ccactaagga cttggacaga gacacccatg aaacttcgaa tcatgtactc agcccggacc    240
ctctccggcc catacctat caccgacctt gagaggcgcc tccagaattt ccaaccattg    300
actccccact cctcttttgt caaccctgac cagcgggcca ttgctttcct tcagatcacc    360
agcgtgacag gcatacttcc catactttct cggatcacct cggtgagata ccccgatgac    420
cacgtctatg aatctgccca cgcccccata tggggctcac tctccaccca gacgatcctc    480
acctcccagg cccctctctg catatcccgc ttcttcaaga attcaaacca tgccaccttc    540
gtgggcaaac tccctgcctc tctttgcaat cacacctttc agctctcccc ctctgccaac    600
caccaatcca tagatctgtc ctccagctat gcattcgccc cattaatggc catgccaggg    660
tctaaatgga gaaccccctt acgcttttca ggacccccctt ccctgaactc agggatgcct    720
cactactcct gcccgataga tgacatccac tgccacacct accccaccac ccctggagg    780
tcctgtcctt ccttcccagc tagcacctgc tataatctca ccctattcga gccggacaat    840
tcgagccacc ctattaccct gtctgtggac accacatact tcaagattaa actccaggga    900
cacaaagacc cctatccact cttcagtac cagcccctca tgggggcagc cctctctgga    960
caatattcaa tctgggaata tgaacccact gttaagaaaa acggcggtat cactccaaat   1020
atcttctccc accttgtctc cttaacatac tccttctgcc tcaactcctc tggtgttttc   1080
ttcctctgtg gaaactcaac ttatgtctgt ctcccggcca attggtccgg cgtctgtacc   1140
cttgtcttcc aatacccgga tattgaactc cttcccaaca accaaaccat atctgtcccg   1200
cttttttgcta cagttccctc ctctgtcccc gcttctcgcc ggaagcgagc ccttcctctc   1260
cttcctctcc tcgcgggcct gggcattgct tctgccctgg ggttaggcat cgcgggtatc   1320
accacctcaa ctgtgtattt ccaacagctt tccaaggctc tctcggacag cctagatgaa   1380
atagccacct ccatcatcag cctccaagac caaatagact cgctggcggg tgtcgttctc   1440
caaaaccgca gagctctgga cctcattgtg gctgagaggg ggggcacctg cctcttcctc   1500
caggaagagt gctgcttcta cataaaccag tccggggtag tccggcacgc ggcaaggaaa   1560
cttcgagaaa gggcctcgga actcggcaca agctcgagtt cttggatcca gtggctgggg   1620
ctaggaccct ggctgccctc ttggttgact tccctcatgg ctcccattct ctttatcctg   1680
gtactgctgg ttttcaggcc ttgtcttctt aactgcctga ctcattctgt atcgcggcga   1740
atgagttctt tcattcacac caccaccgaa ggacacgtgg acaagatcct tctgcttcga   1800
gagtcccagt acaagagact ccccaagag ccccgagg aggatgccgt ctag            1854
```

<210> SEQ ID NO 41
<211> LENGTH: 1857
<212> TYPE: DNA
<213> ORGANISM: Artificial Sequence
<220> FEATURE:
<223> OTHER INFORMATION: Synthetic cDNA of mus musculus syncytin-B

```
<400> SEQUENCE: 41
atgacaggct tttgggtcct ctgtttcgtc cttttcccct cctccttatc ctatccggaa      60
agctggatgc cccttgtaaa cctcactcac cacatcctac gtgataccaa ctcttccctg     120
ttttccaact gttgggtctg cttgtctacc caaacccagc ggtccttagc agtcccagcc     180
cctctgtcca tttggacaga tacacccatg aagcttcatc ttacctactc agtcaggccc     240
ttctctggct ccttttccat tagcgacatt gaaagacgcc tccgtctctt ccgcccactg     300
actgcctcct attctttcca caatcctgac agaagggcga ttgcttttct tcaactcgtc     360
agctcaacag gcatatttcg gatcatcacc cggataacct ctgtgatata tccccataag     420
gaccgtttct tcgaatctgc ccaacgccct ctctgggggac cactctttac tgagaccgtg     480
ctcaggtcgc aggccccact ctgcatatct cgcttttttca aggtctcagc atatgccact     540
tttgtaggca acctctctgc ctctctctgc aactacacca tgcatatttc accttctacc     600
agtcatgaaa acctagatct ttccaccacc catacgttca aacaggcaat gaaaagaccg     660
gatgccaaat ggaaaaaccc gctccgtttt tccgggcccc cctccctcat cttctcgaag     720
ccggcttact atccctgccc aacagacatc aaacactgcc atacctctcc ggccactccc     780
tggatgcact gtcctcaggc tcccttcggc acctgctata acctcacttt atttgaacca     840
gacaactcaa cccaccctgt taccatgtca gtgaaccta cccacttcaa ggtcaaactc     900
caggggcaca gagacccta tccgctctcc cattaccagc ccctcacggg agctgccctg     960
tctggacaat attcagtctg ggagaacgag atcactgtcc aagaaaactg ggacatcacc    1020
tccaacattt tctcacatct tctcagcttc tcgtacgcct tctgcctcaa ctcttcaggc    1080
gttttcttcc tctgcggaac atcgacttac atctgcctcc cagccaattg gtccggtgtc    1140
tgtaccctgg tcttccaata cccggatatt gaacttctcc ccaataacca aacggtgcct    1200 gttcccttt ttgcttcagt tctttcctca gactcagttc ttcgcccaaa gaggtccct    1260 cacctcttc ccttccttgc aggcctgggt atctcttctg cccttggtac ggggatagct    1320
ggcttggcca cctcgactct ctatttccaa cagctttcta aggttctttc cgaaaccttg    1380
gaagaaatag ctgcctctat cactaccctc cagaaccaaa tagactcgct cgcaggtgtt    1440
gttctacaaa accgccgagc tctggacctc atcactgctg agaaaggggg cacctgtctc    1500
ttcctccagg aagagtgctg cttctacgta aaccagtctg gaatagtccg ggacgcggca    1560
aggaaactcc aagaacgagc atctgaactc ggccagcatt ctgactcttg gggacagtgg    1620
cctgaccttg gacgttggtt gccctggctg actcccttc tgggacctct tctcttcctc    1680
ttcttcctac tgacatttgg gtcttgtctt ctgaactgcc taacccgttt tgtgtcccag    1740
agacttggct cctttgttca agacactgcc aaaaggcatg tggacagcat cctccaaaat    1800
ttccaatata aaaaactgcc ccaagactcc ccagatgagg acaccattcc tacataa     1857
```